US010111822B2

(12) United States Patent
Shibuya et al.

(10) Patent No.: US 10,111,822 B2
(45) Date of Patent: Oct. 30, 2018

(54) EXTERNAL DERMAL COMPOSITION FOR ANTI-AGEING AND METHOD FOR PRODUCING THE SAME

(71) Applicant: Hayashibara Co., Ltd., Okayama (JP)

(72) Inventors: Takashi Shibuya, Okayama (JP); Akiko Miyake, Okayama (JP); Tatsuya Ishihara, Okayama (JP); Masaki Miyake, Okayama (JP); Hitomi Wake, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 0 days.

(21) Appl. No.: 14/655,068

(22) PCT Filed: Dec. 26, 2013

(86) PCT No.: PCT/JP2013/084817
§ 371 (c)(1),
(2) Date: Jun. 24, 2015

(87) PCT Pub. No.: WO2014/104171
PCT Pub. Date: Jul. 3, 2014

(65) Prior Publication Data
US 2015/0342854 A1    Dec. 3, 2015

(30) Foreign Application Priority Data

Dec. 27, 2012  (JP) ................................. 2012-285949
Dec. 27, 2012  (JP) ................................. 2012-285958
Oct. 11, 2013  (WO) .................. PCT/JP2013/077768

(51) Int. Cl.
A61K 8/67    (2006.01)
A61Q 19/02   (2006.01)
A61K 8/92    (2006.01)
A61K 8/98    (2006.01)
A61K 8/64    (2006.01)
A61K 8/49    (2006.01)
A61K 8/34    (2006.01)
A61Q 19/08   (2006.01)
A61K 8/97    (2017.01)
A61K 31/7048 (2006.01)
A61Q 19/00   (2006.01)
A61K 8/60    (2006.01)
A61K 8/9789  (2017.01)
A61K 8/9771  (2017.01)

(52) U.S. Cl.
CPC .............. A61K 8/676 (2013.01); A61K 8/345 (2013.01); A61K 8/498 (2013.01); A61K 8/4926 (2013.01); A61K 8/4953 (2013.01); A61K 8/602 (2013.01); A61K 8/64 (2013.01); A61K 8/922 (2013.01); A61K 8/97 (2013.01); A61K 8/9771 (2017.08); A61K 8/9789 (2017.08); A61K 8/988 (2013.01); A61K 31/7048 (2013.01); A61Q 19/00 (2013.01); A61Q 19/02 (2013.01); A61Q 19/08 (2013.01); A61K 2800/5922 (2013.01); A61K 2800/805 (2013.01)

(58) Field of Classification Search
None
See application file for complete search history.

(56) References Cited

U.S. PATENT DOCUMENTS

| | | | |
|---|---|---|---|
| 5,084,563 A * | 1/1992 | Sakai | A61K 8/67 424/60 |
| 5,137,723 A | 8/1992 | Yamamoto et al. | |
| 5,882,658 A | 3/1999 | Simon et al. | |
| 6,437,002 B1 | 8/2002 | Ito et al. | |
| 2001/0051711 A1 | 12/2001 | Yamasaki et al. | |
| 2003/0130331 A1* | 7/2003 | Donsbach | C07D 235/20 514/394 |
| 2007/0066565 A1 | 3/2007 | Mukai et al. | |
| 2007/0248633 A1 | 10/2007 | Baldo | |
| 2009/0041848 A1 | 2/2009 | Ain et al. | |
| 2011/0091726 A1 | 4/2011 | Shibuya et al. | |

FOREIGN PATENT DOCUMENTS

| | | |
|---|---|---|
| CA | 2828516 A1 | 9/2012 |
| CN | 1300215 A | 6/2001 |
| FR | 2924335 A1 | 6/2009 |
| JP | 59-10505 A | 1/1984 |
| JP | 61-152613 A | 7/1986 |
| JP | 3-135992 A | 6/1991 |
| JP | 3-139288 A | 6/1991 |

(Continued)

OTHER PUBLICATIONS

JP 06-220081; machine translation (1994)).*

(Continued)

Primary Examiner — Jake M Vu
(74) Attorney, Agent, or Firm — Browdy and Neimark, PLLC

(57) ABSTRACT

The present invention has an object to provide an external dermal composition for anti-ageing, which prevents or improves apparent skin problems such as wrinkles, fine wrinkles, blemishes, and saggings caused by increasing age or ageing; and maintains or improves the barrier function and the hyaluronic acid production in the skin. The object is solved by providing an external dermal composition for anti-ageing, which contains an aqueous medium as a base material and one or more ingredients selected from L-ascorbic acid, derivatives thereof, and their salts as an effective ingredient(s).

10 Claims, 3 Drawing Sheets

(56) References Cited

FOREIGN PATENT DOCUMENTS

| | | |
|---|---|---|
| JP | 05-339123 A | 12/1993 |
| JP | 6220081 | 8/1994 |
| JP | 6-247956 A | 9/1994 |
| JP | 06-263790 A | 9/1994 |
| JP | 63-104971 A | 5/1998 |
| JP | 2002-003330 A | 1/2002 |
| JP | 2002-88095 A | 3/2002 |
| JP | 2004-331524 A | 11/2004 |
| JP | 2005-95148 A | 4/2005 |
| JP | 2006-063060 A | 3/2006 |
| JP | 2006-063067 A | 3/2006 |
| JP | 2007291102 A | 11/2007 |
| JP | 2008-169196 A | 7/2008 |
| JP | 2008-255020 A | 10/2008 |
| JP | 2008-260721 A | 10/2008 |
| JP | 2009-040690 A | 2/2009 |
| JP | WO2007011066 A1 | 2/2009 |
| JP | 2009-249306 A | 10/2009 |
| JP | 2010-195686 A | 9/2010 |
| JP | 2012-67013 A | 4/2012 |
| WO | 99/59580 A1 | 11/1999 |
| WO | 20110361 A1 | 2/2002 |
| WO | 2005034938 A1 | 4/2005 |
| WO | 2007011066 A1 | 1/2007 |
| WO | 2007094312 A1 | 8/2007 |
| WO | 2012033218 A1 | 3/2012 |
| WO | 2012121297 A1 | 9/2012 |

OTHER PUBLICATIONS

Scifinder (20126).*

Schnider et al., Effects of age and diabetes mellitus on the solubility and nonenzymatic glucosylation of human skin collagen, J. Clin. Invest., 67:1630-1635 (1981).

Shin-Keshouhin-Handbook, pp. 518-539, Nikko Chemicals Co., Ltd.; published by Chou Printing Co. Ltd. (Oct. 30, 2006) with English language translation of excerpt.

* cited by examiner

EXTERNAL DERMAL COMPOSITION FOR ANTI-AGEING AND METHOD FOR PRODUCING THE SAME

TECHNICAL FIELD

The present invention relates to an external dermal composition for anti-ageing and a method for producing the same, more particularly, to an external dermal composition for anti-ageing that prevents or improves wrinkles, fine wrinkles, blemishes, or saggings in the skin, as well as to a basic skin care containing the external dermal composition and a method for producing these compositions.

BACKGROUND ART

Desire to be youthful to the end of time is a humans' common and universal desire, however, all humankind have experienced for long to have appeared wrinkles, fine wrinkles, blemishes, or saggings in the skin as they become older. Ageing also causes skin ageing, and the appearance of apparent changes such as wrinkles, fine wrinkles, blemishes, or saggings in the skin has been recognized to be so called natural providence as an unavoidable thing.

Recently, however, causatives or mechanisms of apparent changes such as wrinkles, blemishes, or saggings in the skin with ageing are gradually being revealed as the progress of researches on the structure and the metabolic mechanism of human skin. As well known, the skin is constructed by the outer thin epidermis (epithelium tissue) and the lower layered thick dermis (connective tissue); and the epidermis, as the outermost layer, protects living bodies from the outside world and prevents the leakage of internal moisture and nutrients to the outside of the bodies. While, the dermis is a connective tissue having the structure, where fibroblasts, collagens, elastins, proteoglycans and the like mainly spread complexly and three-dimensionally, which has roles for imparting strength, extensibility, and elasticity to the skin; however, the moisture-retaining ability of the cuticle in the skin surface will be lost as the decrease of sebum and moisture contents in the skin with ageing and it may become to easily induce fine wrinkles and rough skin due to dryness of the skin or the like.

Human epidermis, which is constructed by "keratinous layer" (stratum corneum), "granular layer", "stratum spinosum", and "stratum germinativum" located in this order from the outersurface, is finally cast off as a result of keratinocyte generated in the stratum germinativum, and sequentially moved to the outer surface. In particular, keratinocyte is proliferated in the stratum germinativum located in the innermost of the epidermis, differentiated, moved upward, finally turned into the keratinous layer located in the outermost of the keratinous layer (stratum corneum), and then desquamated as scurf. Such serial process of proliferation, movement, differentiation, and desquamation is called turnover, where the skin homeostasis is retained by newly rebirthing keratinocyte at a constant cycle that may induce wrinkles, saggings, and rough skin by delaying the turnover rate of the skin with ageing. Though the turnover rate of the skin varies depending on the sites of the body, it is said that healthy teenagers have a turnover rate of about 20 days; twenties, about 28 days; thirties, about 40 days; forties, about 55 days as roughly two times of that of twenties; and fifties, about 75 days. By the way, even if the turnover rate of the skin becomes fast or slow, it should not be preferable, while the normal skin turnover rate is recognized to be 28 days as that of twenties. The reason is that, when the turnover rate is fast, the level of melanin pigment, produced by melanocytes, for absorbing ultraviolet rays in the skin will increase; and this accelerates cosmetically-unfavorable melanin pigmentation by ultraviolet rays.

It is said that, as a recent finding, in vivo glycation in the skin (simply called "glycation", hereinafter) relates to the delaying of skin turnover rate and associates with skin ageing. Glycation may be also called Maillard reaction (or browning reaction) and meant as a process ranging from the binding of reducing saccharides such as glucose and fructose with the epidermis (collagen) or the keratinous layer (keratin) to the formation of substances called advanced glycation end products, i.e. AGEs. It is recognized that AGEs deposit on skin tissues and bind to a receptor for AGEs called RAGE; induce an inflammatory change in the skin or other tissues; form disorganized linkages in collagen intra- and inter-molecularly during the formation of AGEs to induce physical or physiological changes (deteriorations) on collagen; and cause skin ageing such as wrinkles, rough skin, saggings, or the reduction of skin firmness. It is also said that collagen, wherein disorganized linkages are formed intra- or inter-molecularly through glycation, would lose elasticity and become to be hardly decomposed by in vivo proteases, resulting in a delaying of skin turnover rate (see Non Patent Literature 1).

As described above, since the delaying of skin turnover rate with ageing is said to induce wrinkles, saggings, or rough skin, if any means for making up for a delayed turnover rate with ageing would be avairable, even though it is really hard to catch up the delayed turnover rate of the skin of a so called pre-ageing generation, including those in the around 30- to 50-year-old age group who start worrying about the above-identified skin conditions, to the level of the twenties as the normal skin turnover rate, it would possibly effectively improve such wrinkles, saggings, or rough skin. From this aspect, turnover rate may possibly be improved by either accelerating the turnover rate through the promotion of at least one step among sequential series of proliferation, migration, differentiation, and desquamation; or inhibiting glycation recognized as to induce the delaying of turnover rate; however, any actual means for solving it has not yet been provided.

When fibroblasts and hyaluronic acid in the dermis may be reduced with ageing or the breakage of collagen and the deterioration of elastin may be induced with ageing, wrinkles are allegedly formed or the elasticity of the skin are said to be lowered to cause dull or rough skin. There is also a finding that a non-smooth egestion of melanin excreted from melanocytes to epidermal cells may be causative for pigmentation (blemishes) and dullness of the skin.

Based on these research results and findings, at present, there can be seen proposals (see, for example, Patent Literatures 1 to 7) so called external dermal agents for anti-ageing that theoretically prevent or improve the apparent changes such as wrinkles, fine wrinkles, blemishes, saggings in the skin, or the like in the skin with ageing, in terms of scientific point of view, whereby humans are getting nearer to the realization of the desire to keep youthfulness to the end of time step by step. Currently-proposed external dermal agents for anti-ageing, however, have only pursued and realized quite partial possibilities from among many possibilities. Accordingly, there is still desired a providing of a novel external dermal agent for anti-ageing from different angles, including distinctly different mechanisms of exerting anti-ageing effects from currently-proposed external dermal agents for anti-ageing, which have been merely realized as a result of pursuing only a part of various possibilities, conveniences, and production feasibilities.

PRIOR ART LITERATURES

Patent Literatures

Patent Literature 1: Japanese Republication No. WO2007/011066
Patent Literature 2: Japanese Patent Kokai No. 2007-291102
Patent Literature 3: Japanese Patent Kokai No. 2008-169196
Patent Literature 4: Japanese Patent Kokai No. 2008-255020
Patent Literature 5: Japanese Patent Kokai No. 2008-260721
Patent Literature 6: Japanese Patent Kokai No. 2009-040690
Patent Literature 7: Japanese Patent Kokai No. 2009-249306

Non-Patent Literature

Non-Patent Literature 1: *The Journal of Clinical Investigation*, Schneider, S. L., et al., Vol. 67, pp. 1630-1635, 1981

DISCLOSURE OF INVENTION

Object of the Invention

The present invention, which was made based on the current state of the above prior art, aims to provide a novel external dermal composition for anti-ageing and a basic skin care which contains the same directed to prevent or improve skin changes such as wrinkles, fine wrinkles, blemishes, saggings in the skin that are inducible with ageing; and to provide a method for producing the same.

Means to Attain the Object

The present inventors have eagerly researched and made efforts to solve the above objects. As a result, they found that L-ascorbic acid, derivatives thereof, and their salts have remarkable anti-ageing effects, i.e., effects of improving the skin turnover, maintaining or improving the barrier function of the skin, and maintaining or improving the production of hyaluronic acid in the skin; resulting in preventing or improving wrinkles, fine wrinkles, blemishes, saggings, etc., in the skin that are appeared with ageing; and found that an external dermal composition that exerts the above effects can be easily produced by a production method containing a step of mixing the above L-ascorbic acid, derivatives thereof, or their salts with an aqueous medium used as a base material. Thus, they accomplished the present invention.

The present invention solves the above objects by providing an external dermal composition for anti-ageing, which contains an aqueous medium as a base material and one or more members selected from L-ascorbic acid, L-ascorbic acid derivatives, and their salts as an effective ingredient(s); and a basic skin care containing the external dermal composition. The present invention also solves the above objects by providing a method for producing an external dermal composition for anti-ageing or a basic skin care, which contains a step of mixing one or more members selected from L-ascorbic acid, L-ascorbic acid derivatives, and their salts with an aqueous medium as a base material.

The effective ingredient(s) for the external dermal composition and the basic skin care of the present invention is/are basically L-ascorbic acid. Since L-ascorbic acid has reducibility and easily loses its physiological activity due to its high unstableness, derivatives of L-ascorbic acid are more preferably used than L-ascobic acid per se. Such L-ascorbic acid or derivatives thereof can be in a salt form. L-Ascorbic acid is released from such salts of L-ascorbic acid in an aqueous medium, while salts of L-ascorbic acid derivatives release L-ascorbic acid derivatives in an aqueous medium, whereby the released L-ascorbic acid derivatives further release L-ascorbic acid via the action of an enzyme present in living human bodies when applied to the skin. Accordingly, in addition to L-ascorbic acid, one or more members selected from derivatives and salts of L-ascorbic acid are used in the external dermal composition and the basic skin care of the present invention as an effective ingredient(s) having an anti-ageing effect of preventing or improving wrinkles, fine wrinkles, blemishes, saggings, etc., appeared in the skin with ageing.

Glycosyl-, acyl-, or phosphoryl-derivatives of L-ascorbic acid are preferably used as L-ascorbic acid derivatives; among which 2-O-α-D-glucosyl-L-ascorbic acid or sodium salt thereof as a glycosyl derivative of L-ascorbic acid is more preferably used because it is quite stable and exerts a remarkable anti-ageing effect when incorporated in the external dermal composition or the basic skin cares of the present invention.

Such 2-O-α-D-glucosyl-L-ascorbic acid and sodium salt thereof are preferably used in a crystalline form. Examples of suitably used crystalline 2-O-α-D-glucosyl-L-ascorbic acid include, for example, a particulate composition containing anhydrous crystalline 2-O-α-D-glucosyl-L-ascorbic acid as disclosed in Japanese Patent Kokai Nos. 135992/91, 2012-67013, etc., applied by the same applicant as the present invention.

While, examples of crystals of sodium salt of 2-O-α-D-glucosyl-L-ascorbic acid include a hydrous crystal thereof having diffraction peaks at diffraction angles (2θ) of 6.8°, 8.2°, 14.3°, 17.8°, and 18.4°, or an anhydrous crystal thereof having diffraction peaks at diffraction angles (2θ) of 8.0°, 9.0°, 16.4°, 17.9°, and 20.8°. These hydrous and anhydrous crystalline sodium salts of 2-O-α-D-glucosyl-L-ascorbic acid, which are novel crystals constructed by the present inventors, can be advantageously, particularly, suitably used in the present invention as the effective ingredient(s) of the present invention because they are easily highly-purified by crystallization and easily confirmed their properties, effectiveness, and safeness, as well as being advantageously, relatively easily prepared into high-purity preparations for use as the effective ingredients of the present invention.

For reference, 2-O-α-D-glucosyl-L-ascorbic acid as a glycosyl derivative of L-ascorbic acid exhibits a relatively strong acidity in an aqueous medium and it usually essentially requires a step of neutralizing it with an appropriate alkali to give a pH of around 5 to 9 when incorporated into external dermal agents or cosmetics to be applied to the skin. The above-mentioned hydrous and anhydrous crystalline sodium salts of 2-O-α-D-glucosyl-L-ascorbic acid, however, exhibit alkalinity in an aqueous medium, and therefore, the combination use of 2-O-α-D-glucosyl-L-ascorbic acid and its crystalline sodium salt can produce external dermal compositions or basic skin cares having a pH within the desired pH range without neutralizing 2-O-α-D-glucosyl-L-ascorbic acid with an alkali as a quite advantageous merit by appropriately controlling the composition ratio of them. When used in combination, 2-O-α-D-glucosyl-L-ascorbic acid and hydrous and/or anhydrous crystalline sodium salt thereof can be conveniently incorporated into a composition for use in an appropriate ratio to give a predetermined desired pH range after being mixed with an aqueous medium. In the case of an external dermal composition or a basic skin care such as a face wash, which is allowed to have an alkaline pH, it goes without saying that hydrous and/or anhydrous crystals of sodium salt of 2-O-α-D-glucosyl-L-ascorbic acid can be used alone as an effective ingredient without being used in combination with 2-O-α-D-glucosyl-L-ascorbic acid.

Although the external dermal composition of the present invention can be used alone as an external dermal composition for anti-ageing, it can be preferably used as basic skin cares after the addition of commonly used appropriate cosmetic ingredients. For example, the external dermal composition for anti-ageing of the present invention can be made into a cosmetic lotion after the addition of ethanol and a humectant, and the resulting cosmetic lotion can be incorporated with one or more astringents, cuticles softener, emollients, and surfactants. Such cosmetic lotion can be arbitrarily incorporated with one or more flavors, pigments, antiseptics, ultraviolet-ray-absorbing agents, sequestering agents, and buffers.

The external dermal composition for anti-ageing of the present invention can be made into a face-wash by the addition of an alkaline salt of a higher fatty acid (a soap), and needless to say that it can be incorporated with one or more flavors, pigments, antioxidants, and sequestering agents. Needless to add, glycerin, ethanol, sugar, polyalcohols, or antiseptics can be further added to such a face-wash.

The external dermal composition for anti-ageing of the present invention can be made into a serum by the addition of a humectant and emollient, and such a serum can be incorporated with one or more flavors, ultraviolet-ray-absorbing agents, skin-whiteners, anti-inflammatories, antiseptics, and bactericides. Also, the external dermal composition for anti-ageing of the present invention can be made into a milky lotion by the addition of an appropriate oily ingredient and surfactant, and such a milky lotion can be incorporated with one or more appropriate humectants, emollients, blood circulation accelerators, and high molecular substances. Further the external dermal composition for anti-ageing of the present invention can be made into a cream by the addition of an appropriate oily ingredient and surfactant, and the cream can be appropriately incorporated with spermaceti, cetanol, lanolin, liquid paraffin, petrolatum, glycerin, or squalane.

The term "skin-turnover-improving" as referred to in the present invention means to maintain a series of steps (turnover) of proliferation, migration, differentiation, and desquamation of epidermal cells (keratinocytes) as the origin of the skin composed of "keratinous layer (stratum corneum)", "layer of corneocytes", "stratum spinosum", and "basal layer" at its healthy conditions. More concretely, it means to improve the reduction of turnover rate of the skin with ageing.

The term "maintaining or improving the barrier function in the skin" as referred to in the present invention means that maintaining or improving the function of a keratinous layer called as a secondary barrier, which corresponds to the function of a sebum barrier called as a primary barrier; the function of protecting either the invasion of foreign substances into living bodies from the outside of the bodies or the release of an excessive amount of moisture from the internal of the bodies to the external thereof, and the maintenance or the improvement of the function of separating the inside of living bodies from the outside thereof by adherens junction structure called tight junction (TJ) that exists in a granular layer of epidermis adjacent to a keratinous layer. For reference, such a keratinous layer is a layer composed of corneocytes piled up in multiple layers, wherein in the outermost layer thereof there exists a tight membrane, which is composed of proteins such as involucrin, called as a cornified envelope (CE) that protects the inside of corneocytes. The above-identified CE and TJ play important roles in skin barrier function. When the skin barrier function lowers, collagen, elastin, hyaluronan (hyaruronic acid), etc., which exist in the dermis, will be damaged by the exposure of ultraviolet rays, particularly, ultraviolet A (long-wave) that reaches up to the dermis; also such lowering may be known to induce skin dryness and excessive sebum secretion to induce adults acne or may induce any disorder of turnover. With ageing, skin barrier function will lower, resulting in inducing wrinkles, fine wrinkles, blemishes, saggings, etc., in the skin.

Further, the term "maintaining or improving the production of hyaluronic acid" as referred to in the present invention means an enhancement of the production level of hyaluronic acid from hyaluronic acid-producing cells in the skin, resulting in maintaining and improving skin barrier function and then imparting an anti-ageing effect.

Also, the term "inhibiting glycation" as referred to in the present invention means to inhibit a reaction (also called Maillard reaction or browning reaction), where reducing saccharides such as glucose, fructose, and the like nonenzymatically bind to the dermis (collagen) or the keratinous layer (keratin) to form substances called advanced glycation end products (AGEs). AGEs are known to induce skin ageing such as wrinkles, rough skin, dullness, and reduction of firmness.

Effect of the Invention

According to the external dermal composition for anti-ageing and the basic skin cares containing the same of the present invention, changes in the skin with ageing such as wrinkles, fine wrinkles, blemishes, and saggings in the skin can be effectively prevented or improved as advantageous merits. Particularly, in the case of using 2-O-α-D-glucosyl-L-ascorbic acid or sodium salt thereof as a glycosyl derivative of L-ascorbic acid as an effective ingredient, there can be exerted an advantageous merit that the effective ingredients are highly stably retained in the resulting external dermal compositions and basic skin cares to exert a distinct anti-ageing effect when applied to the skin. In the case of using 2-O-α-D-glucosyl-L-ascorbic acid and/or sodium salt thereof in a crystalline form, they can be made into a distinctly high purity 2-O-α-D-glucosyl-L-ascorbic acid and/or sodium salt thereof by excluding impurities contained their materials as much as possible for use as effective ingredients for the external dermal compositions and the basic skin cares, while ensuring a distinctly high safeness and applicability to the skin with safeness as advantageous merits. When 2-O-α-D-glucosyl-L-ascorbic acid and sodium salt thereof are used in combination for producing the external dermal composition for anti-ageing and the basic skin cares containing the same according to the present invention, 2-O-α-D-glucosyl-L-ascorbic acid exhibits a relatively strong acidity but the sodium salt exhibits an alkalinity when they are mixed with an aqueous medium; there can be exerted an advantageous merit that an external dermal composition and the basic skin cares with a pH within a desired pH range without neutralizing 2-O-α-D-glucosyl-L-ascorbic acid with any alkali by appropriately controlling their ratio.

BEST MODE FOR CARRYING OUT THE INVENTION

Figure 1:
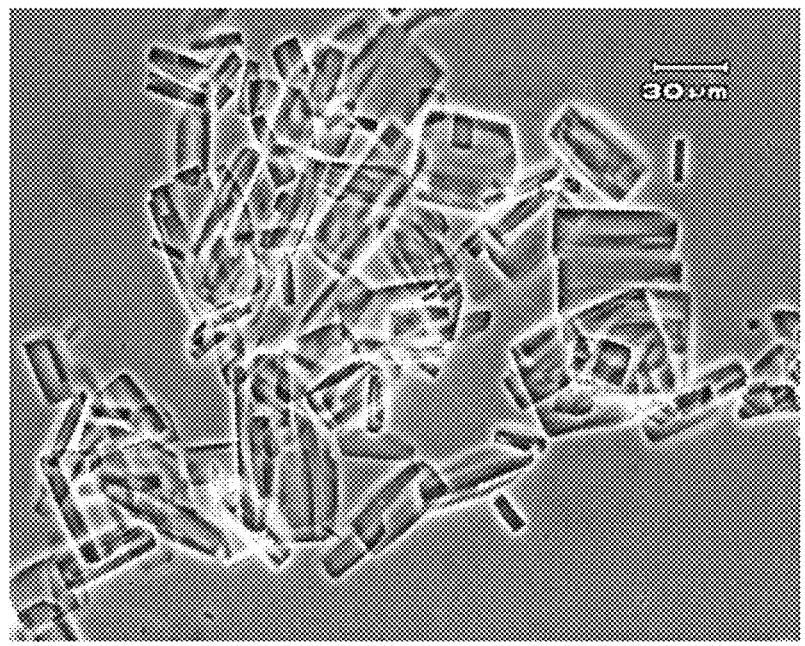
FIG. 1 A microscopic photograph of a crystalline sodium salt of ascorbic acid 2-glucoside (hydrous crystal).

The present invention relates to an external dermal composition for anti-ageing, which contains an aqueous medium as a base material and one or more ingredients selected from L-ascorbic acid, derivatives thereof, and their salts as an effective ingredient(s); a basic skin care containing the external dermal composition; and a method for producing the same. Hereinafter, the above external dermal composition of the present invention is firstly explained and then the basic skin care and the method of the same according to the present invention are explained.

A. External Dermal Composition for Anti-Ageing

The external dermal composition for anti-ageing of the present invention (called simply "external dermal composition", hereinafter) contains one or more ingredients selected from L-ascorbic acid, derivatives thereof, and their salts as an effective ingredient(s). L-Ascorbic acid is a compound that exerts an important physiological function in living bodies as vitamin C and it has been also used as an antioxidant and anti-inflammatory; and it has been widely used as a useful component in a cosmetic field because of its skin-whitening effect and collagen-production-enhancing action. Since L-ascorbic acid effectively prevents or improves wrinkles, fine wrinkles, blemishes, and saggings in the skin when incorporated in external dermal compositions, it can be used as an effective ingredient in the external dermal composition of the present invention.

L-Ascorbic acid, however, has a defect that it is quite unstable and susceptive to oxidation decomposition to lose its physiological activities due to its reducibility. Because of this, L-ascorbic acid requires extreme caution in storing and handling, and it should be foreseen the amount that will be decomposed by oxidation before its use and should be incorporated in an amount that far exceeds its possible requisite amount. Accordingly, more preferable examples of the effective ingredients used in the external dermal composition of the present invention are derivatives of L-ascorbic acid and salts thereof that are more stable than L-ascorbic acid per se and capable of exerting the intrinsic functions of L-ascorbic acid released therefrom in vivo.

Any derivatives of L-ascorbic acid suitably used as the effective ingredients of the external dermal composition of the present invention should not specifically be restricted to specific ones as long as they in themselves are more stable than L-ascorbic acid and capable of exerting the intrinsic functions of L-ascorbic acid after releasing L-ascorbic acid in vivo. Examples of such derivatives of L-ascorbic acid usable as the effective ingredients of the external dermal composition of the present invention can be listed as glycosyl derivatives, acyl derivatives, and phosphoryl derivatives of L-ascorbic acid.

Examples of the glycosyl derivatives of L-ascorbic acid include the one, wherein a glycosyl group binds to the C-2 position of L-ascorbic acid, suitably used because of its high stableness. Examples of such derivatives can be listed as 2-O-α-glycosyl-L-ascorbic acid (ascorbic acid 2-glucoside), wherein a series of glycosyl groups such as glucosyl-, maltosyl-, and maltotriosyl-groups bind to the C-2 position of L-ascorbic acid via an α-fashion as disclosed in Japanese Patent Kokai Nos. 135992/91, 139288/91, etc.; and 2-O-β-D-galactosyl-L-ascorbic acid (ascorbic acid 2-galactoside), wherein a galactosyl group binds to the C-2 position of L-ascorbic acid via a β-fashion as disclosed, for example, in Japanese Patent Kokai No. 263790/94.

Examples of the acyl derivatives (or fatty acid ester derivatives) of L-ascorbic acid include ascorbic acid palmitate ester, ascorbic acid dipalmitate ester, ascorbic acid tetrahexyldecanoic acid ester, ascorbic acid cholesterol ester, etc., as disclosed in Japanese Patent Kokai Nos. 10505/84, 104971/88, 247956/94, 2004-331524, etc. Examples of phosphoryl derivatives of L-ascorbic acid include ascorbic acid 2-phosphoric ester and metal salts thereof as disclosed in Japanese Patent Kokai Nos. 152613/86, 339123/93, 2002-3330, 2006-63060, etc.

Among the above-mentioned derivatives of L-ascorbic acid, glycosyl derivatives of L-ascorbic acid are most favorably used because of their high stableness, and among which 2-O-α-D-glucosyl-L-ascorbic acid, wherein a glucosyl group binds to the C-2 position of L-ascorbic acid via an α-fashion (abbreviated as "ascorbic acid 2-glucoside" throughout the specification, hereinafter) is most preferable. Ascorbic acid 2-glucoside is a derivative of L-ascorbic acid, which was explored to overcome the above-identified defect of L-ascorbic acid, has groundbreaking properties of showing no reducibility, having stableness, and exerting the intrinsic physiological activities of L-ascorbic acid after being decomposed into L-ascorbic acid and D-glucose by in vivo enzymes in living bodies. As disclosed, for example, in Japanese Patent Kokai Nos. 135992/91, 139288/91, etc., ascorbic acid 2-glucoside can be produced on an industrial scale by a method of allowing cyclomaltodextrin glucanotransferase as a saccharide-transferring enzyme to act on a solution containing L-ascorbic acid and amylaceous substance, and then allowing glucoamylase to act on the resulting ascorbic acid 2-glycoside.

Suitable examples of such ascorbic acid 2-glucoside are those in a partially or wholly crystalline form; the higher the ratio of crystals in the whole ascorbic acid 2-glucoside used, the higher the purity of ascorbic acid 2-glucoside and further the more stable the property thereof. The whole content of ascorbic acid 2-glucoside used, however, should not necessarily be in a wholly crystalline form and it can be in the form of a particulate composition containing crystals partially coexisted with amorphous ascorbic acid 2-glucoside. It is well known that ascorbic acid 2-glucoside exists in an anhydrous crystalline form. Examples of crystals of ascorbic acid 2-glucoside suitably used in the present invention include a particulate composition containing anhydrous crystalline 2-O-α-D-glucosyl-L-ascorbic acid as disclosed in Japanese Patent Kokai No. 135992/91 and International Patent Publication No. WO2012/121297. Examples of commercialized ones include "AA2G", a product name of a particulate composition containing anhydrous crystalline ascorbic acid 2-glucoside, commercialized by Hayashibara Co., Ltd., Okayama, Japan.

The L-ascorbic acid or the derivatives thereof used as the effective ingredient(s) of the external dermal composition of the present invention can be those in a salt form as long as they are dissociated into L-ascorbic acid or derivatives thereof when mixed with an aqueous medium.

Examples of salts particularly preferably used as the effective ingredient(s) in the external dermal composition of the present invention include sodium salt of ascorbic acid 2-glucoside. Such sodium salt of ascorbic acid 2-glucoside can be obtained, for example, by neutralizing an aqueous solution of ascorbic acid 2-glucoside with an alkali, and drying the resulting mixture. Varying depending on pH, since at least a part of sodium salt of ascorbic acid 2-glucoside is dissociated into ascorbic acid 2-glucoside and sodium when dissolved in an aqueous medium, it can be particularly preferably used in the present invention similarly as ascorbic acid 2-glucoside.

Similarly as in ascorbic acid 2-glucoside, sodium salt of ascorbic acid 2-glucoside can be more preferably used in a crystalline form. A crystalline sodium salt of ascorbic acid 2-glucoside is a novel crystal created by the present inventors. Although crystalline powders of aluminum salt or zinc salt of ascorbic acid 2-glucoside have been reported in Japanese Patent Kokai No. 220081/94, there exists no report on crystalline sodium salt of ascorbic acid 2-glucoside. In the above-identified patent publication, crystalline powders of aluminum salt or zinc salt of ascorbic acid 2-glucoside are reported to have respectively obtained by dissolving ascorbic acid 2-glucoside and an aluminum compound in cold water, stirring the resulting solution, centrifuging the solution, and either freeze-drying the resulting supernatant or adding NaOH to the resulting zinc compound, followed by stirring the mixture, centrifuging the resultant, adding the resulting precipitate to an aqueous solution of ascorbic acid 2-glucoside, filtering the aqueous solution, and freeze-drying the filtrate. The present inventors repeated similar methods as those of the above patent publication to obtain a crystalline sodium salt of ascorbic acid 2-glucoside; however, none of the methods, which had been reported to have succeeded in obtaining crystalline powders of aluminum salt or zinc salt of ascorbic acid 2-glucoside, yielded a crystalline powder of sodium salt of ascorbic acid 2-glucoside.

The present inventors subsequently continued researching on and repeated trial and error and unexpectedly succeeded in obtaining a crystalline sodium salt of ascorbic acid 2-glucoside by adding an excessive amount of sodium hydroxide in an aqueous solution to ascorbic acid 2-glucoside into an alkaline solution, adding an organic solvent to the alkaline solution, and allowing the resulting mixture to stand.

As shown in the later described Experiments, the crystalline sodium salt of ascorbic acid 2-glucoside found by the present inventors can exist in any of a hydrous crystalline or anhydrous crystalline form; the one in a hydrous crystalline form has characteristic diffraction peaks at diffraction angles (2θ) of 6.8°, 8.2°, 14.3°, 17.8°, and 18.4°, when determined on powder X-ray diffraction analysis; and the other in an anhydrous crystalline form has characteristic diffraction peaks at diffraction angles (2θ) of 8.0°, 9.0°, 16.4°, 17.9°, and 20.8°, when determined on powder X-ray diffraction analysis. For reference, the present inventors succeeded in obtaining a single crystal with a size that affords X-ray crystal structural analysis for the hydrous crystalline sodium salt of ascorbic acid 2-glucoside; and revealed that, as shown in the later described Experiment, the hydrous crystal belongs to an orthorhombic system and exhibits a space group of Pbca(#61) and a lattice constant of a=6.9733 Å, b=14.4839 Å, c=19.3221 Å, when determined on X-ray crystal structural analysis.

For comparison, according to the later described inductively-coupled plasma emission spectrometry, the sodium content in the anhydrous crystalline sodium salt was about 8.7% by mass. While, the theoretical sodium content is 8.8% by mass which well coincides with the measured value, on the assumption that the above-identified anhydrous crystal is composed of ascorbic acid 2-glucoside and sodium salt and the quantitative ratio is an atom of sodium and ½ molecule of sodium hydroxide against one molecule of ascorbic acid 2-glucoside. At this point, the molar ratio of ascorbic acid 2-glucoside to sodium is about 1:1.5, meaning that two molecules of ascorbic acid 2-glucoside contain three molecules of sodium. As shown in the later described result in the measurement of moisture content, the hydrous crystalline sodium salt of ascorbic acid 2-glucoside has a moisture content of about 15% by mass. Assuming that the hydrous crystal contains ascorbic acid 2-glucoside, sodium, and sodium hydroxide in the same molar ratio as in the anhydrous crystal, the molar ratio of ascorbic acid 2-glucoside and water molecule is about 1:4, indicating that the hydrous crystal contains four molecules of crystallization water against one molecule of ascorbic acid 2-glucoside.

In general, organic compounds are said to have crystal polymorphism, and even the same compound, it can take plurality of different crystalline structures and may have different properties, including solubility depending on the crystalline structures. In the case of using organic compounds, for example, using them as effective ingredients of external dermal compositions and basic skin cares, it is quite beneficial to obtain their crystals, when they can exist in a crystalline form, and to reveal their crystalline structures for the sake of stably maintaining and securing properties suitable for their applications. The external dermal composition and the basic skin care of the present invention use sodium salt of ascorbic acid 2-glucoside as an appropriate effective ingredient, and a crystalline sodium salt of ascorbic acid 2-glucoside has now been obtained by the present inventors who revealed that the crystalline sodium salt exists in an anhydrous or hydrous crystalline form, and analyzed their characteristic powder X-ray diffraction patterns and crystalline structures. Accordingly, in the case of using sodium salt of ascorbic acid 2-glucoside in the form of the above-identified anhydrous- or hydrous-crystal, they can be easily prepared into highly purified materials and easily confirmed their handlings, effectiveness, and safeness, as well as being always expected to have consistent and known stable-properties as quite advantageous merits.

The method for producing crystalline sodium salt of ascorbic acid 2-glucoside used in the present invention should not specifically be restricted as long as it yields a desired crystal; hydrous crystalline sodium salt of ascorbic acid 2-glucoside can be obtained by dissolving ascorbic acid 2-glucoside in an aqueous sodium hydroxide solution, adding an organic solvent to the solution, allowing the resulting solution to stand to precipitate crystals, and collecting the precipitated crystals by using a solid-liquid separation method such as centrifugation. Ascorbic acid 2-glucoside with a relatively high purity is desirably used as a material, and usually an anhydrous crystalline ascorbic acid 2-glucoside with a purity of at least 90% by mass, desirably, at least 95% by mass, and more desirably, at least 99% can be suitably used as the material.

Washing the resulting hydrous crystal with an aqueous ethanol can make it into a high purity hydrous crystal. The obtained hydrous crystal can be, if necessary, pulverized and dried into a particulate composition containing hydrous crystalline sodium salt of ascorbic acid 2-glucoside. The hydrous crystal obtained by the above method can be converted into anhydrous crystalline sodium salt of ascorbic acid 2-glucoside by drying it in vacuo while heating. The obtained anhydrous crystal can be reconverted into hydrous crystal by allowing it to absorb moisture under a relative humidity of at least 75%. A particulate composition containing hydrous or anhydrous crystalline sodium salt of ascorbic acid 2-glucoside can be obtained by spray-drying a massecuite prepared by adding an organic solvent to sodium salt of ascorbic acid 2-glucoside to precipitate crystals.

Anhydrous or hydrous crystalline sodium salt of ascorbic acid 2-glucoside exhibits alkalinity, when dissolved in water, as a characteristic feature thereof. This feature contrasts sharply with anhydrous crystalline ascorbic acid 2-glucoside that exhibits a relatively strong acidity when dissolved in water. Because of this, the novel crystalline sodium salt of ascorbic acid 2-glucoside created by the present inventors can be preferably used in various uses, where the amounts and the forms of use thereof and even the use thereof per se are restricted, because conventional anhydrous crystalline ascorbic acid 2-glucoside exhibits a relatively strong acidity when in an aqueous solution form. When used in soap-related external dermal compositions that require a slight alkalinity, for example, soaps, shampoos, cleansing foams, body soaps, etc., conventional particulate compositions containing anhydrous crystalline ascorbic acid 2-glucoside inevitably require a handling of neutralization of acid solutions of ascorbic acid 2-glucoside dissolved in an aqueous medium prior to use and also require the addition of buffers for pH control, but since aqueous solutions, obtained by dissolving crystalline sodium salt of ascorbic acid 2-glucoside in water, usually exhibit alkalinity and this would eliminate the need for a handling of neutralizing ascorbic acid 2-glucoside with an alkali, as well as often for the combination use with any buffer.

In the case of using anhydrous or hydrous crystalline sodium salt of ascorbic acid 2-glucoside in combination with anhydrous crystalline ascorbic acid 2-glucoside, an appropriate control of their composition ratio can provide, as a merit, an aqueous solution of ascorbic acid 2-glucoside with a pH within a prescribed pH range, for example, within a slightly alkaline to a slightly acidity range, when dissolved in an aqueous medium. When anhydrous or hydrous crystalline sodium salt of ascorbic acid 2-glucoside is used in combination with anhydrous crystalline ascorbic acid 2-glucoside, there can provide, as a merit, various compositions, which are preferably adjusted to give a pH ranging from a slightly alkaline pH to a slightly acidic pH as a whole, including the external dermal compositions and the basic skin cares of the present invention, without using any additional alkali other than the anhydrous or hydrous crystalline sodium salt of ascorbic acid 2-glucoside. In using them both in combination, anhydrous crystalline ascorbic acid 2-glucoside and anhydrous or hydrous crystalline sodium salt of ascorbic acid 2-glucoside can be weighed in an amount corresponding to respective composition ratios before use, however, it is convenient to make them into compositions, which can be previously prepared by mixing anhydrous crystalline ascorbic acid 2-glucoside and anhydrous or hydrous crystalline sodium salt of ascorbic acid 2-glucoside in a prescribed composition ratio, preferably, in a composition ratio of 60:40 to 45:55 by mass on a dry solid basis (d.s.b.), to meet the pH requisite for a desired composition. The amount of anhydrous or hydrous crystalline sodium salt of ascorbic acid 2-glucoside or anhydrous crystalline ascorbic acid 2-glucoside in the external dermal composition or the basic skin care of the present invention is usually 0.001% by mass or more, preferably, 0.01 to 50% by mass, more preferably, 0.1 to 20% by mass, and more preferably, 1 to 10% by mass in terms of the total anhydrous crystalline L-ascorbic acid against the mass of the composition or the basic skin care. When the amount is below the above lower limit or over the above upper limit, it is not preferable because it may distinctly reduce or not exert the desired effects.

As described above, ascorbic acid 2-glucoside and/or sodium salt thereof can be preferably used as the effective ingredient(s) of the external dermal composition of the present invention. Sodium salt of ascorbic acid 2-glucoside, at least a part of which dissociates into ascorbic acid 2-glucoside and sodium in an aqueous medium to form ascorbic acid 2-glucoside. Ascorbic acid 2-glucoside is hydrolyzed into L-ascorbic acid and D-glucose by the action of in vivo enzymes in living bodies, for example, α-glucosidase, to exert functions as L-ascorbic acid. Accordingly, the incorporation of an α-glucosidase inhibitor into the external dermal composition of the present invention as needed will delay the formation of L-ascorbic acid from the composition when applying the composition to the skin, resulting in imparting its anti-ageing effect in a durable or slow-acting manner. Conversely, the external dermal composition of the present invention can be imparted an immediate effect by optionally incorporating thereunto an α-glucosidase activator to accelerate the formation of L-ascorbic acid when applied to the skin.

Any competitive and non-competitive inhibitors can be used as the above-identified α-glucosidase inhibitor. Concrete examples of such include starch hydrolyzates such as maltotriose, maltotetraose, maltopentaose, maltoheptaose, and panose; sugar alcohols such as maltitol, maltotriitol, maltotetraitol, maltopentaitol, maltohexaitol, maltoheptaitol, erythritol, 1-thio-D-glucitol; monosaccharides such as arabinose, fucose, 2-deoxy-D-galactose, xylose, ribose, tagatose, ribulose, lyxose, xylulose, and α-methyl-D-xyloside; oligo- or poly-saccharides such as oligosaccharides derived from fukoidan and polysaccharides derived from soy beans; nucleotides such as adenylic acid, guanylic acid, cytidylic acid, uridylic acid, and inosinic acid; nucleosides such as guanosine, deoxyguanosine, adenosine, deoxyadenosine, cytidine, uridine, inosine, and deoxyinosine; and plant extracts such as Asian ginseng, *Aloe barbadensis* Miller, *Hypericum, Malvaceae* (mallows), *Salacia reticulata, Connarus cochinensis, Sapium discolor, Xanthophyllum annamense, Paris tetraphylla, Dimocarpus longan, Erythroxylon cambodianum, Diospyros malabarica,* touch, *Careya arborea,* mulberry tree, *Semecarpus cochinchinensis, Calophyllum calaba, Shorea guiso, Duabanga sonneratioides, Cratoxylon formosum, Archidendron Turgidum, Nauclea officinalis, Eupatorium odoratum, Hibiscus mesnyi, Myrcia sphaerocarpe, Milletia diptera, Milletia conraui, Ascophyllum nodosum, Brucea javanica, Mangifera indicia, Sesbania grandiflora, Glycyrrhiza uralensis, Rumex bucephalophorus, Murtex communis, Taraxacum officinale, Viscum album, Ganoderma lucidum, Pinus densiflora, Penarus schulzei, Origanum majorana, Grifola frondosa,* Sangzhi (*Ramulus mori*), *Lobelia chinensis, Angelica acutiloba* (dong quai), *Syzygium aromaticum, Commelina communis, Salacia reticulata, Eucommia ulmoides, Angylocalyx boutiqueanus, Arachniodes standishii,* laurel, *Psidium guajava* (guava), astringent coats of chestnuts and peanuts, and *Oryza sativa* subsp. *Javanica*.

Examples of the α-glucosidase activator include plant extracts such as *Arnica montana*, german camomile flower, *Salvia officinalis*, soy beans, *Artemisia indica* var. *maximowiczii*; and microorganisms such as yeasts, bifidobacteria, and lactic acid bacteria.

Since the L-ascorbic acid, derivatives thereof, and their salts used in the present invention exert in themselves an action of improving the turnover of the skin and an action of maintaining or enhancing the barrier function and the hyaluronic acid production in the skin, they can be advantageously used alone as effective ingredients of the external dermal composition of the present invention; however, if necessary, when incorporated with the later described plant extracts or compounds having a skin-turnover-improving action, the anti-wrinkle action, anti-fine wrinkle action, skin-whitening action, anti-blemishes, and anti-saggings in the skin, as well as the above functions and effects exerted by the L-ascorbic acid, derivatives thereof, and their salts as the effective ingredients can be even increased up to a level of over their additive effects; the combination use of the external dermal composition of the present invention with any of the above plant extracts or compounds can be particularly useful in practicing the present invention because they do not hinder the action of improving the skin turnover, the effect of maintaining or enhancing the barrier function, and the action of maintaining or enhancing the hyaluronic acid production in the skin.

(Plant Extracts or Compounds Having a Skin-Turnover-Improving Action)

Examples of the above-identified plant extracts or compounds having a skin-turnover-improving action include extracts of plants such as *Sesamum indicum, Rehmannia, Amygdalus persica, Glycyrrhiza uralensis, Cactus*, wheat (*Triticum vulgare*) germ, *Fragaria vesca, Salvia officinalis, Mentha, Mentha×piperita, Houttuynia cordata, Uncaria tomentosa, Perilla frutescens* var. *crispa, Eriobotrya japonica, Camellia japonica, Ziziphus jujuba, Polygonum tinctorium* Lour., *Akebia quinata, Angelica keiskei, Thujopsis dolabrata, Malpighia emarginata, Althaea officinalis, Aloe barbadensis* Miller, *Ginkgo biloba, Phellodendron amurense, Hypericum erectum, Olea europaea* [olive], *Citrus sinensis, Matricaria recutita*, quince seed, *Citrus paradisi, Cinnamomum Loureiri* Nees, *Alpinia zerumbet, Sanguisorba officinalis, Betula platyphylla, Averrhoa carambola, Swertia* L., *Morus alba, Camellia sinensis, Syzygium aromaticum* Merr. et Perry., *Daucus carota* subsp. *sativus, Hamamelis* L., *Rosa, Rubus ellipticus, Ruscus aculeatus, Prunus domestica, Paeonia suffruticosa, Aesculus hippocastanum, Oenothera biennis, Rodgersia podophylla, Eucalyptus, Saxifraga stolonifera, Citrus junos, Coix lacryma-jobi* L. var. *mayuen* Stapf, Orchidaceae, *Citrus limon, Astragalus sinicus, Rosa canina, Rosmarinus officinalis* L., *Prunus, Fucus, Alocasia odora* (Roxb.) C Koch, *Tinospora capillipes* Gagnep., *Cnidium monnieri, Peumus boldus, Ricinus communis* L., *Sassafras albidum, Angelica keiskei, Euphorbia ebracteolata, Boswellia carterii* Birdw., *Euphorbia kansui, Impatiens balsamina* L., *Forsythia suspensa, Medicago sativa, Commiphora myrrha, Stillingia sylvatica, Lycopodium clavatum, Centipeda minima, Torilis japonica, Ficus, Magnolia liliflora Magnolia, Magnolia denudata, Betula platyphylla, Chenopodium hybridum* L., *Lonicera japonica, Gardenia jasminoides, Prunus persica*, and *Zizyphus jujuba*; and others including sea algae, Chlorellaceae, royal jelly, *citrus unshiu* peel, carnitine, nicotinic-acid amide, pyridoxine hydrochloride, hyaluronic acid, glycolic acid, citric acid, lactic acid, malic acid, tartaric acid, 2-hydroxybutyric acid, 3-hydroxybutyric acid, tartronic acid, vitamin A group, derivatives of glycyrrhizinate, allantoin, diclofenac, felbinac, ibuprofen, ketoprofen, loxoprofen, and salts thereof, one or more of, all of which can be used in combination. Among the above-identified plant extracts or compounds having a skin-turnover-improving action, preferably used are extracts of plants such as those of the family Cupressaceae including *Thujopsis dolabrata*; Ginkgoaceae including *Ginkgo biloba*; Rutaceae including *Phellodendri cortex, Citrus sinensis, Citrus×paradisi, Citrus junos*, and *Citrus limon*; Lamiaceae including *Mentha, Mentha×piperita* L., *Perilla frutescens* var. *crispa*, and *Rosmarinus officinalis* L.; Saururaceae including *Houttuynia cordata*; and Eucommiaceae including *Eucommia ulmoides*. Among which, since extracts of *Thujopsis dolabrata, Ginkgo biloba, Phellodendri cortex, Citrus sinensis, Perilla frutescens* var. *crispa, Houttuynia cordata*, and leaves of *Eucommia ulmoides*, which have later described glycation inhibitory action, are most suitably used in combination with any of L-ascorbic acid, derivatives thereof, and their salts.

The above-identified plant extracts or compounds having a skin-turnover-improving action are suitably added to one part by mass of one or more of L-ascorbic acid, derivatives thereof, and their salts, which are contained in the external dermal composition of the present invention or cosmetic lotions, face cleansing cosmetics, serums, milky lotions, or creams, in an amount of 0.00001 part by mass or more, preferably, 0.0001 to 50 parts by mass, more preferably, 0.001 to 10 parts by mass, and more preferably, 0.01 to 1 part by mass. When the composition ratio is below the above lower limit or over the above upper limit, it is not preferable because the ratio may distinctly reduce or may not exert the desired effects.

Since the L-ascorbic acid, derivatives thereof, and their salts used in the present invention exert in themselves a skin-turnover-improving action and an action of maintaining or enhancing the barrier function and the hyaluronic acid production in the skin, they can be advantageously used solely as the effective ingredient(s) of the external dermal composition of the present invention; however, the above-identified functions and effects exerted by them and their anti-wrinkle action, anti-fine-wrinkle action, as well as their anti-blemish and anti-sagging actions, can be augmented up to a level of over additive effects when the above-identified plant extracts or compounds having a skin-turnover-improving action, let alone the later described plant extracts or compounds having a glycation-inhibitory action, are incorporated in combination. Further, since the later described plant extracts or compounds do not hinder the skin-turnover-improving action, the action of maintaining or improving the skin-barrier-function and the hyaluronic acid production in the skin exerted by L-ascorbic acid, derivatives thereof, and their salts, the combination use with the above plant extracts or compounds having a skin-turnover-improving action is particularly useful in practicing the present invention.

(Plant Extracts or Compounds Having a Glycation-Inhibitory Action)

Examples of plant extracts or compounds having a glycation-inhibitory action include extracts of plants such as *Cynara scolymus, Euphrasia officinalis, Pilea mongolica, Elaeagnus umbellata, Agrimonia eupatoria, Agni* fruit, *Akebia quinata*, fruit of *Euterpe oleracea, Withania somnifera, Thujopsis dolabrata, Acacia catechu, Quercus variabilis, Gynostemma pentaphyllum, Pimpinella anisum* L., *Hamamelis virginiana, Alistin, Epimedium grandiflorum* var. *thunbergianum, Fallopia japonica* (Houtt.) Ronse Decr., *Ginkgo biloba, Pyrola japonica, Fragaria, Lilium tenuifolium* Fischer, *Gloiosiphonia capillaris, Ficus erecta*, bark of *Tabebuia spp., *Acer palmatum Lilium maculatum* Thunb., *Foeniculum vulgare*, *Hamamelis virginiana*, *Gaultheria procumbens*, *Curcuma longa* Linn, *Prunus mume*, *Quercus salicina*, *Epimedium brevicornum* Maxim, *Rosa multiflora*, *Echinacea angustifolia*, *Eleutherococcus senticosus*, *Cytisus scoparius*, *Gentianella alborosea* (Gilg) Fabris, *Sambucus nigra*, *Ilex paraguariensis*, *Borassus flabellifer*, *Phellodendron amurense*, *Coptis japonica* (Thunb.) Makino, *Silybum marianum*, *Avena sativa*, *Cardamine scutata*, *Salsola komarovii*, *Lilium rubellum*, *Lapsana apogonoides*, *Lilium lancifolium*, *Origanum vulgare*, *Citrus sinensis*, seed of *Cucurbita*, bark of *Erythroxylum catuaba*, *Lilium speciosum*, *Paullinia cupana*, *Hibiscus sabdariffa*, *Asarum nipponicum*, *Tussilago farfara*, *Platycodon grandiflorus*, *Rumex japonicus*, *Clerodendron trichotomum*, *Mallotus philippinensis*, *Lilium medeoloides* A. Gray, *Juglans*, *Vaccinium vitis-idaea* L., *Monochoria vaginalis* var. *plantaginea*, *Eisenia arborea* Areschoug, *Punica granatum*, *Ipomoea batatas*, *Smilax regelii* Killip & Morton, *Crataegus cuneata*, *Pellionia minima*, *Perilla frutescens* var. *crispa*, *Psophocarpus tetragonolobus* (L.) D.C., *Filipendula multijuga*, *Paeonia lactiflora*, *Rheum palmatum*, *Aster scaber*, *Chenopodium album*, *Aster ageratoides* ssp. *Leiophyllus*, *Plantago major*, *Centella asiatica*, *Fagopyrum esculentum*, *Lilium formosanum* A. Wallace, *Cardamine scutata*, *Davilla rugosa*, *Lilium nobilissimum* Makino, *Cordia salicifolia*, *Syzygium aromaticum* Merr. et Perry, *Cassia angustifolia*, *Centella asiatica* (L.) Urb., *Bellis perennis*, *Anethum graveolens*, *Harpogophytum procumbens*, *Farfugium japonicum* (L.) Kitam, *Lilium longiflorum*, root of *Harpogophytum procumbens*, *Rubus suavissimus* S. Lee, *Prunus persica*, *Houttuynia cordata*, *Rosa roxburghii*, leaves of *Eucommia ulmoides*, *Solanum lycopersicum*, *Potentilla tormentilla* Schrk (Rosaceae), *Rumex crispus*, *Sambucus racemosa* subsp. *sieboldiana*, *Trapaeolum majus* Linn., *Aster microcephalus* var. *ovatus*, *Mentha*, *Lilium longiflorum*, *Lespedeza* sp., *Colocasia gigantea*, *Passiflora incarnata*, *Passiflora edulis* Sims, roots of *Pfaffia*, *Artocarpus heterophyllus*, *Prunus cerasoides* var. *campanulata*, *Helianthus annuus*, *Elatostema japonicum* var. *japonicum*, *Lilium concolor*, *Lapsana apogonoides*, *Areca catechu*, *Petasites japonicus* (Siebold et Zucc.), Maxim, *Lablab purpureus* (L.) Sweet, *Cimicifuga racemosa*, *Actaea racemosa*, *Crassocephalum crepidioides*, *Actinidia polygama*, *Machilus odoratissima*, *Pinus*, *Lithocarpus edulis*, *Ilex paraguariensis*, *Lilium candidum*, *Silybum marianum*, *Staphylea bumalda*, *Stauntonia hexaphylla*, *Nemacystus decipiens*, *Salicaceae*, *Hemerocallis fulva* var. *kwanso*, *Annona montana* Macfady, *Lilium auratum*, *Ipomoea aquatica*, *Aster yomena*, seeds of *Litchi chinensis*, *Lilium regale*, *Pleioblastus linearis*, *Rubus rosaefolius*, unripe fruit of *Malus pumila*, flowers of *Tilia cordata*, *Aspalathus linearis*, *Lactuca sativa*, *Citrus limon*, *Cymbopogon citratus*, *Thymus×citriodorus*, *Aloysia citrodora*, *Melissa officinalis*, *Rosa canina*, flower buds of *Rosa damascena*, *Rosmarinus officinalis* L., *Rosa×centifolia* L., *Laurus nobilis*, *Aerides rosea*, *Haematoxylum campechianum*, *Sanguisorba officinalis*, *Astragalus sinicus*, leaves of *Diospyros kaki* Thunberg, leaves of *Glycyrrhiza uralensis*, episperms of *Glycine max*, seeds of *Oryza sativa* subsp. *javanica*, leaves of *Alpinia zerumebet*, *Lilium tenuifolium* Fischer, *Salix* sp., leaves of *Eucommia ulmoides*, and leaves of *Angelica keiskei*; extracts of sea algae such as *Gloiopeltis complanata* (Harvey) Yamada, *Gloiopeltis furcata* (Postels et Ruprecht) J. Agardh, and *Gloiopeltis tenax* (Turner) J. Agardh; extracts of raw coffee beans, lees of liquor distilled from sweet potatoes, mycelia of *Agaricus blazei*, etc.; equol; isoflavone; 1,4-anthraquinone; 1-amino-2-hydroymethyl anthraquinone; 4-aminophenol; 1,3,5-trihydroxybenzene, kojic acid; 3,4-dihydroxy-phenylacetate; caffeine acid; ifenprodil; 6-hydroxy-2,5,7,8-tetramethylchroman-2-carboxylate; 6-hydroxyindole; 7-hydroxy-4,6-dimethylphthalide; α-lipo acid, 4-hydroxychalcone; protein hydrolyzates of pearls; aminoguanidine, erythrosine sodium L-ergothioneine, resveratrol; hydroxystilbenes such as 3,3',5'5-tetrahydroxystilbene; oxindole; carnosine; salicylic acid; salsolinol hydrobromide; sinapinic acid; tocopherylnicotinate; nicotinic-acid amide; nordihydroguaiaretic acid; proanthocyanin; mannitol; hydrolyzed casein; hydrolysable tannin; catechol; chlorogenic acid and derivatives thereof such as chlorogenic acid, isochlorogenic acid, neochlorogenic acid, cryptochlorogenic acid, and feruloyl caffeoylquinic acid; and others such as leucocyanidin, prunin, procyanidol oligomer, and glycosyl rutin. Among the above ingredients, the following can be more suitably used in combination with the L-ascorbic acid, derivatives thereof, and their salts used in the present invention to effectively enhance anti-wrinkle action, anti-small wrinkle action, skin-whitening action, anti-blemish action, and anti-sagging action, exerted by the L-ascorbic acid, derivatives thereof, and their salts: Extracts of *Withania somniferous*, *Thujopsis dolabrata*, *Acacia catechu*, *Ginkgo biloba*, *Gaultheria procumbens*, *Phellodendron amurense*, *Citrus sinensis*, seed of *Cucurbita*, bark of *Erythroxylum catuaba*, *Mallotus philippinensis*, glucosyl rutin, *Vaccinium vitis-idaea* L., *Perilla frutescens* var. *crispa*, *Fagopyrum esculentum*, *Davilla rugosa*, *Houttuynia cordata*, *Elatostema japonicum* var. *japonicum*, *Crassocephalum crepidioides*, *Actinidia deliciosa*, *Pleioblastus linearis*, *Rubus croceacanthus*, unripe fruit of *Malus pumila*, leaves of *Diospyros kaki* Thunberg, leaves of *Glycyrrhiza glabra* (licorice), leaves of *Alpinia zerumbet*, extracts of *Eucommia ulmoides*, equol, isoflavone, ifenprodil, protein hydrolyzates of pearls, catechol, caffeic acid, and prunin. Among the above plant extracts having a glycation-inhibitory action, suitably used are extracts of plants of the family Cupressaceae such as *Thujopsis dolabrata*, those of the family Ginkgoaceae such as *Ginkgo biloba*, those of the family Rutaceae such as *Phellodendoron amurense* Ruprecht, *Citrus sinensis*, and *Citrus limon*, those of the family Labiatae such as *Perilla frutescens* var. *crispa* and *Rosmarinus officinalis* L., those of the family Saururaceae such as *Houttuynia cordata*, and those of the family Eucommiaceae such as *Eucommia ulmoides*; wherein extracts of *Thujopsis dolabrata*, *Ginkgo biloba*, *Phellodendoron amurense* Ruprecht, *Citrus sinensis*, *Perilla frutescens* var. *crispa*, *Houttuynia cordata*, and *Eucommia ulmoides* are most preferably used in combination with L-ascorbic acid, derivatives thereof, and their salts in the present invention. Since the combination use of these plant extracts or compounds having a glycation-inhibitory action with one or more of L-ascorbic acid, derivatives thereof, and their salts effectively inhibits the formation of AGEs, undesirable accumulation of AGEs in the skin tissue can be lowered or inhibited, and physical and physiological changes (deterioration) formed in collagen by disordered cross-links formed in collagen intra- and inter-molecularly. Accordingly, skin aging such as the reduction of wrinkles, rough skin, dullness, or the reduction of supple skin can be effectively prevented or improved. When used in combination with one or more L-ascorbic acid, derivatives thereof, and their salts, plant extracts having a glycation-inhibitory action can be advantageously masked in their intrinsic off-taste and off-flavor and improved in their storage stability by a large margin.

Examples of the amount of the above-identified plant extracts or compounds, having a glycation-inhibitory action, suitably incorporated into the external dermal composition of the present invention, or cosmetic lotions, face washes, serums, milky lotions, or creams are usually at least 0.0001 part by mass, preferably, 0.001 to 50 parts by mass, more preferably, 0.001 to 10 parts by mass, and more preferably, 0.01 to 1 part by mass to one part by mass of the total amount of one or more of L-ascorbic acid, derivatives thereof, and their salts. Any amounts below the above lower limit or over the above upper limit are not preferable because the desired effects may be distinctly lowered or even not exerted.

In the case of incorporating into the external dermal composition of the present invention the above plant extracts or compounds having a glycation-inhibitory action along with the above plant extracts or compounds having a skin-turnover-improving action usually in roughly equal amount, i.e., in a total amount of 0.01 to 1% by mass to the composition, and further with one or more of L-ascorbic acid, its derivatives, and salts thereof in a total amount of 1 to 10% by mass, d.s.b., to the total composition, the combination action exerted by the above plant extracts or compounds having a glycation-inhibitory action and those having a skin-turnover-improving action distinctly improve the skin-turnover-improving action, anti-wrinkle action, anti-fine-wrinkle action, skin-whitening action, anti-blemish action, and anti-sagging action of the composition, far exceeding the additive effects thereof.

B. Base Skin Cares

The external dermal composition of the present invention can be suitably used in the fields of cosmetics such as basic skin cares and make-up cosmetics, particularly, outstanding anti-ageing effects thereof can be expected when incorporated into basic skin cares such as cosmetic lotions, face washes, serums, milky lotions, and creams. The following are explanations of representative basic skin cares in which the external dermal composition of the present invention can be incorporated.

<Cosmetic Lotions>

As described above, the external dermal composition of the present invention has an aqueous medium as a base material that can be made into cosmetic lotions by further incorporating ethanol and humectants. Such cosmetic lotions are used for supplementing moisture and moisturizing ingredients to the stratum corneum in the skin and to support the physiological functions in the skin. Concrete examples of such cosmetic lotions can be listed as cosmetic lotions for washing, astringent cosmetic lotions, softening cosmetic lotions, and multi-layered cosmetic lotions, as well as skin lotions, body lotions, hand lotions, emollient lotions, etc.

(Humectants)

The following can be listed as humectants usable in the cosmetic lotion according to the present invention: Polyalcohols such as glycerin, ethylene glycol, propylene glycol, 1,3-butylene glycol, 3-methyl-1,3-butanediol, 1,3-propanediol, 2-methyl-1,3-propanediol, trimethylolpropane, pentaerythritol, diglycerine, polyglycerine, diethylene glycol, triethylene glycol, polyethylene glycol, dipropylene glycol, polypropylene glycol, 1,2-pentanediol, 1,2-hexanediol, 1,2-heptanediol, isoprene glycol, isopentyldiol, hexylene glycol, triglycerine, 2-methacryloyloxyethyl phosphorylcholine, tetrahydrofurfuryl alcohol, polyoxyethylene (POE) tetrahydrofurfuryl alcohol, polyoxypropylene (POP) butyl ether, POP•POE-butyl ether, tripolyoxypropylene glycerin ether, POP-glycerin ether, POP-glycerin ether phosphate, POP•POE pentaerythritolether, ethylene glycol•propyleneglycol copolymer, phytantriol, and erythrulose; glycol alkyl ethers such as ethyleneglycolmonomethylether, ethyleneglycolmonophenylether, ethyleneglycolmonohexylether, diethyleneglyocolmonomethylether, triethyleneglyocolmonoethylether, monooleyl glyceryl ether, diethyleneglycolmonoethylether, ethyleneglycolmonoethylether, ethyleneglycolmonobutylether, and diethyleneglycoldibutylether; sugar alcohols such as sorbitol, xylitol, erythritol, mannitol, maltitol, maltotriitol, maltotetraitol, and hydrogenated products of starch hydrolyzates; saccharides such as sucrose, rhamnose, glucose, fructose, galactose, mannose, threose, xylose, arabinose, fucose, ribose, deoxyribose, maltose, maltotriose, maltotetraose, trehalose, lactose, raffinose, glucuronic acid, glucuronic acid, saccharide derivatives of trehalose (including glucosyl trehalose, maltosyltrehalose, maltotriosyl trehalose, and maltotetraosyl trehalose), sulfated trehalose, dextrin, cyclodextrin, cyclotetrasaccharide (cyclonigerosylnigerose) having a structure of cyclo{→6)-α-D-glucopyranosyl-(1→3)-α-D-glucopyranosyl-(1→6)-α-D-glucopyranosyl-(1→3)-α-D-glucopyranosyl-(1→} disclosed in International Patent Application No. WO 02/10361, cyclotetrasaccharide (cyclomaltosylmaltose) having a structure of cyclo{→6)-α-D-glucopyranosyl-(1→4)-α-D-glucopyranosyl-(1→6)-α-D-glucopyranosyl-(1→4)-α-D-glucopyranosyl-(1→} disclosed in Japanese Patent Kokai No. 2005-95148, pullulan, isomerized sugars, and xylitylglucoside; amino acids such as valine, leucine, isoleucine, threonine, methionine, phenylalanine, tryptophan, lysine, glycine, alanine, asparagine, glutamine, serine, cysteine, cystine, tyrosine, proline, hydroxyproline, asparaginic acid, glutamic acid, sodium glutamate, hydroxylysine, arginine, ornithine, histidine, and pyrrolidone carbonate; NMF ingredients (natural moisturizing ingredients) such as sodium lactate, uric acid, and sodium pyrrolidone carbonate; mucopolysaccharides and their hydrolyzates such as glycogen, dextran, locust bean gum, xyloglucan, quince seed, carrageenan, pectin, mannan, curdlan, succinoglucan, galactan, arabinogalactan, dermatan sulfate, keratan sulfate, chondroitin, chondroitin sulfate, mucoitinsulfuric acid, keratosulfate, chitin, chitosan, heparin, heparan, and hyaluronic acid; protein and peptides and their hydrolyzates such as soybean protein degradation peptides, wheat protein degradation peptides, hydrolyzed wheat proteins, hydrolyzed casein peptides, acyl peptides including palmitoyloligopeptide; silylated peptides, conchiolin degradation peptides, hydrolyzed conchiolin, proteins and peptides such as silk and collagen, hydrolyzates of proteins and peptides such as silk and collagen; water-soluble high molecular substances such as hydrolyzed hyaluronic acid and hydrolyzed eggshell membrane, as well as salts thereof; lecithin derived from soybeans and egg yolks; phosphatides and sphingolipids such as phosphatidyl glycerol, phosphatidyl inositol, phosphatidyl serine, phosphatidyl ethanolamine, phosphatidic acid, and sphingomyelin; oils and fats such as *Olea europaea* [olive] oil, jojoba oil, and squalane; silicons such as dimethylpolysiloxane and methylphenylsiloxane; culture supernatants of lactic acid bacteria, bifid bacteria, etc.; and others such as royal jelly extract, yeast extract, eggshell membrane protein, bovine submaxillary gland mucin, hypotaurine, galactoarabinan, sesame lignan glycosides, albumin, milk whey, choline chloride, phosphorylcholine, placenta extract, *coix* seed extract, *Paeonia Suffruticosa* root extract, seaweed extract, *Gentiana lutea* extract, *Saxifraga stolonifera* extract, *Perilla frutescens* var. *crispa* extract, hydrolyzed *Oryza sativa* [rice] bran extract, enzymatic decomposition product of prune, trimethylglycine, N-methyl-L-serine, nicotinic-acid amide, *Scutellaria baicalensis* extract, *Camellia sinensis* var. *sinensis* extract, *Centella asiatica* extract, *Morus bombycis*

Koidz. extract, polysaccharides produced from *Alcaligenes*, hydrolyzed *Brassica alba* extract, sodium acetylhyaluronate, *Althea* extract, *Japanese angelica* extract, *Aloe vera* extract, *Rosa roxburghii roxburghii* extract, deoxyribonucleic acid sodium salt, *Melothria* extract, *Daucus carota* L. extract, *Houttuynia cordata* extract, oolong tea extract, wheat germ extract, xylobiose mixture, *Akebiae caulis* extract, *Phellodendoron amurense* Ruprecht, *Hypericum erectum* extract, *Pueraria lobata* Ohwi, whey, *Prunus* leaf extract, *Paeonia* extract, great burnet extract, *Malpighia glabra* extract, *Iris domestica* extract, *Leontopodium alpinum* extract, *Prunus dulcis* extract, glucosylhesperidine, yellow Himalayan raspberry root extract, peppermint extract, *Rehmannia* extract, mevalonolactone, *Angelica keiskei* extract, *Ginkgo biloba* extract, *Equisetum arvense* extract, hydrolyzed *Glycine max* (L.) Merrill extract, *Thymus* extract, *Coptis* extract, adenosine monophosphate, adenosine triphosphate disodium, dl-α-tocopherol, DL-sodium malate, γ-amino-β-hydroxybutyric acid, *Thujopsis dolabrata* extract, *Asparagus officinalis* extract, *Aspalathus linearis* extract, *Persea americana* extract, *Prunus armeniaca* juice, *Mytilus* glycogen, inositol, *Polygonum bistorta* L. extract, *Urtica thunbergiana* extract, turmeric extract, uva ursi fluidextract, *Rosa multiflora* fruit extract, *Echinacea purpurea* leaf extract, ethylglucoside, *Lagerstroemia speciosa* extract, *Panax ginseng* extract, *Ononis* extract, *Olea europaea* leaf extract, *Diospyros kaki* Thunberg extract, *Typha latifolia* L. extract, *Myrciaria dubia* extract, *Myrciaria dubia* seed extract, carrot extract, *Rubus* extract, *Actinidia deliciosa* extract, *Psidium guajava* L. extract, *Gardenia jasminoides* extract, *Sasa veitchii* extract, *Sophora flavescens* extract, glycolic acid, grapefruit extract, *Clematis* hybrids extract, *chlorella* extract, *Aloe barbadensis* Miller extract, *Geranium thunbergii* extract, coffee extract, succinic acid bis[1-[2-(2-hydroxyethoxy)ethyl]guanidine-1-yl]ester, hydrolyzed solution of rice bran extract, collagen-tripeptide, extract of root and stem of *Asarum heterotropoides* var. *mandshuricum*, succinyl aterocollagen, *Crataegus cuneata* extract, *Cassia mimosoides* L. extract, cyanocobalamin, seagrass extract, *Tilia japonica* extract, condensed solution of dimethylsilanol and hyarunonic acid, *Filipendula* extract, *Acoraceae* root extract, *Betula platyphylla* extract, silk extract, silk powder, *Lonicera japonica* extract, *Averrhoa carambola* leaf extract, strawberry fruit juice, *Hedera helix* L. extract, *Crataegus laevigata* extract, *Inula britannica* extract, *Swertia japonica* extract, *Morus alba* L. extract, sorbitol culture polysaccharide solution, soybean extract, *Ziziphus jujuba* extract, *Camellia* extract, *Bellis perennis* extract, *Terminalia* extract, *Rubus suavissimus* S. Lee extract, *Prunus persica* extract, *Picea jezoensis* var. *hondoensis* extract, *Zea mays* extract, tomato fruit juice, *Rosa multiflora* extract, *Hibiscus sabdariffa* extract, *Lupinus* extract, malt root extract, *Alchemilla japonica* extract, lactic acid bacteria fermented solution of *Nelumbo nucifera* seed, *Petroselinum neapolitanum* extract, *Rosa rugosa* extract, *Hamamelis japonica* extract, rose extract, *Parietaria* extract, *Pancratium maritimum* extract, *Iris domestica* extract, *Eriobotrya japonica* leaf extract, phytoglycogen, *Aesculus hippocastanum* extract, *Impatiens balsamina* extract, sodium polyaspartate solution, *Majoranahortensis Moench* extract, *Lilium* extract, *Persicaria tinctoria* extract with water, *Aesculus hippocastanum* extract, elastin, natural ceramide (types 1, 2, 3, 4, 5, and 6), hydroxyceramide, pseudoceramide, glycosphingolipid, ceramides including ceramide and extracts containing ceramide saccharide, deep seawater, alkaline simple hot spring, polyoxyethylene methyl glucoside, sodium dl-pyrrolidone carboxylate, L-oxyproline, acetylglucosamine, and taurine.

Particularly, the following humectants are preferably used in cosmetic lotions incorporated with the external dermal composition of the present invention because they have an improved moisturizing effect and more effectively improve rough skin when used in combination with one or more of L-ascorbic acid, derivatives thereof, and salts thereof; glycerin, ethylene glycol, propylene glycol, 1,3-butylene glycol, 3-methyl-1,3-butanediolo, pentaerythritol, diglycerine, polyglycerine, diethylene glycol, triethylene glycol, polyethylene glycol, dipropylene glycol, trehalose, ceramides and the like, 2-methacryloyloxyethyl phosphorylcholine, hyaruronic acid, condroitin sulfate, hydrolyzed hyaluronic acid, yeast extract, *Coix lacryma-jobi* var. *ma-yuen* extract, *Paeonia suffruticosa* extract, seaweed extract, *Gentiana lutea* extract, trimethylglycine, N-methyl-L-serine, nicotinic-acid amide, and royal jelly extract, one or more of which can be preferably used as a humectant(s).

The above humectants can be respectively incorporated into the cosmetic lotion of the present invention in an amount of at least 0.0001% by mass, preferably, 0.001 to 50% by mass, more preferably, 0.01 to 25% by mass, and more preferably, 0.1 to 10% by mass to the mass of the cosmetic lotion.

To the cosmetic lotion of the present invention can be incorporated the following: One or more astringents, keratinous-layer-softening agents, emollients, and surfactants.

<Astringents>

Examples of the astringents usable in the present invention include: Citric acid, tannic acid, acetoxy propionic acid, isovaleric acid, aminovaleric acid, ethoxy acetic acid, ethoxypropionate, isoaminovaleric acid, epoxyoleic acid, elaidic acid, aminobutyric acid, erucic acid, oxaloacetic acid, formic acid, icosanoic acid, glucuronic acid, iduronic acid, crotonic acid, chloroisocrotonic acid, isocrotonic acid, acetic acid, dihydrolipoic acid, acidum tartaricum, ethyl crotonic acid, diphenylacetic acid, dimethoxyphthalic acid, ethyl hydroxybutyric acid, succinamic acid, stearic acid, stealoric acid, sorbic acid, tiglic acid, thyroxin, decanoic acid, tropic acid, lactic acid, hydroxyisobutyric acid, hydroxyvaleric acid, pyruvic acid, butyl acetate, butylhydroperoxide, brassidic acid, propiolic acid, propionic acid, bromo isovaleric acid, bromoisobutyric acid, bromopropionic acid, hexanoic acid, hexenoic acid, petroselinic acid, heptadecanoic acid, heptanoic acid, maleanilic acid, maleamic acid, mycolic acid, myristic acid, methacrylic acid, methylvaleric acid, methylthioacetic acid, methyl butyrate, mevalonic acid, melissic acid, mercaptoacetic acid, iodoacetic acid, lauric acid, ricinelaidic acid, ricinoleic acid, linoleic acid, linolenic acid, aconitic acid, oxalosuccinic acid, oxoglutaric acid, adipic acid, calcein, carboxyphenylacetic acid, acetoxysuccinic acid, carbocinchomeronic acid, camphoronic acid, isocamphoronic acid, glutaconic acid, glutaric acid, isocitric acid, crocetin, succinic acid, phthalic acid, fumaric acid, isocinchomeronic acid, diethylenetriamine pentaacetate, isophthalic acid, citramalic acid, dinicotinic acid, itaconic acid, dibromosuccinic acid, dichlorosuccinic acid, ethylmalonic acid, dimethylsuccinic acid, oxalic acid, cinchomeronic acid, hemimellitic acid, pelargonic acid, berberonic acid, benzenehexacarboxylic acid, benzenepentacarboxylic acid, maleic acid, malonic acid, mesaconic acid, mesotartaric acid, mesoxalic acid, methylisophthalic acid, methylsuccinic acid, methylmalonic acid, mercaptosuccinic acid, mellophanic acid, peroxyphthalic acid, malic acid, lutidinic acid, leukotriene bromo anthranilic acid, aminocinnamic acid, isopropyl cinnamic acid, oxanilic acid, arecaidine, caboxylic cinnamic acid, cinnamic acid, gallotannic acid, tranexamic acid, nitrocinnamic acid, hydroxycinnamic acid, methoxycinnamic acid, hydroxyhydrocinnamic acid, phenylcinnamic acid, ellagic acid, orotic aciduria, camphanic acid, quinic acid, hydroxyproline, etiocholanic acid, chaulmoogric acid, carnosine, carbazole acetic acid, quinolinecarboxylic acid, quinolinic acid, quinoline dicarboxylic acid, coumaric acid, chlorophenoxyacetic acid, chenodeoxycholic acid, cholanic acid, cholic acid, santoninic acid, dihydro ortho acid, succinuric acid, thiophencarboxylic acid, tetrahydrofolic acid, dehydrocholic acid, terpenylic acid, hydroxypyrone carboxylic acid, hydroxypyrone dicarboxylic acid, hydroxyphenylacetic acid, hydroxyphenylpropionic acid, phenyldicarboxylic acid, homogentisic acid, mandelic acid, muricholic acid, methyldopa, methylphenylacetic acid, methylfurancarboxylic acid, methyl red, mefenamic acid, lysergic acid, lithocholic acid, lipoic acid, reserpinic acid, retinoic acid, levopimaric acid, glycolic acid, salicylic acid, paraphenol zinc phenolsulfonate; extracts of plants such as *Althea officinalis*, *Arnica montana*, *Polygonum bistorta*, *Iris* spp., *Foeniculum vulgare*, *Lagerstroemia speciosa*, *Citrus sinensis*, *Rubus* L., *Psidium guajava* L., *Ribes nigrum*, *Geranium thunbergii*, *Crataegus cuneata*, *Filipendula multijuga*, *Paeonia lactiflora*, *Betula platyphylla* var. *japonica*, *Lonicera japonica*, *Equisetum arvense*, *Hedera helix*, *Thymus vulgaris*, *Camellia sinensis*, *Petroselinum crispum*, *Hamamelis virginiana*, *Vitis* spp., *Centaurea cyanus*, *Citrus limon*, *Astragalus sinicus*, *Sanguisorba officinalis*, *Cinchona succirubra*, *Salvia* L., *Tilia miqueliana*, *Panax ginseng* [Asian ginseng], *Juniperus communis*, *Rosmarinus officinalis* L., *Hypericum erectum*, *Ginkgo biloba*, *Melissa officinalis*, *Ononis spinosa* Linn, *Aesculus hippocastanum*, *Swertia japonica*, *Allium sativum*, *Matricaria recutita*, *Thymus vulgaris*, *Mentha arvensis* var. *piperascens*, *Urtica thunbergiana*, *Capsicum annuum* L., *Zingiber officinale*, *Humulus lupulus*, *Aesculus hippocastanum*, *Lavandula angustifolia*, *Daucus carota* subsp. *sativus*, *Brassica juncea*, *Cinnamomum cassia* Bl., *Pinus*, *Cnidium officinale* Makino, *Sambucus sieboldiana*, *Ostericum sieboldii*, *Scopolia japonica*, *Paeonia suffruticosa*, *Myrica rubra*, *Houttuynia cordata*, *Nuphar japonicum*, *Diospyros* spp., *Calendula officinalis*, *Papaver rhoeas* L., *Gentiana scabra* var. *buergeri*, *Glehnia littoralis*, *Citrus aurantium*, *Citrus junos*, *Acorus calamus*, *Citrus natsudaidai*, *Melilotus officinalis*, *Zanthoxylum piperitum*, *Eucalyptus globulus*, *Artemisia indica* var. *maximowiczii*, *Rabdosia japonica*, *Oryza sativa*, *Sophora flavescens*, *Zingiber officinale*, *Eugenia caryophyllata*, leaf of *Juglans*, *Scutellaria baicalensis*, *Salvia officinalis*, *Rosmarinus officinalis* L., *Polygonum multiflorum* Thunb., *Coptis japonica* (Thunb.) Makino, *Phellodendron amurense* Rupr., *Scutellaria baicalensis* Georgi, *Houttuynia cordata*, *Aurantii nobilis pericarpium*, *Daucus carota* subsp. *sativus*, *Juncus effusus* L. var *decipiens* Buch, and *Alisma rhizome*; plant extracts of tannin and tar of *Betula platyphylla*; propolis, royal jelly, yeast extract, *tuberosa* polysaccharide solution, oolong tea, alum, zinc chloride, zinc sulfate, aluminum sulfate, aluminum chloride, aluminum chloride hydroxide allantoin, dihydroxyaluminum allantoin, aluminum hydroxychloride, zinc oxide, zinc sulfide, zinc sulfocarbolate, sodium sulfocarbolate, and organic composites of aluminum or zirconium.

Usually, the above astringents can be respectively incorporated into the cosmetic lotion of the present invention in an amount of at least 0.0001% by mass, preferably, 0.001 to 50 parts by mass, more preferably, 0.01 to 25% by mass, and more preferably, 0.1 to 10% by mass.

Particularly, in the case of cosmetic lotions into which the external dermal composition of the present invention is incorporated, preferably used are the following one or more astringents selected from acids such as citric acid, succinic acid, acidum tartaricum, retinoic acid, malic acid, retinol, zinc chloride, aluminum compounds such as aluminum powder and aluminum sulfate; alum; and others such as denatured alcohol, ethanol, *althea* extract, *arnica* extract, *Polygonum* extract, *Urtica dioica* L. extract, *Iris sanguinea* Hornem extract, *Foeniculum vulgare* extract, oolong tea extract, ethanol, *Lagerstroemia speciosa* extract, *Hypericum erectum*, *Citrus aurantium* Dulsis [Orange] flower water, orange juice, *Artemisia capillaris* extract, strawberry extract, *Psidium guajava* L. extract, *Ribes nigrum* fruit extract, geraniol, *Geranium thunbergii* extract, *Crataegus cuneata* extract, *Filipendula multijuga* extract, *Paeonia lactiflora* extract, *Betula platyphylla* extract, *Lonicera japonica* extract, *Equisetum arvense* extract, *Hedera helix* L., *Crataegus laevigata* extract, *Thymus* extract, *Camellia sinensis* extract, *Houttuynia cordata* extract, *Petroselinum neapolitanum* extract, *Hamamelis virginiana* extract, *Vitis* spp. leaf extract, *Pinus* extract, *Melissa Officinalis* leaf extract, *Centaurea cyanus* extract, *Artemisia indica* var. *maximowiczii* extract, *Citrus limon* juice, *Astragalus sinicus* extract, and *Sanguisorba officinalis* extract.

Examples of the keratinous-layer-softening agents, preferably used are the following one or more ingredients selected from ethanol, isopropyl alcohol, propanol, butanol, polyethylene glycol, benzyl alcohol, phenylethyl alcohol, propylene carbonate, hexyl dodecanol, dimethylsulfoxide, dimethylacetamide, dimethylformamide, triethanolamine, diisopropyl adipate, ethyl laureate, lanolin, dialkylolamides of fatty acids, urea, sulfur, resorcin, phytic acid, lactic acid, lactate, glycolic acid, sodium hydroxide, etc. Particularly, in the case of cosmetic lotions into which the external dermal composition of the present invention is incorporated, one or more of ingredients selected from urea, sulfur, ethanol, lactic acid, glycolic acid, salicylic acid, and sodium sulfate, which are superior in keratinous-layer-softening effect.

(Emollients)

Oily ingredients, which are close to sebum, are mainly preferable as the emollients [softeners] and exemplified as follows: Plant and animal oils and fats such as *Cannabis* seed oil, *Astrocaryum yauaperyense* fat, *Brassica campestris* seed oil, African Mango kernel oil, *Prunus armeniaca* kernel oil, *Camelina* seed oil, *Argania spinosa* kernel oil, *Prunus armeniaca* kernel oil, *Hippophae rhamnoides* oil, *Echium plantagineum* seed oil, emu oil, orange roughy oil, canola oil, *Torreya nucifera* seed oil, *Garcinia indica* Choisy seed oil, *Carum carvi* seed oil, *Prunus armeniaca* L. var *anus* Maxim oil, *Aleurites moluccana* oil, *Crambe abyssinica* seed oil containing erucic acid, *Vaccinium macrocarpon* seed oil, walnut seed oil, *Ribes nigrum* seed oil, *Vaccinium vitis-idaea* L. seed oil, rice germ oil, *Pinus parviflora* seed oil, *Camellia sasanqua* oil, *Shorea* seed oil, oxidized corn oil, shea oil and fat, *Shorea stenoptera* (seed) butler, *Lupinus albus* seed oil, hydrogenated avocado oil, hydrogenated olive oil, hydrogenated beef tallow, hydrogenated soybean oil, hydrogenated jojoba oil, hydrogenated vegetable oil, hydrogenated palm kernel oil, hydrogenated palm oil, castor oil hydrogenated, hydrogenated jojoba oil, hydrogenated vegetable oil, hydrogenated coconut oil, *Sclerocarya birrea* seed oil, *Struthio camelus* oil, *Passiflorae incarnata* L. seed oil, *Camellia sinensis* oil, camellia oil, *Vaccinium oxycoccos* seed oil, *Theobroma grandiflorum* seed fat, lard, creams, *Coix lachryma-jobi* L. var. *ma-yuen* Stapf Coix oil, babassu oil, peanut oil, *Pistachio* seed oil,

*Hippophae rhamnoides* oil, sunflower seed oil, *Vaccinium myrtillus* L. seed oil, grape seed oil, partially hydrogenated *perilla* oil, partially hydrogenated hourse oil, prune seed oil, broccoli seed oil, *Luffa cylindrica* seed oil, *Cucurbita pepo Linnaeus* seed oil, *Haematococcus pluvialis* oil, *Rubus chamaemorus* seed oil, pine seed oil, *Mangifera indica* seed fat, *Mangifera indica* seed oil, mink oil, *Melia azadirachta* seed oil, peach kernel oil, begetable oil, *Camellia oleifera* oil, *Rubus idaeus* seed oil, apple seed oil, *Borago officinalis* seed oil, rose hip oil, seed oil of *Moringa oleifera* Lam., *Macadamia integrifolia* oil, castor oil, olive oil, almond oil, cacao oil, *camellia* oil, coconut oil, palm oil, tallow, jojoba oil, grape seed oil, avocado oil, safflower oil, sesame oil, *Camellia sinensis* oil, evening primrose oil, wheat germ oil, hazelnut oil, *Limnanthes alba* oil, *Prumus persica* kernel oil, peppermint oil, *Melaleuca alternifolia* oil, corn oil, canola oil, sunflower oil, linseed oil, cotton oil, soybean oil, peanut oil, rice bran oil, cacao oil, shea oil, fennel oil, *perilla* oil, chamomile oil, carrot oil, cucumber oil, egg yolk oil, beef fat, hourse fat, fish oil, turtle oil, and orange roughy oil; waxes such as lacquer-tree fruit rind wax, *Jasminum officinale* flower wax, orange fruit rind wax, orange flower wax, hydrpogenated jojoba oil ester, carnauba wax, candelilla wax, *Narcissus poeticus* L. flower wax, rice bran wax, *Myrica rubra* f. alba fruit wax, sweet *acacia* flower wax, *Polianthes tuberosa* flower wax, beeswax, spermaceti, orange roughy oil, lanolin, rice wax, montan wax, and ozokerite; hydrocarbons such as isoeicosane, isododecane, isohexadecane, diethylhexylcyclohexane, pentahydrosqualane, mineral oils, petrolatum, polyisobutene, hydrogenated polyisobutene, polybutene, squalane, squalene, microcrystalline wax, ceresin wax, paraffin wax, vaseline, ozokerite, α-olefin oligomer, and tetradecene; natural and synthetic fatty acids and salts thereof such as isomerized linoleic acid, tallowate, fatty acids (C14-28), fatty acids (C20-40), hydrogenated coconut fatty acid, palm kernel fatty acid, 10-hydroxydecanoic acid, branched fatty acids (C14-28), branched fatty acids (C21-31), behenic acid, capric acid, myristic acid, palmitic acid, stearic acid, behenic acid, lanolin fatty acid, linoleic acid, linolenic acid, lauric acid, oleic acid, isostearic acid, undecylenic acid, 1,2-hydroxystearic acid, palmitooleic acid, erucic acid, docosahexaenoic acid, eicosapentaenoic acid, isohexadecenoic acid, anteisoheneicosanoic acid, isononanoic acid, and 2-ethylhexanoic acid; natural and synthetic higher alcohols such as C12-16 alcohols, C14-22 alcohols, C20-22 alcohols, C20-40 alcohols, C30-50 alcohols, *brassica* rapeseed sterol, isocetyl alcohol, isopropanol, caprylyl glycol, rice bran sterol, hydrogenated rapeseed alcohol, cetanol, stearyl alcohol, hexyl decanol, octyl dodecanol, lauryl alcohol, capryl alcohol, myristyl alcohol, oleyl alcohol, cetostearyl alcohol, arachyl alcohol, behenyl alcohol, jojoba alcohol, chimyl alcohol, selachyl alcohol, batyl alcohol, isostearyl alcohol, cetyl alcohol, cholesterol, phytosterol, lanolin alcohol, hydrogenated lanolin alcohol, palmityl alcohol, and 2-decyltradecinol; esters such as isopropyl C12-15-pareth-9 carboxylate, octyldodecyl pyrrolidone carboxylic acid, menthyl pyrrolidone carboxylic acid, lauryl pyrrolidone carboxylic acid, PEG-2 isosedes-7 carboxylic acid cetyl ester, di-PPG-3 myristyl ether adipate, di-PPG-2 myreth-10 adipate, diisopropyl adipate, diheptylundecyl adipate, ethyl avocadate, butyl avocadate, methyl gluceth-20 benzoate, ethyl isostearate, (isostearic acid/succinic acid) castor oil, hydrogenated castor oil isostearate, batyl isostearate, hexyldecyl isostearate, (isostearic acid/bees wax/succinic acid) castor oil, isodecyl isononanoate, isotridecyl isononanoate, isononyl isononanoate, octyl isononanoate, cetearyl isononanoate, sucrose acetate isobutyrate, caprylyl eicosenoate, butyl ethyl propanediol ethylhexanoate, octyldodecyl erucate, oleyl erucate, alkyl octanoate (C14, C16, and C18), (octanoicacid/stearicacid/adipic acid) glyceryl, cetyl octanoate, stearyl octanoate, cetearyl ethylhexanoate, hexyldecyl ethylhexanoate, ethyl olivate, oleyl oleate, caprylic/capric glycerides, caprylic/capric/coconut fatty acid glyceride, caprylic/capric/succinic triglyceride, cetyl caprate, triisostearyl citrate, triisooctyldodecyl citrate, citric/lactic/linoleic/oleic tetraglyceride, isostearyldiglyceryl succinate, diethoxylethyl succinate, dioctyl succinate, phytosteryl rice bran oil fatty acid, cetyl acetate, farnesyl acetate, lanolin alcohol acetate, linalyl acetate, propylene glycol diisostearate, dimer-dilinoleyl diisostearate, dimer-dilinoleyl diisostearate, neopentyl glycol diisostearate, neopentyl glycol diethylhexanoate, PEG-18 castor oil dioleate, di-(caprylic acid/capric acid) butylene glycol, isosorbide dicaprylate, di-(caprylic acid/capric acid) polyethylene glycol, dicocoyl pentaerythrityl distearyl citrate, polyethylene glycol distearate, PG-20 methylglucose distearate, pentaerythrityl distearate, diethyl pentanediol dineopentanoate, methyl pentanediol dineopentanoate, polyethylene glycol dinonanoate, C10-30 cholesterol/lanosterol esters, C12- to C-18 cetyl esters, glycol dilaurate, diisopropyl dimer dilinoleate, pentaerythrityl hydrogenated rodinate, methyl hydrogenated rosinate, glyceryl diisostearate/hydrogenated rosinate, ethylhexyl stearate, isocetyl stearoyl oxystearate, octyldodecyl stearoyl oxystearate, dibutyloctyl sebacate, octyldodecyl/PPG-3 myristyl ether dimer dilinoreate, di-(isostearyl/phytophytoryl) dimer dilinoleate, dicetearyl dimer dilinoleate, hydrogenated castor oil dimer dilinoleate, stearyl/PPG-3 myristyl ether dimer dilinoleate, dimer dilinoleyl dimer dilinoleate, bis-behenyl/isostearyl/phytosteryl dimer dilinoleyl dimer dilinoleate, phyto phytosteryl/isostearyl/cetyl/stearyl/behenyl dimer dilinoleate, dimer dilinoleyl hydrogenated rosin condensate, C14-15 dialkyl carbonates, diethylhexyl carbonate, dicaprylyl carbonate, pentaerythrityl tetraisostearate, pentaerythrityl tetraoctanoate, polyglyceryl-10 dodecacaprylate/caprate, diisocetyl dodecanedioate, dioctyldodecyl dodecanedioate, triisostearate, erythrityl triethylhexanoate, ditrimethylolpropane triethylhexanoate, triethylhexanoin (trioctanoin), trimethylolpropane tiethylhexylhexanoate trimethylolpropane, tricaprylin, caprylic/capric triglyceride, caprylic/capric/stearic triglyceride, caprylic/capric/myristic/stearic triglyceride, C8-12 acid-triglycerides, tristearin, tripalmitin, tripalmitolein, trihydroxystearin, tribehenate, dipentaerythrityl tri-polyhydroxystearate, trimyristin, C12-15 alkyl lactates, ethyl lactate, octyldodecyl lactate, butyl lactate, menthyl lactate, isodecyl neopentanoate, myristyl neopentanoate, nonanoic acid octyl ester, nonanoic acid cholesterol ester, ethylhexyl palmitate, cetyl palmitate, bis-diglyceryl polyacyladipate-1, bis-diglyceryl polyacyladipate-2, dipentaerythrityl pentahydroxystearate/pentaisostearate, ethylhexyl dihydroxystearate, octyl hydroxystearate, hydrogenated castor oil hydroxystearate, dipentaerythrityl hexahydroxystearate/stearate/rosinate, phytosteryl hydroxystearate, PPG-6 castorate, methyl ricinoleate, myristyl propionate, C10-40 isoalkyl acid cholesterol esters, dipentaerythrityl hexahydroxystearate, dipentaerythrityl hexahydroxystearate/hexastearate/hexarosinate, stearyl heptanoate, glyceryl behenate/eicosadioate, jojoba esters, isopropyl jojobate, ethyl macadamiate, cholesteryl macadamiate, phytosteryl macadamiate, dioctyl maleate, diethylhexyl syringylidenemalonate, heyldecyl myristoyl methylaminopropionate, citronellyl methylcrotonate, medowfoam estolide, octyldodecyl meadowfoamate, glyceryl cocoate/citrate/lactate, decyl cocoate, cholesteryl butyrate, dihydrocholesteryl butyrate, octyldodecyl lanolate, cholesteryl lanolate, octyldodecyl ricinoleate, diethylhexyl malate, trioleyl phosphate, tricetyl phosphate, glyceryl tri-2-ethylhexanoate, cetyl 2-ethylhexanoate, neopentyl glycol di-2-ethylhexanoatte, isopropyl myristate, butyl myristate, isopropyl palmitate, ethyl stearate, octyl palmitate, isocetyl isostearate, butyl stearate, ethyl linoleate, isopropyl linoleate, ethyl oleate, isocetyl myristate, isostearylmyristate, isostearyl palmitate, octyldodecyl myristate, diethyl sebacate, diisopropyl adipate, isoalkyl neopentanoate, caprylic/capric triglyceride, trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, glyceryl trimyristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol diloleate, propylene glycol dioleate, propylene glycol dicaprate, propylene glycol dicaprylate/dicaprate, caprylic/capric triglyceride, propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neodecanoate, octyldodecyl neopentanoate, isostearyl octanoate, hexyldecyl neodecane, hexyldecyl neodecanoate, octyldodecyl neodecanoate, isostearyl isostearate, octyldecyl isostearate, polyglyceryl oleate ester, polyglyceryl isostearate ester, dipropyl carbonate, C12- to C18-dialkyl-carbonates, triisocetyl citrate, triisoarachidyl citrate, triisooctyl citrate, lauryl lactate, myristyl lactate, cetyl lactate, octyldecyl lactate, lanolin lactate, triethyl citrate, acetyltriethyl citrate, acetyltributyl citrate, trioctyl citrate, diisostearyl malate, 2-ethylhexyl hydroxystearate, 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, hexyldecyl dimethyloctanoate, and isopropyl lanolate; lanolins such as liquid lanolin, hydrogenated lanolin, adsorption refined lanolin, lanolin acetate, acetylated lanolin, hydroxylanolin, polyoxyethylene lanolin, hard lanolin fatty acid, and cetyl•lanolyl acetate; sphingophospholipids such as lecithin, phosphatidylcholine, phosphatidylethanolamine, phosphatidylserine, phosphatidylglycerol, phosphatidylinositol, and sphingomyelin; phospholipids such as phosphatidic acid and lysolecithin; phospholipid derivatives such as hydrogenated soybean phospholipid, partially hydrogenated soybean phospholipid, hydrogenated egg yolk-phospholipid, and partially hydrogenated egg yolk-phospholipids; sterols such as dihydrocholesterol, lanosterol, dihydrolanosterol, and cholic acid; silicon-containing oil agents such as methylphenyl polysiloxane, methylhydrogen polysiloxane, octamethylcyclotetrasiloxane, stearoxysilicone, decamethylcyclopentasiloxane, and dodecamethyl cyclohexasiloxane; sapogenins; saponins; and fluorine-containing oil agents such as perfluoropolyether, perfluorodecalin, and perfluorooctane.

Particularly, in the case of cosmetic lotions in which the external dermal composition of the present invention is incorporated, the following one or more emollient agents, which are advantageous in emollient effect and widely used in a cosmetic field, can be preferably used in combination; cetanol, lauryl alcohol, cetostearyl alcohol, stearyl alcohol, oleyl alcohol, behenyl alcohol, lanolin alcohol, hydrogenated lanolin alcohol, hexyldecanol, octyldodecanol, squalane, plant squalane, cetyl 2-ethylhexanoate, α-olefin oligomer, isotridecyl isononanoate, isononyl isononanoate, cetearyl isononanoate, ethyl oleate, oleyl oleate, ethylhexyl palmitate, caprylyl glycol, and hydrogenated soybean phospholipid.

<Surfactants>

Examples of the surfactants are as follows: Sorbitan monolaurate, coconut oil fatty acid sorbitan, sorbitan distearate, sorbitan monostearate, sorbitan tristearate, sorbitan monoisostearate, sorbitan monooleate, sorbitan trioleate, sorbitan fatty acid ester, sorbitan monopalmitate, sorbitan sesquioleate, sorbitan sesquistearate, polyoxyethylene sorbitan monolaurate, polyoxyethylene sorbitan monostearate, ethylene glycol monostearate, ethylene glycol distearate, diethylene glycol distearate, ethylene glycol fatty acid ester, glyceride monostearate, glyceride distearate, glyceryl isostearate, polyoxyethylene glyceryl isostearate, polyoxyethylene glyceryl triisostearate, diglyceryl isostearate, glyceryl diisostearate, glyceryl triisostearate, diglyceryl triisostearate, propylene glycol monostearate, self-emulsifying propylene glycol stearate, glyceryl ricinoleate, propylene glycol ricinoleate, propylene glycol fatty acid ester, propylene glycol dioleate, propylene glycol laurate, glyceryl linoleate, glyceryl diisopalmitate, glyceryl sesquioleate, glyceryl monooleate, glyceryl trimyristate, isopropyl lanolate, hexyldecyl dimethyl octanoate, aceto glyceryl, glyceryl triisooctanoate, glyceryl di-2-heptylundecanoate, glyceryl monopyroglutamate monooleate, decaglyceryl decaoleate, dipentaerythrite fatty acid ester, glyceryl stearate/malate, polyoxyethylene hydrogenated castor oil, polyoxyethylene alkyl (12-14) ether (7E.O.), polyoxyethylene alkyl (12-14) ether (12E.O.), polyoxyethylene alkyl ether (20E.O.), polyoxyethylene lauryl ether, polyoxyethylene myristyl ether, polyoxyethylene cetyl ether, polyoxyethylene cetostearyl ether, polyoxyethyl stearyl ether, polyoxyethylene oleyl ether, polyoxyethylene oleyl cetyl ether, polyoxyethylene behenyl ether, polyoxyethylene octylphenyl ether, polyoxyethylene nonylphenyl ether, polyoxyethylene alkyl (12,13) ether (10E.O.), polyoxyethylene octyldodecyl ether, polyoxyethylene cetyl stearyl diether, polyoxyethylene methylglucoside sesquistearate, carboxylated polyoxyethylene tridecyl ether, mixture of polyethylene glycol-4 octanoate and poly(oxyethylene)nonylphenyl ether (14E.O.), polyoxyethylene lanoline alcohol, polyoxyethylene (5) lanoline alcohol, polyoxyethylene (10) lanoline alcohol, polyoxyethylene (15) lanoline alcohol, polyoxyethylene (20) lanoline alcohol, polyoxyethylene (25) lanoline alcohol, polyoxyethylene (40) lanoline alcohol, polyoxyethylene (alkylol/lanolin alcohol)ether (16E.O.), polyoxyethylene lanolin alcohol acetate, polyoxyethylene lanolin, polyoxyethylene hydrogenated lanolin, polyoxyethylene sorbitol lanolin (40E.O.), polyoxyethylene polyoxypropylene hydrogenated lanolin, polyoxyethylene polyoxypropylene lanolin, polyoxyethylene polyoxypropylene lanolin oil, polyoxyethylene stearic acid amide, polyoxyethylene phytosterol, polyoxyethylene dinonylphenyl ether, polyethylene glycol monolaurate, polyethylene glycol dilaurate, polyethylene glycol palmitate, polyethylene glycol dipalmiate, polyethylene glycol dipalmiate, polyethylene glycol monooleate, polyethylene glycol 150 dioleate, polyethylene glycol monostearate, polyethylene glycol distearate, polyoxyethylene glyceryl tristearate, polyethylene glycol 300 lanolin fatty acid, polyethylene glycol 600 lanolin fatty acid, polyethylene glycol 1000 lanolin fatty acid, polypropylene glycol (36) monooleate, polyoxyethylene (20E.O.) sorbitan monolaurate, polyoxyethylene (20E.O.) coconut oil fatty acid sorbitan, polyoxyethylene (20E.O.) sorbitan monopalmitate, polyoxyethylene (40E.O.) sorbitan oleate, polyoxyethylene (6E.O.) sorbitan monooleate, polyoxyethylene (20E.O.) sorbitan monooleate, polyoxyethylene Sorbitan monolaurate, polyoxyethylene sorbitan tetraoleate, polyoxyethylene (20E.O.) sorbitan trioleate, polyoxyethylene (6E.O.) sorbitan monostearate, polyoxyethylene (20E.O.) sorbitan monostearate, polyoxyethylene (6E.O.) sorbitan tristearate, polyoxyethylene sorbitan hexastearate, polyoxyethylene (3E.O.) sorbitan isostearate, polyoxyethylene glyceryl monostearate, sorbeth-6 beeswax, polyoxyethylene polyoxypropyl ene butyl ether, polyoxyethylene (20) polyoxypropylene (15) butyl ether, polyoxyethylene (35) polyoxypropylene (28) butyl ether, polyoxyethylene (36) polyoxypropylene (36) butyl ether, polyoxyethylene (37) polyoxypropylene (38) butyl ether, polyoxyethylene polyoxypropylene cetyl ether, polyoxyethylene polyoxypropylene decyltetradecyl ether, polyoxyethylene polyoxypropylene oligo succinate (3E.O.) (20P.O.), polyoxyethylene polyoxypropylene hexylene glycol ether (300E.O.) (75P.O.), trimethylolpropane tri(polyoxyethylene isostearate) (3E.O.), glyceryl polyoxyethylene oleate, polyoxyethylene (10) polyoxypropylene glycol (30), polyoxyethylene (16) polyoxypropylene glycol (30), polyoxyethylene (25) polyoxypropylene glycol (30), polyoxyethylene (160) polyoxypropylene glycol (30), polyoxyethylene (30) polyoxypropylene glycol (35), polyoxyethylene (200) polyoxypropylene glycol (40), polyoxyethylene (200) polyoxypropylene glycol (70), polyoxyethylene (20) polyoxypropylene glycol (15) butyl ether, polyoxyethylene (6) polyoxypropylene glycol (30), polyoxyethylene (1) polyoxypropylene (4) cetyl ether, polyoxyethylene (1) polyoxypropylene (8) cetyl ether, polyoxyethylene (20) polyoxypropylene (4) cetyl ether, polyoxyethylene (20) polyoxypropylene (8) cetyl ether, polyoxypropylene (9) diglyceryl ether, polyoxypropylene stearyl ether, tetra(polyoxyethylene polyoxypropylene)ethylenediamine, polyoxyethylene (6E.O.) capric/caprylic glyceride, polyoxyethylene glyceryl laurate, polyoxyethylene glyceryl coconut oil fatty acid, polyoxyethylene diethanolamine lauric acid ester (4E.O.), dioctyldodecyl lauroyl glutamate, dipolyoxyethylene stearyl ether diester lauroyl glutamate, polyoxyethylene octyldodecyl ether diester lauroyl glutamate, polyoxyethylene glyceryl pyroglutamic acid isostearate, PEG-40 hydrogenated castor oil PCA isostearate, capric acid diethanolamine, undecylenic acid monoethanolamide, coconut oil fatty acid monoethanolamide, coconut oil fatty acid diethanolamide (1:2 type), coconut oil fatty acid diethanolamide, lauric acid ethanolamide, lauric acid diethanolamide, lauric acid isopropanolamide, lauramide/myristamide diethanolamide (DEA), lauramide/myristamide triethanolamine (TEA), myristic acid diethanolamide, palmitic acid ethanolamide, stearic acid monoethanolamide, stearic acid diethanolamide, stearic acid diethylaminoethylamide, isostearic acid diethanolamide, oleic acid diethanolamide, linoleic acid diethanolamide, tallowamide monoethanolamide, tallowamide diethanolamide, hydrogenated tallowamide diethanolamide, lanolinamide diethylamide, polyoxyethylene coconut oil fatty acid amide (5E.O.), polyoxyethylene (2) coconut oil fatty acid monoethanolamide, polyoxyethylene (5) coconut oil fatty acid monoethanolamide, polyoxyethylene (10) coconut oil fatty acid monoethanolamide, polyoxyethylene coconut oil fatty acid diethanolamide, polyoxyethylene beef tallow alkyl diethanolamine (2E.O.), polyoxyethylene coconut oil alkyl dimethylamineoxide, coconut oil alkyl dimethylamine oxide liquid, oleyldimethylamine oxide, dihydroxyethyl lauramine oxide, pentaerythrityl rosinate, hexaglyceryl oleate, methyl glucose sesquistearate, polyethylene glycol monooleate, polyethylene glycol alkylate, polyethylene alkyl ether, polyglycol diether, lauroyl diethanolamide, fatty acid isopropanolamide, maltitol hydroxy fatty acid ether, alkylated polysaccharide, alkylglucoside; trehalose mono-fatty acid ethers such as trehalose monomyristate, trehalose monoisostearate, and trehalose monoundecylate; polyoxyethylene methyl glucoside dioleate (120E.O.); sugar esters such as sucrose fatty acid ester and glyceryl cocoate; non-ionic surfactants such as lipophilic glycerin monostearate, self-emulsifying glyceryl monostearate, polyglyceryl monostearate, polyglyceryl alkylate, sorbitanmonooleate, polyethylene glycol monostearate, polyoxyethylene sorbitan monooleate, polyoxyethylated sterol, polyoxyethylated lanolin, polyoxyethylated beeswax, polyoxyethylene hydrogenated castor oil, glycerin fatty acid ester, polyglycerin fatty acid ester, POE sorbitan fatty acid ester, POE sorbit fatty acid ester, POE glycerin fatty acid ester, POE alkyl ether, POE fatty acid ester, POE hydrogenated castor oil, POE castor oil, POE•POP copolymer, POE•POP alkyl ether, polyether-modified silicone lauric acid alkanolamide, alkylamineoxide, hydrogenated soybean phospholipid, caprylyl glucoside, glycerol citric acid fatty acid ester, glyceryl stearate citrate, corn oil PEG-8 esters, cocamide DEA, cocamide MEA, cocamide MIPA, sucrose tetrastearate triacetate, hydrogenated palm kernel glycerides, hydrogenated palm PEG-200 glyceride, hydrogenated palm glycerides, sorbitan sesquiisostearate, polyglyceryl-2 sesquiisostearate, polyglyceryl-2 sesquicaprylate, and PEG-20 methyl glucose sesquistearate; anion surfactants such as sodium stearate, zinc stearate, calcium stearate, magnesium stearate, aluminum stearate, aluminum isostearate, triethanolamine stearate, potassium palmitate, sodium cetyl sulfate, sodium lauryl phosphate, disodium lauryl phosphate, triethanolamine palmitate, sodium polyoxyethylene lauryl phosphate, sodium N-acylglutamate, sodium palmitate, sodium laurate, potassium laurate, zinc laurate, triethanolamine laurate, sodium laureate, sodium lauryl sulfate, potassium lauryl sulfate, ammonium lauryl sulfate, monoethanolamine lauryl sulfate, diethanolamine lauryl sulfate, triethanolamine lauryl sulfate, sodium lauryl diaminoethyl glycine, triethanolamine ether alkyl sulfate, turkey red oil, linear dodecyl benzene sulfonate, polyoxyethylene hydrogenated castor oil maleate, acyl methyl taurate, fatty acid soap, α-acylsulfonate, alkyl sulfonate, alkyl allyl sulfonate, alkyl naphthalene sulfonate, alkyl sulfate, POE alkyl ether sulfate, alkyl amide sulfate, alkyl phosphate, POE alkyl phosphate, alkyl amide phosphate, alkyloyl alkyl taurate, N-acyl amino acid salt, POE alkyl ether carbonate, alkylsulfo succinate, sodium alkyl sulfoacetate, acyl isethionate, acylated hydrogenated collagen peptide salt, perfluoroalkyl phosphate, soap noodle, potash soap, zinc undecylenate, soap noodle containing potassium, potassium coconut oil fatty acid, sulfonated castor oil, sodium myristate, potassium myristate, zinc myristate, magnesium myristate, sodium oleate, potassium oleate, N-acyl-L-glutamic acid triethanolamine, sodium N-acyl-L-glutamate, sodium N-coconut oil fatty acid acyl-L-glutamate, sodium N-coconut oil fatty acid/hydrogenated tallowate acyl-L-glutamate, N-coconut oil fatty acid acyl-L-glutamic acid triethanolamine, di sodium stearoyl-L-glutamate, sodium N-hydrogenated tallowate acyl-L-glutamate, sodium N-lauroyl-L-glutamate, N-stearoyl-L-glutamate, N-lauroyl-L-lysine, lauroyl-L-glutamic acid triethanolamine, L-arginine ethyl•DL-pyrrolidone carboxylic acid salt, N-coconut oil fatty acid acyl-L-arginine ethyl•DL-pyrrolidone carbonate, cocoyl sarcosinate, sodium cocoyl sarcosinate, N-(cocoyl)

sarcosine triethanolamine salt, lauroyl sarcosine, sodium lauroyl sarcosine, lauroyl sarcosine triethanolamine, carboxylated polyoxyethylene tridecyl ether sodium salt (3E.O.), sodium β-laurylaminopropionate, laurylaminopropionate solution, potassium methyl cocoyl taurate, sodium methyl cocoyl taurate, sodium lauroylmethyl taurate, sodium laurylsulfoacetate, sodium cocoyl methyl alanine solution, cocoyl triethanolamine solution, sodium lauroylmethyl-β-alanine solution, disodium lauryl-N-carboxymethoxyethyl-N-carboxymethyl-imidazolinium dodecanoyl sarcosine, sodium coco alkyl-N-carboxyethyl-N-hydroxyimidazolium betaine, disodium coco alkyl-N-carboxyethoxyethyl-N-carboxyethyl-imidazolinium hydroxide, disodium coco alkyl-N-carboxymethoxyethyl-N-carboxymethyl-imidazo linium hydroxide, disodium coco alkyl-N-carboxymethoxyethyl-N-carboxymethyl-imidazo linium lauroyl sulfate, sodium myristoylmethyl-β-alanine solution, sodium methyl stearoyl taurate, sodium tetradecene sulfonate, sodium dodecylbenzene sulfonate, triethanolamine dodecylbenzene sulfonate, sodium alkanesulfonate, ammonium alkyl sulfate, sodium octylphenoxy diethoxyethyl sulfonate, triethanolamine/magnesium coco alkyl sulfate, sodium myristyl sulfate, sodium cetostearyl sulfate, sodium oleyl sulfate, triethanol amine oleyl sulfate, sodium polyoxyethylene lauryl ether sulfate, ammonium polyoxyethylene lauryl ether sulfate (2E.O.), triethanolamine polyoxyethylene lauryl ether sulfate, ammonium polyoxyethylene alkyl ether sulfate (3E.O.) solution, diethanolamine polyoxyethylene alkyl ether sulfate (3E.O.) solution, triethanolamine polyoxyethylene alkyl ether sulfate (3E.O.) solution, sodium polyoxyethylene alkyl ether sulfate (3E.O.) solution, sodium cocomonoglyceride sulfate, polyoxyethylene (5) coconut fatty acid monoethanolamide phosphate; polyoxyethylenealkyl (12-14) ether phosphate (2E.O.), (8E.O.), (10E.O.); polyoxyethylene laurylether phosphate, sodium polyoxyethylene laurylether phosphate, polyoxyethylene cetylether phosphate, sodium polyoxyethylene cetylether phosphate, polyoxyethylene stearylether, polyoxyethylene cholestearyl ether, polyoxyethylene stearylether phosphate, polyoxyethylene oleylether phosphate, sodium polyoxyethylene oleylether phosphate, diethanolamine polyoxyethylene oleylether phosphate, polyoxyethylene alkylphenylether phosphate, triethanolamine polyoxyethylene alkylphenylether phosphate, polyoxyethylene-polyoxypropylene cetylether phosphate, polyoxypropylene glyceryl ether phosphate, polyoxypropylene butyl ether phosphate, disodium laureth sulfosuccinate, sodium cocoyl ethyl ester sulfonate, dioctyl sodium sulfosuccinate, sodium octylphenoxy diethoxyethyl sulfonate, disodium lauryl sulfosuccinate, disodium oleic acid amidosulfosuccinate, C12-15 pareth-3 phosphate, sodium polyoxyethylene alkyl (C12-14) sulfosuccinate (7E.O.), disodium lauramido PEG-5 sulfosuccinate (5E.O.), sodium isostearoyl lactylate, sodium undecylenoyl hydrolyzed collagen, potassium undecylenoyl hydrolyzed collagen, sodium 2-undecyl-1-hydroxyethyl imidazolinium betaine, sodium lauroyl hydrolyzed collagen, sodium cocoyl hydrolyzed collagen, potassium cocoyl hydrolyzed collagen, potassium cocoyl hydrolyzed collagen solution, TEA-cocoyl hydrolyzed collagen, isostearoyl hydrolyzed collagen, isostearoyl hydrolyzed silk, AMPD-isostearoyl hydrolyzed collagen, ethylenediamine-N,N,N',N'-tetrakis (2-hydroxylpropyl)dioleate, dodecanoylsarcosine, sodium lauriminodipropionate (30%), oleoyl sarcosine, sodium myristoyl β-alanine solution, sodium undecylhydroxyethylimidazolinium betaine, ammonium C12,13,16 alkyl sulfate, triethanolamine alkyl (11,13,15) sulfate (1), triethanolamine alkyl (11,13,15) sulfate (2), triethanolamin alkyl (12-15) sulfate, triethanolamin alkyl (12-14) sulfate, sodium alkyl (12, 13) sulfate, triethanolamin polyoxyethylene alkyl ether sulfate (3E.O.) solution, sodium C11-15 pareth-3 sulfate, sodium C12-13 pareth-3 sulfate, sodium C12-15 pareth-3 sulfate, TEA C12-13 pareth-3 sulfate, TEA/Na C12-13 pareth-3 sulfate, sodium PEG-3 cocamide sulfate, sodium PEG-5 cocamide phosphate, disodium PEG-5 laurylcitrate sulfosuccinate, PPG-5-ceteth-10, PEG-25 butyl phosphate, sodium C14-18 alkyl sulfonate, C20-22 alkyl phosphate, isolaureth-4 phosphate, undecylenoyl glycine, potassium olive fatty acid, oleyl sarcosine, sodium oleyl methyl taurate, oleth-3 phosphate, oleth-4 phosphate, oleth-5 phosphate, oleth-10 phosphate, oleth-20 phosphate, sodium oleth-7 phosphate, sodium oleth-8 phosphate, sodium C14-16 olefin sulfonate, capryloyl glycine; cocoyl glutamates such as sodium cocoyl amino acids, cocoyl alanine triethanolamine, sodium cocoyl isethionate, ammonium cocoyl isethionate, potassium cocoyl glycine, sodium cocoyl glycine, triethanolamine cocoyl glutamate, cocoyl glutamate, disodium cocoyl glutamate, and potassium cocoyl glutamate; cocoyl sarcosine, sodium cocoyl sarcosinate, triethanolamine cocoyl sarcosinate, sodium cocoyl taurate, cocoyl methyl β-alanine, sodium cocoyl methyl β-alanine, methyl cocoyl taurate, potassium methyl cocoyl taurate, magnesium methyl cocoyl taurate, sodium methyl cocoyl taurate, sodium cocoyl apple amino acids, sodium coceth sulfate, di-C11-15 pareth-2 phosphate, di-C12-15 pareth-4 phosphate, di-C12-15 pareth-8 phosphate, di-C12-15 pareth-10 phosphate, dioleyl phosphate, sodium dioleth-8 phosphate, sodium dioleth-8 phosphate, sodium dicocoylethylenediamine PEG-15 sulfate, sodium dilaureth-10 phosphate, steareth-2 phosphate, steareth-3 phosphate, calcium stearoyl lactylate, sodium stearoyl lactylate, disodium undecylenamido MEA-sulfosuccinate, disodium lauramido MEA-sulfosuccinate, disodiumlaureth sulfosuccinate, DEA-cetyl phosphate, potassium cetyl phosphate, sodium cetyl stearyl sulfate, ceteth-10 phosphate, ceteth-20 phosphate, triceteareth-4 phosphate, trideceth-4 carboxylic acid, trideceth-8 carboxylic acid, sodium trideceth-4 carboxylic acid, sodium trideceth-7 carboxylic acid, sodium trideceth-3 carboxylic acid, potassium trideceth-7 carboxylic acid, trilaureth-4 phosphate, oleyl lactate, sodium palmoyl glutamate, magnesium palmitoyl glutamate, sodium palmitoyl sarcosinate, palmitoyl proline, sodium palmitoyl proline, sodium methyl palmitoyl taurate, potassium myristoyl glutamate, sodium myristoyl glutamate, sodium myristoyl sarcosinate, sodium methyl myristoyl taurate, potassium cocoate, triethanolamine cocoate, arginine cocoate, disodium lauryliminodiacetate, sodium lauryl glycol carboxylate, laureth-5 carboxylic acid, laureth-6 carboxylic acid, laureth-11 carboxylic acid, sodiumlaureth-5 carboxylate, sodiumlaureth-6 carboxylate, sodiumlaureth-11 carboxylate, laureth-5 acetate, laureth-6 acetate, potassium-laureth-4,5 acetate, sodiumlaureth-3 acetate, sodiumlaureth-4 acetate, sodiumlaureth-5 acetate, sodiumlaureth-6 acetate, sodiumlaureth-11 acetate, MIPA-laureth sulfate, sodium laureth sulfate, triethanolamine laureth sulfate, ammoniumlaureth-2 sulfate, ammoniumlaureth-3 sulfate, laureth-1 phosphate, laureth-2 phosphate, laureth-4 phosphate, sodium lauroylaspartate, sodium lauryl oat amino acids, sodium lauroyl lactate, N-lauroyl-N-methyl-β-alanine potassium salt, TEA-lauroyl methylaminopropionate, dicetyl phosphate, and cetyl phosphate; cation surfactants such as lauryl trimethyl ammonium chloride, dicocodimonium chloride, myristyl dimethyl benzyl ammonium chloride, cetyltrimethylammonium chloride, laurylpyridinium chloride, cetylpyridinium chloride, benzethonium chloride, stearyl trimonium chloride, benzalkonium chloride, benzalkonium chloride solution, lauramine oxide, alkyltrimethylammonium chloride, stearyl trimethyl ammonium chloride, stearyl dimethyl benzyl ammonium chloride, dimethyl stearyl ammonium chloride treated hectorite, benzyl dimethyl stearyl ammonium chloride treated hectorite, distearyldimonium chloride, benzyl dimethyl stearyl ammonium chloride treated hectorite, distearyldimonium chloride, distearyldimonium chloride treated bentonite, dialkyldimethyl ammonium chloride, tri(polyoxyethylene)stearyl ammonium chloride (5E.O.), di(polyoxyethylene) oleyl methyl ammonium chloride (2E.O.), N-(stearoyl colamino formyl methyl) pyridinium chloride, polyoxypropylene methyl diethyl ammonium chloride, alkyldiaminoethylglycine hydrochloride solution, alkylisoquinolinium bromide solution, laurtrimonium bromide, ammonium cetyl trimethyl bromide, stearyl trimethyl ammonium bromide, cetyltrimethylammonium saccharin, stearyltrimethylammonium saccharin, polyethyleneglycol•epichlorohydrin•coconut alkylamine•dipropylenetriamine condensate, polyethyleneglycol•epichlorohydrin•tallow alkyl amine •dipropylenetriamine condensate, ethyl sulfate lanolin fatty acid aminopropyl ethyl dimethyl ammonium (1), (2); behenyl trimethyl ammonium bromide, behenic acid amide propyl dimethyl hydroxypropyl ammonium chloride, stearic acid diethylaminoethylamide, stearic acid diethylaminoethyl amide, stearic acid dimethylaminopropylamide, lanolin derivative quaternary ammonium salt, PEG-5 oleamine, PEG-2 oleammonium chloride, PEG-2 cocamine, PEG-3 cocamine, PEG-5 cocamine, PEG-10 cocamine, PEG-15 cocamine, PEG-2 dimeadowfoamamidoethylmonium methosulfate, hydroxypropyl arginine lauryl/myristyl ether HCl, ceteartrimonium chloride, C10-40 isoalkylamidopropylethyldimonium ethosulfate, isostearyl ethylimidazolium ethosulfate, caesalpinia spinosa hydroxypropyltrimonium chloride, quaternium-33, quaternium-91, cocamidopropyl PG-dimonium chloride phosphate, cocamidopropyl betainamide MEA chloride, PCA ethyl cocoyl arginate, cocotrimonium methosulfate, trigonella foenum-graecum hydroxypropyltrimonium chloride, myrist/palmitamidobutyl guanidine acetate, di-C12-18 alkyl dimonium chloride, dicocoylethyl hydroxyethylmonium methosulfate, dicocodimonium chloride, distearyldimonium chloride, distearoylethyl hydroxyethylmonium methosulfate, dicetyldimonium chloride, dipalmitoylethyl hydroxyethylmonium methosulfate, dihydroxypropyl PEG-5 linoleammonium chloride, dimethyl PABA amidopropyl laurdimonium tosylate, dimethyl stearamine, stearamidoethyl diethylamine, stearamidopropyl diethylamine, stearalkonium chloride, steartrimonium saccharinate, steartrimonium chloride, steartrimonium bromide, stearoxypropyltrimonium chloride, cetalkonium chloride, cetylpyridinium chloride, cetrimonium chloride, cetrimonium bromide, cetrimonium methosulfate, soytrimonium chloride, palmitamidopropyltrimonium chloride, panthenyl hydroxypropyl steardimonium chloride, hydroxyethyl cetyldimonium phosphate, hydroxypropyltrimonium honey, hydroxypropyl bis-hydroxyethyldimonium chloride, behenamidopropyl dimethylamine, behenamidopropyl dimethylamine, behentrimonium chloride, behentrimonium methosulfate, poloxamine 701, poloxamine 702, poloxamine 704, bishydroxyethyl biscetyl malonamide, sodium palm oil alkyl PG dimonium chloride phosphate, laurtrimonium chloride, laurylpyridinium chloride, and linoleamidopropyl PG-dimonium chloride phosphate; ampholytic surfactants such as of carboxy betaine-, amide betaine-, sulfo betaine-, hydroxy sulfobetaine-, amido sulfo betaine-, phospho betaine-, aminocarboxylate-, imidazoline derivative-, and amideamine-types including lauryl dimethyl amino acetate betaine, 2-alkyl-N-carboxymethyl-N-hydroxyethylimidazolinium betaine, undecyl-N-hydroxyethyl-N-carboxymethylimidazolinium betaine, palm oil alkyl betaine, cocamidopropyl betaine, stearyl dihydroxyethyl betaine, stearyl betaine dimethylamino acetate, bis(stearyl-N-hydroxyethylimidazoline)chloroacetic acid complex, cocoyl hydrolyzed collagen, oleoyl hydrolyzed collagen, hexadecyl hydrolyzed collagen, lauramidopropyl betaine/water, myristoyl hydrolyzed collagen, alkyl aminoethyl glycine chloride solution, and lecithin; and others including PEG-3 lauramine oxide, oleamine oxide, oleyl betaine, capryl/capramidopropyl betaine, cocamine oxide, sodium cocoamphoacetate, sodium cocoamphodiacetate, disodium cocoamphodiacetate, sodium cocoamphopropionate, dihydroxyethyl lauramine oxide, stearamine oxide, stearyl betaine, sodium palm kernelamidoethyl hydroxyethyl amino propionate, palm kernelamidopropyl betaine, C12-14 hydroxyalkyl hydroxyethyl β-alanine, hepta hydroxyethyl carboxylate methylimidazolinium chloride/hepta decyl bis-hydroxyethyl imidazolinium, myristamidopropyl betaine, myristamine oxide, myristyl betaine, lauramidopropylamine oxide, lauramidopropyl hydroxysultaine, lauramidopropyl betaine, sodium lauraminopropionate, lauramine oxide, sodium lauriminodipropionate, lauryl hydroxysultaine, lauryl betaine, sodium lauroamphoacetate, and lauroyl lysine; escin, sodium surfactin, saponin, hydroxylated lecithin, hydrogenated lysolecithin, hydrogenated lecithin, cephalin, phosphatidyl serine, lysolecithin, phospholipid, lecithin, and soluble collagen. Among these surfactants, non-ionic surfactants are preferable; i.e., polyoxyethylene alkyl ether, polyoxyethylene fatty acid ester, polyoxyethylene sorbitan fatty acid ester, glycerin-fatty acid ester, polyglycerol fatty acid ester series, polyoxyethylene glycerine fatty acid ester, polyoxyethylene hydrogenated castor oil, polyoxyethylene sorbitol fatty acid ester, etc., are more preferable.

Particularly, in the case of cosmetic lotions in which the external dermal composition containing one or more L-ascorbic acid, derivatives thereof, and their salts are incorporated, the following surfactants, which are widely used in the field of cosmetics and have a higher effect of inhibiting the turbidity or precipitation of cosmetics over time, can be preferably used; L-arginine ethyl ester •DL-pyrrolidone carboxylate, glycereth-25 PCA isostearate, PEG-9 polydimethylsiloxyethyl dimethicone, sorbitan cocoate, polyoxyethylene polyoxypropylene decyltetradecyl ether, polyoxyethylene cetylether, polyoxyethylene stearylether, polyoxyethylene methyl glucoside, polyoxyethylene lauryl ether, polyoxyethylene hydrogenated castor oil, polyoxyethylene hydrogenated castor oil, sorbitan isostearate, polyoxyethylene hydrogenated castor oil monoisostearate, glycerin-fatty acid ester, polyglyceryl diisostearate, sucrose fatty acid ester, sodium stearoyl glutamate, sodium stearoyl lactylate, sorbitan sesquiisostearate, sorbitan sesquioleate, polyoxyethylene alkyl (C12 to C15) ether phosphate, polyoxyethylene cholesteryl ether, polyoxyethylene cetylether phosphate, polyoxyethylene cetostearyl ether, polyoxyethylene phytosterol, polyoxyethylene behenyl ether, polyoxyethylenesorbitanmonooleate (20E.O.), glyceryl monostearate, polyethylene glycol monostearate, polyoxyethylene glyceryl monostearate, polyoxyethylene sorbitan monolaurate, dioctyldodecyl lauroyl glutamate, hydrolyzed collagen solution, glyceryl monostearate, hydrogenated lysolecithin, hydrogenated soybean phospholipid, and soluble collagen, one or more of which can be desirably used alone or in combination.

Into the above-identified cosmetic solutions can be incorporated the following one or more ingredients selected from flavors, pigments/dyes, antiseptics, bactericides, ultraviolet-absorbing agents, sequestering agents, and buffers in respective amounts of, usually, at least 0.0001% by mass, preferably, 0.001 to 50% by mass, more preferably, 0.01 to 25% by mass, and more further preferably, 0.1 to 10% by mass to the mass of the respective cosmetic solutions of the present invention.

(Flavors)

Examples of the flavors include synthetic and natural flavors such as essential oils, as well as compound perfume and flavor materials; aldehydes such as benzaldehyde, cinnamaldehyde, cyclamen aldehyde, citral, citronellal, 2-methyl-3-(4-methylphenyl) propanal, undecenal, methylnonylacetaldehyde, 3,7-dimethyl-1-octanal, hydroxycitronellal, methoxycitronellal, perillaldehyde, myrtenal, caryophyllene aldehyde, n-hexal, 2-methylbutanal, isovaleraldehyde, n-valeraldehyde, acetaldehyde, n-heptanal, n-octanal, n-nonanal, 2-methyloctanal, 3,5,5-trimethyl hexanal, 1-decanal, undecanal, dodecanal, 2-methyl decanal, 2-methyl undecanal, tridecanal, tetradecanal, 2-pentenal, cis-3-hexenal, trans-2-hexenal, trans-2-heptenal, 4-heptenal, trans-2-octenal, trans-2-nonenal, cis-6-nonenal, 2,6-dimethyl-5-heptenal, trans-4-decenal, cis-4-decenal, trans-2-decenal, 2,5,6-trimethyl-4-heptenal, 10-undecenal, trans-2-undecenal, trans-2-dodecenal, 3-dodecenal, trans-2-tridecenal, 2,6,10-trimethyl-9-undecene-1-al, 2,4-hexadienal, 2,4-heptadienal, 2,4-octadienal, 2,4-nonadienal, 2,6-nonadienal, 2,4-decadienal, 2,4-undecadienal, 2,4-dodecadienal, 5,9-dimethyl-4,8-decadienal, 3,7,9-trimethyl-2,6-decadiene-1-al, 2,6,10-trimethyl-5,9-undecadienal, α-methylene citronellal, campholenic aldehyde, cyclocitral, isocyclocitral, 2,6,6-trimethyl-1,3-cyclohexadiene-1-carboxy aldehyde, 6,10-dimethyl-3-oxa-9-undecenal, geranyloxyacetaldehyde, dimethyl tetrahydrobenzaldehyde, 3-propyl bicyclo[2,2,1]-5-hepten-2-carboxyaldehyde, methoxydicyclopentadiene carboxyaldehyde, 4-tricyclocylidene butanal, 4-(4-methyl-3-cyclohexenylidene-1)pentanal, 4(3)-(4-methyl-3-pentene-1-yl)-3-cyclohexene-1-carboxyaldehyde, cetonal, inonal, terrestral, p-tolylaldehyde, phenylacetaldehyde, 3-phenylbutanal, cuminaldehyde, p-methylphenylacetaldehyde, p-isopropylphenylacetaldehyde, hydratropaldehyde, p-methylhydratropaldehyde, p-isopropyl hydra toro pa aldehyde, phenylpropionaldehyde, β-methylhydrocinnamic aldehyde, jasmorange, bourgeonal, floralozone, suzaral, salicylaldehyde, anisaldehyde, o-methoxybenzaldehyde, o-methoxycinnamicaldehyde, canthoxal, vanillin, ethyl vanillin, methyl vanilline (3,4-dimethoxybenzaldehyde), helional, phenoxyacetaldehyde, p-methylphenoxyacetaldehyde, furfural, 5-methylfurfural, 5-hydroxymethyl-2-furfural, furylacrolein, lyral, bern aldehyde, homomyrac aldehyde, junipal, vertral, lilial, mefranal, eglantal, cocarl, α-methylcinnamaldehyde, α-butylcinnamaldehyde, α-amylsinecinnamaldehyde, α-hexylcinnamaldehyde, and formylethyltetramethyltetralin; esters such as terpinel acetate, vetiveryl acetate, benzyl acetate, linalyl acetate, isopentyl salicylate, benzyl salicylate, hexyl salicylate, cis-3-hexenyl salicylate, ethyl formate, cis-3-hexenyl formate, linalyl formate, citronellyl formate, geranyl formate, benzyl formate, phenylethyl formate, ethyl acetate, butyl acetate, isoamyl acetate, methyl cyclopentylidene acetate, hexyl acetate, cis-3-hexenyl acetate, trans-2-hexenyl acetate, isononyl acetate, citronellyl acetate, lavandulyl acetate, geranyl acetate, myrcenyl acetate, terpinyl acetate, menthyl acetate, menthanyl acetate, nopyl acetate, n-bornyl acetate, isobornyl acetate, p-t-butylcyclohexyl acetate, o-t-butylcyclohexyl acetate, tricyclodecenyl acetate, 2,4-dimethyl-3-cyclohexene-1-methanyl, phenylethyl acetate, styralyl acetate, dimethylbenzylcarvyl acetate, cinnamyl acetate, anisyl acetate, p-cresyl acetate, heliotropyl acetate, acetyl eugenol, acetyl isoeugenol, guaiyl acetate, cedryl acetate, ethyl propionate, isoamylpropionate, citronellyl propionate, geranyl propionate, linalyl propionate, terpinyl propionate, benzyl propionate, cinnamyl propionate, allyl cyclohexylpropionate, tricyclodecenyl propionate, ethyl butyrate, ethyl 2-methylbutyrate, butyl butyrate, isoamyl butyrate, hexyl butyrate, linalyl butyrate, geranyl butyrate, citronellyl butyrate, benzyl butyrate, cis-3-hecenyl isobutyrate, citronellyl isobutyrate, geranyl isobutyrate, linalyl isobutyrate, benzyl isobutyrate, phenylethyl isobutyrate, tricyclodecenyl isobutyrate, ethyl isovalerate, propyl pentanoate, citronellyl isovalerate, geranyl isovalerate, isovaleric acid benzyl ester, isovaleric acid 3-phenyl-2-propenyl ester, isovaleric acid phenethyl ester, ethyl caproate, allyl caproate, ethyl enanthate, allyl enanthate, ethyl caprate, citronellol tiglate, methyl benzoate, ethyl benzoate, butyl benzoate, isoamyl benzoate, geranyl benzoate, linalyl benzoate, benzyl benzoate, phenylethyl benzoate, methyl phenyl acetate, ethyl phenyl acetate, isobutyl phenyl acetate, isoamyl phenyl acetate, geranylphenyl acetate, benzyl phenyl acetate, phenylethyl phenyl acetate, p-crezyl phenyl acetate, methyl cinnamate, ethyl cinnamate, benzyl cinnamate, cinnamyl cinnamate, phenylethyl cinnamate, methyl salicylate, ethyl salicylate, isobutyl salicylate, amyl salicylate, hexyl salicylate, cis-3-hexenyl salicylate, phenylethyl salicylate, methyl jasmonate, methyl dihydrojasmonate, ethyl tricyclodecan-2-yl-carboxylate ("FRUITATE"), allyl 2-pentyloxyglycolate, ethyl 3-methyl-3-phenylglycidate, ethyl 2-pentanoate, 4-acetoxy-3-amyltetrahydropyrane, cyclohexyl salicylate, ethyl 2-cyclohexyl propionate, ethyl tricyclo[5.2.1.02,6]decane-2-carboxylate, and 2-methylpenthyl 2-methylpentylate; lactones such as γ-undecalactone, pentalide(cyclopentadecanolide), habanolide (1-oxa-cyclohexadecen-2-one), ambrettolide, cyclohexadecanolide, 10-oxahexadecanolide, 11-oxahexadecanolide, 12-oxahexadecanolide, ethylene dodecanedioate, γ-butyrolactone, γ-valerolactone, *angelica* lactone, γ-hexanolactone, γ-heptalactone, γ-octalactone, γ-nonalactone, 3-methyl-4-octanolide, γ-decalactone, γ-dodecalactone, γ-jasmolactone, jasmine lactone, cis-jasmonlactone, lactojasmon, jasmolactone, menthalactone, n-butylphthalide, propylidenephthalide, butylidenephthalide, δ-hexalactone, δ-octalactone, 4,6,6(4,4,6)-trimetyltetrahydropyran-2-on, δ-nonalactone, δ-decalactone, δ-2-decenolactone, δ-undecalactone, δ-dodecalactone, δ-tridecalactone, δ-tetradecalactone, lactoscaton(decahydro-4,α-hydroxy-2,8,8-trimethylnaphtalin-2-carboxy acid-δ-lactone), coumarin, dihydrocoumarin, cyclohexyl lactone, 6-methyl coumarin, ε-decalactone, and ε-dodecalactone; ketones such as acetyl caryophyllene, carvone, pulegone, piperitenone, piperitone, camphor, isolongifolanone, nootkatone, 2-heptanone, 2-pentanone, 3-hexanone, 3-heptanone, 4-heptanone, 2-octanone, 3-octanone, 2-nonanone, 3-nonanone, 2-undecanone, 2-tridecanone, methyl isopropyl ketone, ethyl isoamyl ketone, mesityl oxide, butylidene acetone, methylheptadienon, methylheptenon, dimethyloctenone, 4-methylene-3,5,6,6-tetramethyl-2-heptanone, geranylacetone, farnesylacetone, acetoin, 5-hydroxy-4-octanone, methyl lavender ketone, diacetyl, 2,3-pentadione, 2,3-hexadione, 3,4-hexadione, 2,3-heptadione, acetylisovaleryl, amylcyclopentanone, amylcyclopentenone, 2-cyclopentylcyclopentanone, hexylcyclopentanone, 2-n-heptylcyclopentanone, cis-jasmon, dihydrojasmon, isojasmon, trimethyl pentyl cyclopentanone, sedamon (2-butylidene-3, 5,5(3,3,5)-trimethyl cyclopentanone), sandex (3-methyl-5-(2,2,3-trimethyl-3-cyclopentenyl)-3-pentene-2-on, cyclotene, 3,5-dimethyl-1,2-cyclopentadione, methylcholine, 2-t-butylcyclohexanone, p-t-butylcyclohexanone, 3,3-dimethyl cyclohexyl methyl ketone, 2-sec-butylcyclohexanone, artemone, celery ketone (3-methyl-5-propyl-2-cyclohexenone), krypton, p-t-penthylcyclohexanone, methylcyclocitron, nerone, 4-cyclohexyl-4-methyl-2-pentanone, habanor (2-(1-cyclohexene-1-yl)-cyclohexanone), maltol, ethyl maltol, oxide ketone, emoxyfurone (5-ethyl-3-hydroxy-4-methyl-2 [5H]-furanone, homofuraneol (2-ethyl-4-hydroxy-5-methyl-3[2H]-furanone and 5-ethyl-4-hydroxy-2-methyl-3[2H]-furanone), sotolon, furaneol, acetyl dimethylfuran, furfuralacetone, 2-acetyl-5-methylfuran, 2-acetylfuran, methyltetrahydrofuranone, dibenzyl ketone, benzophenone, methyl naphthyl ketone, 4-damascol (5-phenyl-5-methyl-3-hexanone), 4-methyl-4-phenyl-2-pentanone, α-methylanisalacetone, heliotropylacetone, anisylideneacetone, anisylacetone, p-methoxyphenylacetone, raspberry ketone, lavandozon (3-methyl-4-phenyl-3-butene-2-on), benzylideneacetone, p-methoxyacetophenone, p-methylacetophenone, propiophenone, acetophenone, isodamascone, α-dynascone, "IRITONE" (trimethylcyclohexenylbutenone), "INONE", pseudoionone, methyl ionone, methyliritone, 2,4-di-t-butylcyclohexanone, allylionone, 2,6,6-trimethyl-2-cyclohexene-1,4-dione, 2-acetyl-3,3-dimethylnorbornane, "FLOREX" (hydro-5,8-methano-2H-1-benzopyran), "PLICATONE" (4-methyltricyclo[6.2.1.02.7]undecan-5-one, oxocedrane, beltfix, verbenone, fenchone, calone, trimofix O, epitone, atrinon, cashmeran, 3-methylcyclopentadecanone-1, cycloheptadeca-9-en-1-one, cyclopentadecanone, cyclohexadecenone, phantolide, 4-acetyl-6-t-butyl-1,1-dimethylindan, "TRASEOLIDE" (5-acetyl-1,1,2,6-tetraméthyle-3-isopropyl-dihydroindene), tonalid, "VITALIDE" (acetyldimethyl tetrahydrobenzindan), dihydrocarvone, diosphenol, zingerone, and iso E super; carbohydrates such as phenylacetic acid, "SANDALORE", linalool, musk ketone, methyl ionone, iris oil, irone, indole, ylang-ylang oil, estragole, oakmoss, opoponax resinoid, eugenol, aurantiol, galaxolide, carvacrol, L-carvone, camphor, canon, carrot seed oil, clove oil, geraniol, geranylnitrile, sandalwood oil, cyclopentadecanolide, dihydromyrcenol, jasmine absolute, cinnamon bark oil, 1,8-cineol, styrax resinoid, cedarwood oil, cedrene, cedrol, celery seed oil, thyme oil, damascone, damascenone, thymol, tuberose absolute, decanolactone, terpineol, γ-terpinene, "TRIPRAL" (dimethyl tetrahydrobenzaldehyde), 2,6-nonadienol, nonalactone, patchouli alcohol, patchouli oil, phenethyl alcohol, petitgrain oil, cis-3-hexcenol, peru balsam, vetivert oil, vetivelol, peppermint oil, pepper oil, heliotropine, bergamot oil, borneol, myrrh resinoid, menthol, l-menthol, l-menthone, eucalyptus oil, β-ionone, lime oil, lavender oil, d-limonene, lemon oil, rose absolute, rose oxide, rose oil, rosemary oil, asafetida resinoid, ajowan oil, star anise oil, abies oil, amyris oil, ambrette seed oil, ambergris tincture, ylang ylang absolute, iris resinoid, iris absolute, wintergreen oil, elemi oleoresin, elemi resinoid absolute, elemi tincture, oakmoss concrete, oakmoss absolute, oakmoss resin, oakmoss resinoid, ocotea oil, Osmanthus absolute, Osmanthus concrete, Opoponax resinoid, Opoponax absolute, Opoponax oil, Oribanum resinoid, Oribanum absolute, Oribanum oil, allspice oil, Oregano oil, Oregano oleoresin, orange flower absolute, orange flower concrete, cananga oil, gurjun balsam, cascarilla bark oil, castoreum absolute, cassie absolute, cassie flower oil, cassia oil, gardenia absolute, carnation absolute, cabreuva oil, chamomile oil, cardamon oil, galvanum oil, galvanum resin, galvanum resinoid, caraway seed oil, guaiac wood oil, guaiac resin, guaiac concrete, Cinnamomum camphora oil, cubeb oil, cumin oil, cumin absolute, cumin oleoresin, clary sage oil, grapefruit oil, costus oil, copaiba balsam, copaiba balsam oil, copaiba balsam resin, coriander oil, sassafras oil, broom absolute, perilla oil, citronella oil, jasmin concrete, juniper berry oil, civet absolute, civet tincture, jonquil absolute, agarwood, ginger oil, cinnamon oil, cinnamon leaf oil, Japanese cedar oil, styrax oil, spearmint oil, savory oil, sage oil, cedar oil, cedar leaf oil, target oil, tarragon oil, dill oil, tea tree oil, tree moss absolute, tolu balsam, nutmeg oil, Narcissus absolute, neroli oil, violet leaf absolute, pine oil, basil oil, parsley leaf oil, parsley seed oil, parsley herb, mint oil, vanilla absolute, honeysuckle absolute, palmarosa oil, valerian oil, bitter orange oil, hyssop oil, hiba oil (Thujopsis dolabrata wood oil), hyacinth absolute, fennel oil, fig absolute, buchu oil, pennyroyal oil, peppermint oil, benzoin tincture, benzoin resinoid, Bois de rose oil, houshou oil, hop oil, hop concrete, hop absolute, marjoram oil, mandarin oil, orange oil, mimosa concrete, mimosa absolute, mimosa oil, mill absolute, mill oil, musk absolute, musk tincture, Citrus junos oil, Artemisia oil, abdanum (rockrose) oil, abdanum resinoid, lavender absolute, lavandin oil, lavandin absolute, linaloe oil, lemon grass oil, rose concrete, lavage oil, Laurus nobilis oil, Laurus nobilis leaf oil, wormwood oil, musk, civet, ambergris, castoreum, musk zibata, α-pinene, β-pinene, camphene, myrcene, terpineol, terpinolen, ocimene, γ-terpinene, α-phellandrene, p-cymene, β-caryophyllene, β-farnesene, 1,3,5-undecatriene, and diphenylmethane; alcohols such as anise alcohol, cinnamic alcohol, phenyl propyl alcohol, dimethyl benzyl carbinol, phenylethyl methyl ethyl carbinol, 3-methyl-5-phenylpentanol, orcinol monomethyl ether, isoeugenol, santalol, isobornyl cyclohexanol, "SANDALORE" (a synthetic sandalwood oil), "BACDANOL" (2-ethyl-4-(2,2,3-trimethylcyclopent-3-en-yl)-but-2-en-1-ol), "SANDALMYSORE CORE" (2-methyl-4-(2,2,3-trimethyl-3-cyclopneten-1-yl)-2-buten-1-ol), "BRAMANOL", "EBANOL" (3-methyl-5-(2,2,3-trimethyl-3-cyclopentenyl)-4-pentene-2-ol; 3-methyl-5-(2,2,3-trimethyl-3-cyclopenten-1-yl)-4-penten-2-o), "POLYSANTOL", 2-ethoxy-4-methoxymethylphenol, trans-2-hexenol, cis-3-hexenol, 3-octanol, 1-octen-3-ol, 2,6-dimethyl-2-heptanol, 9-decenol, 4-methyl-3-decen-5-ol, 10-undecenol, trans-2-cis-6-nonadienol, nerol, citronellol, rhodinol, myrcenol, lavandulol, tetrahydrogeraniol, tetrahydrolinalool, hydroxycitronellol, alloocimenol, terpinene-4-ol, isopulegol, nopol, farnesol, nerolidol, bisabolol, patchouli alcohol, 2,4-dimethyl-3-cyclohexene-1-methanol, 4-isopropylcyclohexanol, 4-isopropylcyclohexane-methanol-1-(4-isopropylcyclohexyl)ethanol, 2,2-dimethyl-3-(3-methylphenyl)propanol, p-t-butylcyclohexanol, o-t-butylcyclohexanol, ambrinol, benzyl alcohol, phenylethyl alcohol, phenoxyethanol, and styralyl alcohol; and ethers such as methyl dihydrojasmonate, tetrahydrofurfuryl 3-mercaptopropionate, kovanol, geranium oil, birch oil, Al Moise oil acetyl cedrene, amylcinnamaldehyde, allylamylglycolate, β-ionone, isobutyl quinoline, nerol oxide, myroxyde, rose oxide, limetol, menthofuran, linalool oxide, butyldimethyl dihydropyran, acetoxy amyl tetrahydropyran, cedryl methyl ether, methoxycyclododecane, 1-methyl-1-methoxycyclododecane, ethoxy methyl cyclo dodecyl ether, tricyclodecenyl methyl ether, rhubofix, cedroxide, ambroxane, grisalva, Bowajirisu, anisole, dimethylhydroquinone, p-cresyl methyl ether, acetoanisole, anethole, dihydroanethole, diphenyloxide, methyl eugenol, methyl isoeugenol, benzyl isoeugenol, phenylethylisoamylether, δ-naphthyl methyl ether, δ-naphthyl ethyl ether, δ-naphthyl isobutyl ether, 2,4-dimethyl-4-phenyltetrahydrofuran, galaxolide, and 2,2,5,5-tetramethyl-4-isopropyl-1,3-dioxane.

(Pigments)

Examples of the pigments include natural pigments such as anthraquinone, anthocyanin, chalkone, carotenoid, flavonoid, flavin, quinone, porphyrin, diketone, and pentacyanidin series of annatto, acrosin, capsanthin, shisonin, *hibiscus* color, grapeskin extract, safflower yellow, cacao pigment, laccaic acid, carminic acid, curcumin, betanin, monascorubrin, brazilin, caramel, carthamin pigment, *gardenia* pigment, *Lithospermi radix* pigment, and cochineal; photosensitizing dyes such as photosensitizing dyes 101, 201, 301, and 401; organic pigment powders of zirconium, barium, or aluminum chelate such as red Nos. 2, 3, 102, 104, 105, 106, 201, 202, 203, 204, 205, 206, 207, 208, 213, 214, 215, 218, 219, 220, 221, 223, 225, 226, 227, 228, 230, 231, and 232; orange Nos. 201, 203, 204, 205, 206, and 207; food yellow Nos. 4 and 5; FD & C green Nos. 3, 201, 202, 204, and 205; yellow Nos. 201, 202, 203, 204, 205, 401, 402, 403, 404, 405, 406, and 407; green Nos. 401, and 402; blue No. 403; violet No. 401; black No. 401, blue No. 404, red Nos. 401, 404, 405, 501, 502, 503, 504, and 506; orange Nos. 401, 402, and 403; red No. 505; blue Nos. 1, 2, 201, 202, 203, 204, and 205; brown No. 201; and violet No. 201; and mixture pigments of the above organic pigment powders incorporated with natural or organic pigments of shikon color or carthamin.

(Antisetics and Bactericides)

Examples of the antiseptics and bactericides include paraoxybenzoic acid alkyl esters such as phenol, p-chlorophenol, p-chlorometacresol, parachlorometaxylenol, resorcinol, resorcinol monoacetate, orthophenyl phenol, isobutylparaben, ethylparaben, sodium ethylparaben, butylparaben, sodium butylparaben, propylparaben, sodium propylparaben, methylparaben, and sodium methylparaben; phenols, benzoic acids, and salts thereof such as phenoxyethanol, thymol, cresol, hinokitiol, and hydroxybenzenethiol; benzoic acid and salts thereof; salicylic acid and salts thereof; sorbic acid and salts thereof; dehydroacetic acid and salts thereof; halogenated bisphenols such as 2,4,4'-trichloro-2'-hydroxydiphenylether, hexachlorophen, bithionol, and dichlorophen; amides such as 3,4,4'-trichlorocarbanilide, 3-trifluoromethyl 4,4'-dichlorocarbanilide, 3,4',5-tribromosalicylanilide, p-amino benzene sulfonamide, and undecylenic acid monoethanolamide; quaternary ammonium compounds such as benzalkonium chloride, lauryl isoquinolinium bromide, benzethonium chloride, cetylpyridinium chloride, dequalinium chloride, and alkyltrimethylammonium chloride; amphoteric surfactants such as alkylaminoethylglycine chloride, and sodium chlorostearyl hydroxyethyl betaine; chlorhexidine gluconate; tetramethylthiuram disulphide; photosensitizing dyes such as photosensitizing dyes 101, 201, 301, 401 and NK-143; alcohols such as 1-hydroxypyridine-2-thion (zinc pyrithione), imidazolidinyl urea, N-[(trichloromethyl)mercapto]-4-cyclohexene-1,2-dicarboximide, lysozyme chloride, chlorphenesin, chlorobutanol, 2-brom-2-nitro-1,3-propandiol, anise oil, seal oil, citronellol, eugenol, benzyl alcohol, ethanol, 1,3-butylene glycol, hexylene glycol, dipropylene glycol, glycerin, 1,2-propane diol, 1,2-butane diol, 1,2-pentane diol (pentylene glycol), 1,2-butane diol, 1,2-heptane diol, 1,2-octane diol, 1,2-nonane diol, and 1,2-decane diol; p-chlorometacresol, chlorhexidine hydrochloride, bis(2-pyridylthio-1-oxide)zinc, thianthol, isopropylmethylphenol, 6-acetoxy-2,4-dimethyl-m-dioxane, 5-chloro-2-methyl-4-isothiazolin-3-one, 2-methyl-4-isothiazolin-3-on, chlorine, sodium hypochlorite, chlorinated lime, iodine, formaldehyde, glutaric aldehyde, diethyl pyrocarbonate, ethylene oxide, β-propiolactone, hydrogen peroxide solution, sulfur, potassium gluconate, DMDM hydantoin, alkyl(C12-14) diethylaminoethy glycine hydrochloride, quaternium-80, quaternium-87, chloramine-T, cymen-5-ol, iodopropynyl butylcarbamate, polyaminopropyl biguanide, methylisothiazoline, methylchloroisothiazoline, and dimethylaminostyryl heptyl methyl thiazolium iodide. The following plant extracts can be advantageously used as antimicrobials; *Echinacea angustifolia* leaf extract, *Phellodendron amurense* bark extract, olive leaf extract, orange juice, *Artemisia capillaris* extract, licorice flavonoid, Sasa *veitchii* leaf extract, grapefruit extract, chlorphenesin, *Lonicera Japonica* flower extract, phenoxyethanol, *Beefsteak geranium* extract, and *Sanguisorba officinalis* extract.

Among the above antimicrobials, non-paraoxybenzoic esters such as 1,2-alkane diols and 1,3-butylene glycols are particularly preferable because of their relatively low skin irritation, high antiseptic effect, and humectancy. Examples of such 1,2-alkane diols include those with carbon atom numbers of 4 to 10 are preferable, particularly, 1,2-alkane diols selected from one or more of 1,2-pentane diol (pentylene glycol), 1,2-hexane diol, 1,2-heptane diol, and 1,2-octane diol can be advantageously used depending on their outstanding compatibilities with ascorbic acid 2-glucoside and sodium salt thereof.

(Ultraviolet Absorbing Agents)

Examples of the ultraviolet absorbing agents include p-aminobenzoic acid ultraviolet absorbing agents such as p-aminobenzoic acid, p-aminobenzoic acid monoglyceryl ester, N, N-dipropoxyparaaminobenzoic acid ethyl ester, N, N-diethoxyparaaminobenzoic acid ethyl ester, N,N-dimethylparaaminobenzoic acid ethyl ester, and N, N-dimethylparaaminobenzoic acid butyl ester; anthranilic acid ultraviolet absorbing agents such as homomenthyl-N-acetylanthranilate; benzophenone derivatives such as cinnamic acid, oxbenzone-3, oxbenzone-4, oxbenzone-5, and oxbenzone-9; saccharide ultraviolet absorbing agents wherein saccharides or sugar alcohols bind to 1,3-propanediol derivatives; salicylic acid ultraviolet absorbing agents such as salicylic acid, sodium salt thereof, amyl salicylate, menthyl salicylate, homomenthyl salicylate, octyl salicylate, phenyl salicylate, benzyl salicylate, p-isopropanolphenyl salicylate, and dipropylene glycol salicylate; cinnamic acid ultraviolet absorbing agents such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, 2-ethylhexyl p-methoxycinnamate, 2-ethoxyethyl p-methoxycinnamate (cinoxate), cyclohexyl p-methoxycinnamate, ethyl-α-cyano-β-phenylcinnamate, 2-ethylhexyl-α-cyano-β-phenylcinnamate (octocrylene), glycerylmono-2-ethylhexanoyl-diparamethoxycinnamate, and ferulic acid and its derivatives; benzophenone ultraviolet absorbing agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; dibenzoylmethane derivatives such as 3-(4'-methylbenzylidene)-d,l-camphor, 3-benzylidene-d,l-camphor, 2-phenyl-5-methylbenzoxazole, 2,2'-hydroxy-5-methylphenylbenzotriazole, 2-(2'-hydroxy-5'-t-octylphenyl)

benzotriazole, 2-(2'-hydroxy-5'-methylphenyl) benzotriazole, dibenzalazine, dianysoylmethane, 5-(3,3-dimethyl-2-norbornyliden)-3-pentane-2-on, 4-methoxy-4'-t-butylbenzoylmethane, and 4-t-butylmethoxydibenzoylmethane; urocanic acid ultraviolet absorbing agents such as octyltriazone, urocanic acid, and ethyl urocanate; hydantoin derivatives such as 2-(2'-hydroxy-5'-methylphenyl)benzotriazole, 1-(3,4-dimethoxyphenyl)-4,4-dimethyl-1,3-pentanedione, octyl dimethoxybenzylidene dioxoimidazolidine propionate, and 2-ethylhexyl dimethoxybenzylidene dioxoimidazolidine propionate; and others such as phenylbenzimidazole sulfonic acid, terephthalylidene dicamphor sulfonic acid, drometrizole trisiloxane, methyl anthranilate, rutin and derivatives thereof, oryzanol and derivatives thereof, octyldimethyl p-aminobenzoate, titanium oxide, zinc oxide, kaolin, talc, ethylhexyltriazone, octocrylene, octyl dimethyl PABA, homosalate, methylene bisbenzotriazoryl tetramethylbutyl phenol, ethylhexyl methoxycinnamate, and octyl methoxycinnamate.

(Sequestering Agents)

Examples of the sequestering agents include ethylenediaminetetraacetates such as ethylenediaminetetraacetate (EDTA), EDTA2Na, EDTA3Na, and EDTA4Na; hydroxyethylethylenediamine triacetates such as sodium salt of hydroxyethylethylenediaminetriacetates; phosphonic acid and sodium salts thereof or the like such as tripolyphosphoric acid, diethylenetriaminepentaacetates, phytic acid, and etidronicacid; poly(aminoacids) such assodiumoxalate, polyaspartic acid, and polyglutamic acid; and others such as sodium polyphosphate, sodium metaphosphate, phosphoric acid, pyrophosphate, hexametaphosphate, sodium citrate, citric acid, alanine, dihydroxyethyl glycine, gluconic acid, succinic acid, and tartaric acid.

(Buffers)

Examples of the buffers (pH-controlling agents) include citric acid, sodiumcitrate, lactic acid, sodium actate, glycollic acid, succinic acid, acetic acid, sodium acetate, potassium acetate, malic acid, tartaric acid, fumaric acid, phosphoric acid, hydrochloric acid, sulfuric acid, boric acid, borax, nitrilotriethanol, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, ammonium hydroxide, sodium hydroxide, potassium hydroxide, calcium hydroxide, magnesium hydroxide, potassium hydrogen phosphate in ammonia solution, guanidine carbonate, ammonium bicarbonate, sodium carbonate, potassium carbonate, potassium bicarbonate, sodium bicarbonate, magnesium oxide, calcium oxide, ammonium phosphate, disodium hydrogen phosphate, sodium dihydrogen phosphate, potassium phosphate, magnesium phosphate, calcium phosphate, sodium borate, sodium metaborate, and potassium citrate.

Particularly, the cosmetic lotions containing the external dermal composition of the present invention are particularly desirably used in combination with one or more buffers selected from sodium citrate, glycolic acid, succinic acid, disodium hydrogen phosphate, sodium dihydrogen phosphate, sodium hydroxide, and potassium hydroxide in an amount sufficient for adjusting the cosmetic lotions, usually, to a pH of 5 to 9, preferably, 6 to 8, more preferably, 6.5 to 7.5.

(Face-Washes)

The external dermal composition of the present invention can be made into face-washes by compounding therein ingredients having a detergent action. Face-washes are used almost every day for keeping the skin clean by washing away scurf and dirt created as a result of the physiological function inherent to the skin, i.e., an intense blend of soured or denatured sebum membranes and desquamated keratinous layers along with dirt such as dust in the air. Concrete examples of such face-washes include soaps, body shampoos, cleansing creams, make-up removers, etc. Alkaline salts (soaps) of higher fatty acids can be listed as ingredients having a detergent action; mainly, sodium, potassium, and amine salts of $C_{10}$ to $C_{18}$ fatty acids.

One or more ingredients selected from flavors, pigments, antioxidants, and sequestering agents can be further incorporated into such face-washes to improve and stabilize their quality. Such ingredients can be respectively incorporated in an amount of at least 0.0001% by mass, preferably, 0.001 to 50% by mass, more preferably, 0.01 to 25% by mass, and more further preferably, 0.1 to 10% by mass to the mass of each of the face-washes according to the present invention. As such flavors, pigments, and sequestering agents, those which are disclosed in detail in the above-mentioned paragraph on cosmetic lotions can be appropriately used. For example, the following antioxidants can be appropriately used as the above antioxidants.

(Antioxidants)

Examples of the antioxidants include vitamin A and the like as well as their derivatives and salts such as retinol, dehydroretinol, retinol acetate, retinol palmitate, retinal, retinoic acid, and vitamin A oil; carotenoid and the like as well as their derivatives such as α-carotene, β-carotene, γ-carotene, cryptoxanthin, astaxanthin, and fucoxanthin; vitamin B and the like as well as their derivatives and salts such as pyridoxine, pyridoxal, pyridoxal-5-phosphate, and pyridoxamine; vitamin D and the like as well as their derivatives and salts such as ergocalciferol, cholecalciferol, and 1,2,5-dihydroxy cholecalciferol; vitamin D and the like as well as their derivatives and salts such as α-tocopherol, β-tocopherol, γ-tocopherol, δ-tocopherol, α-tocotrienol, β-tocotrienol, γ-tocotrienol, δ-tocotrienol, tocopherol acetate, and tocopherol nicotinate; trolox and its derivatives and salts; dihydroxytoluene, butylhydroxytoluene, butylhydroxyanisole, dibutylhydroxytoluene, α-lipoic acid, dehydrolipoic acid, glutathione, and their derivatives and salts; uric acid; erythorbic acid and its derivatives and salts such as erythorbic acid and sodium erythorbate; gallic acid and its derivatives and salts such as gallic acid and propyl gallate; rutin and its derivatives and salts such as rutin and α-glycosyl rutin; tryptophan and its derivative and salts; histidine and its derivatives and salts; cysteine and its derivatives and salts such as N-acetylcysteine, N-acetylhomocysteine, N-octanoyl cysteine, and N-acetylcysteine methyl ester; cystine and its derivatives and salts such as N,N'-diacetylcystine dimethyl ester, N,N'-dioctanoylcystine dimethyl ester, and N,N'-dioctanoylhomocystine dimethyl ester; carnosine and its derivatives and salts; homocarnosine and its derivatives and salts; anserine and its derivatives and salts; carcinine and its derivatives and salts; dipeptides or tripeptide derivatives and their salts containing histidine and/or tryptophan and/or histamine; flavonoids such as flavanone, flavone, anthocyanin, anthocyanidin, flavonol, quercetin, quercitrin, myricetin, fisetin, hamamelitannin, catechin, epicatechin, gallocatechin, epigallocatechin, epicatechin gallate, and epigallocatechin gallate; tannic acid, caffeic acid, ferulic acid, protocatechuic acid, chalkone, orizanol, carnosol, sesamol, sesamin, sesamolin, zingerone, curcumin, tetrahydrocurcumin, clovamide (caffeoyldopa), deoxyclovamide, shogaol, capsaicin, vanillamide, ellagic acid, bromphenol, flavoglaucin, melanoidin, riboflavin, riboflavin butyrate, riboflavin mononucleotide, flavin adenine dinucleotide, ubiquinone, ubiquinol, mannitol, bilirubin, cholesterol, ebselen, selenomethionine, ceruloplasmin, transferrin, lactoferrin, albumin, superoxide dismutase, catalase, glutathione peroxidase, metallothionein, thioredoxin, thiotaurine, O-phosphono pyridoxyliden rhodamine, and N-(2-hyroxybenzyl) amino acid, and their derivatives and salts; N-(4-pyridoxylmethylene) amino acid, and its derivatives and salts; and others such as lysine, 1-methionine, proline, silymarin, tea extract, grape bark/seed extract, melanin, and rosemary extract.

(Other Ingredients)

In the face-washes can be further incorporated one or more ingredients selected from glycerin, ethanol, sugar (sucrose), polyalcohols, and bactericides. The antiseptics and bactericides that are disclosed in detail in the section of the above-mentioned cosmetic lotions can be appropriately used as the bactericides; however, chlorhexidine hydrochloride, isopropyl methylphenol, photosensitizing dye 101, cresol, chloroxylenol, trichlorocarbanilide, halocarban, phenol, chlorocresol, phenoxyethanol, and trichlorohydroxydiphenyl ether can be preferably used in soap-type detergents such as face-washes for the purpose of disinfection, sterilization, and deodorant.

(Serums)

The external dermal composition of the present invention can be made into serums by incorporating thereunto humectants and emollients. In general, unlike cosmetic lotions, serums are the types of cosmetics having appropriate viscosity and satisfactory humectancy and feeling of use, as well as having functions as moisturizers and emollients. The above-mentioned humectants and emollients disclosed in the section of cosmetic lotions can be appropriately used. The forms of serums are known as solubilized forms, O/W emulsion forms, and oil-liquid forms.

In general, most of serums are those which advocate an emphasis on functions other than their functions as moisturizers and emollients by further incorporating one or more ingredients selected from flavors, ultraviolet absorbing agents, skin-whitening agents, anti-inflammatories, antiseptics, and bactericides. Among the above ingredients, appropriately usable are, for example, flavors, ultraviolet absorbing agents, antiseptics, and bactericides, all of which are disclosed in the section of the above-mentioned cosmetic lotions. The following skin-whitening agents and anti-inflammatories can be appropriately used as examples of the following skin-whitening agents and anti-inflammatories.

(Skin-Whitening Agents)

Examples of the skin-whitening agents include alkoxysalicylic acid and the like as well as salts thereof such as 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-buthoxysalicylic acid, 5-methoxysalicylic acid, 5-ethoxysalicylic acid, and 5-propoxysalicylic acid; hydroquinone and derivatives thereof including hydroquinone and its glycosides such as uronic acid glycosides, for example, hydroquinone, arbutin, α-arbutin, hydroquinone α-L-glucose, hydroquinone β-L-glucose, hydroquinone α-D-galactose, hydroquinone β-D-galactose, hydroquinone α-L-galactose, hydroquinone β-L-galactose, hydroquinone α-D-ribose, hydroquinone β-D-ribose, hydroquinone α-L-ribose, hydroquinone β-L-ribose, hydroquinone α-D-arabinose, hydroquinone β-D-arabinose, hydroquinone α-L-arabinose, hydroquinone β-L-arabinose, hydroquinone α-D-glucosamine, hydroquinone β-D-glucosamine, hydroquinone α-L-glucosamine, hydroquinone β-L-glucosamine, hydroquinone α-D-galactosamine, hydroquinone β-D-galactosamine, hydroquinone α-L-galactosamine, hydroquinone β-L-galactosamine, hydroquinone α-D-glucuronic acid, hydroquinone β-D-glucuronic acid, hydroquinone α-L-glucuronic acid, hydroquinone β-L-glucuronic acid, hydroquinone α-D-galacturonic acid, hydroquinone β-D-galacturonic acid, hydroquinone α-L-galacturonic acid, and hydroquinone β-L-galacturonic acid; tranexamic acid and its derivatives and salts; resorcin and its derivatives such as 4-n-butylresorcinol; kojic acid and its derivatives and salts; ellagic and linoleic acids and their salts; plant extracts such as *Pimpinella anisum* extract, *Japanese knotweed* extract, *Daphne pseudomezereum* extract, *Senna obtusifolia* extract, seed extract of *Cassia obtusifolia* L., root extract of *Astsagalusu mambranaceus* Bge, *Astsagalusu mambranaceus* Bge extract, *Trichosanthes laceribracteata* extract, *Xanthium strumarium* extract, *Gastrodia elata* extract, *Pyracantha fortuneana* fruit extract, *Polygonum sachalinense* Fr. Schm extract, *Lindera strychnifolia* F. Vill extract, *Cucurbita* (pumpkin) extract, *Typha latifolia* L. extract, *Euphorbia kansui* Liou extract, *Agrimonia pilosa* Ledeb. var. *japonica* (Miq.) Nakai extract, *Lindera umbellata* extract, *Saxifraga fusca* var. *kikubuki* extract, *Agave sisalana* extract, *Clematis chinensis* extract, *Clematis chinensis* Osbeck extract, *Cerasus speciosa* (Koidz.) H. Ohba extract, *Cerasus sargentii* (Rehder) H. Ohba extract, *Prunus incisa* Thunb extract, *Prunus nipponica* extract, *Cerasus subhirtella* (Miq.) S.Y. Sokolov extract, *Prunus lannesiana* Wilson extract, *Aster tataricus* extract, *Trachycarpus fortunei* extract, *Iris florentina* L. extract, *Clematis terniflora* extract, *Magnolia salicifolia* extract, *Saxifraga fortunei* var. *incisolobata* extract, *Oenothera tetraptera* extract, dried seed extract of *Convolvulaceae/Cuscuta chinensis* Lam./*C. Japonica* Choisy, *Cuscuta australis* extract, *Cuscuta japonica* Choisy extract, *Artemisia absinthium* extract, *Achillea alpina* L. extract, *Dictamnus albus* extract, *Anethum graveolens* L. extract, *Reynoutria japonica* var. *terminalis* extract, *Tribulus terrestris* extract, *Pyrrosia lingua* (Thunb.) Farw extract, *Typha domingensis* extract, root extract of *Angelica dahurica*, floral blanca extract, hamula (*Brickellia cabanillesy*) extract, *Artemisia fukudo* Makino extract, *Convolvulus arvensis* extract, *Santalum album* extract, *Ganoderma lucidum* extract, *Leonurus japonicus* Houtt extract, *Salix gilgiana* Seemen extract, *Salix chaenomeloides* Kimura extract, *Salix gracilistyla* extract, *Salix integra* extract, *Salix kinuyanagi* Kimura extract, *Salix koriyanagi* Kimura extract, *Salix matsudana* Koidz. var. *tortuosa* Vilm extract, *Salix reinii* Fr. et Sav extract, *Salix sieboldiana* extract, *Toisusu urbaniana* Kimura extract, *Salix viminalis/Salix longifolia* extract, *Salix vulpina* Anderss extract, *Populus maximowiczii* A. Henry extract, dried bark extract of *Myrica rubra, Agave americana* var. *marginata* extract, *Agave americana* extract, *Agave americana* var. *marginata* extract, *Edgeworthia papyrifera* Sieb. et Zucc extract, *Enteromorpha* sp. extract, *Enteromorpha linza/compressa* extract, *Enteromorpha prolifera* extract, *Enteromorpha compressa* (Linnaeus) Nees extract, *Ulva intestinalis* Linnaeus extract, *Ulva* Linnaeus extract, *Laminaria* extract, *Laminaria Japonica* Areschoug extract, *Laminaria ochotensis* extract, *Laminaria religiosa* Miyabe extract, *Laminaria angustata* extract, *Undaria pinnatifida* extract, *Undaria undarioides* extract, *Undaria peterseniana* extract, *Sargassum fusiforme* extract, *Fucus evanescens* C. Agardh (*F. vesiculosus*) extract, *Padina arborescens* extract, *Padina australis* Hauck extract, *Padina australis* Hauck var. *cuneata* Tak. Tanaka et K. Nozawa extract, *Padina boryana* Thivy extract, *Padina crassa* Yamada extract, *Padina japonica* Yamada extract, *Padina minor* Yamada extract, *Padina stipitata* Tak. Tanaka et K.

Nozawa extract, *Eucheuma serra* (J. Agardh) J. Agardh extract, *Eucheuma amakusaense* Okamura extract, *Eucheuma denticulatum* (Burman) Collins et Hervey extract, *Eucheuma arnoldii* Weber-van Bosse extract, *Chondrus ocelatus* Holmes extract, *Chondrus verrucosus* Mikami extract, *Chondrus nipponicus* Yendo extract, *Chondrus pinnulatus* (Harvey) Okamura extract, *Gigartinales* Schmitz extract, *Chondracanthus teedii* extract, *Chondracanthus intermedius* extract, *Dictyopteris latiuscula* extract, *Dictyopteris polypodioides* extract, *Sphaerotrichia divaricata* (C. Agardh) Kylin extract, *Cymathaere* extract, *Cymathaere japonica* extract, *Sargassum hemiphyllum* Agardh extract, *Sargassum segii* extract, *Sargassum filicinum* extract, *Sargassum sagamianum* extract, *Sargassum nigrifolium* extract, *Sargassum piluliferum* (Turner) C. Agardh extract, *Sargassum tosaense* Yendo extract, *Sargassum patens* C. Agardh extract, *Sargassum thunbergii* (Mertens ex Roth) Kuntze extract, *Sargassum ringgoldianum* Harvey ssp. *Ringgoldianum* extract, *Grateloupia filicina* (Lamouroux) C. Agardh extract, *Halymenia agardhii* extract, *Sebdenia polydactyla* extract, *Grateloupia acuminata* Holmes extract, *Polyopes affinis* (Harvey) Kawaguchi et Wang extract, *Gracilaria gagas* extract, *Ceratodictyon spongiosum* Zanardini extract, *Lomentaria catenata* Harvey extract, *Lomentaria pinnata* Segawa extract, *Lomentaria pinnata* Segawa extract, *Laurencia intermedia* Yamada extract, *Laurencia undulata* extract, *Laurencia pinnata* Yamada extract, *Laurencia brongniartii* J. Agardh extract, *Odonthalia corymbifera* (Gmelin) Greville extract, *Tilia* extract, *Camotede azafran* extract, *Hibiscus* spp. extract, *Poleoverde verde* extract, *Raphanus sativus* extract, *Sargassum confusum* C. Agardh extract, *Sargassum kjellmanianum* Yendo extract, *Sargassum macrocarpum* C. Agardh extract, *Perilla frutescens* var. *crispa* extract, placenta extract, "RUSINOL" (4-n-butylresorcinol), silk extract, *Acacia* Mill extract, *Malpighia glabra* extract, *Abutilon avicennae* extract, *Betula pendula* extract, *Quercus* (gallnut) extract, *Castanea crenata* extract, *Isodon umbrosus* var. *leucanthus* f. *kameba* extract, Isodon *trzichocarpus* extract, *Rabdosia japonica* (Burm. fil.) H. Hara extract, *Oenanthe javanica* extract, *Fagopyrum esculentum* extract, *Durvillaea antarctica* extract, *Capsella bursa-pastoris* extract, *Eupatorium japonicum* extract, *Moraceae* extract, *Gardenia jasminoides* extract, *Angelica acutiloba* extract, *Sanguisorba officinalis* extract, *Sophora flavescens* extract, *Artemisia indica* var. *maximowiczii* extract, *Lonicera japonica* extract, *Phellodendron amurense* extract, *Houttuynia cordata* extract, *Poria cocos* extract, *Coix lacryma-jobi* var. *ma-yuen* extract, *Lamium album* L. var. *barbatum* extract, *Humulus lupulus* extract, *Crataegus cuneata* extract, *Eucalyptus* extract, *Achillea millefolium* extract, *Althaea* extract, *Cinnamomum loureiri* Nees extract, *Vitex rotundifolia* L. fil. extract, *Hamamelis virginiana* extract, *Morus australis* extract, *Platycodon grandiflorum* extract, *Euphorbia lathyris* L. extract, *Iris japonica* extract, *Ephedra intermedia* extract, *Cnidium officinale* Makino extract, *Aralia cordata* extract, *Bupleurum/Eryngium* extract, *Saposhnikovia divaricata* extract, *Glehnia littoralis* extract, *Scutellaria baicalensis* extract, peony root bark extract, *Paeonia lactiflora Paeonia* extract, *Geranium thunbergii* extract, *Pueraria lobata* extract, *Glycyrrhiza uralensis* root extract, *Rhus javanica* extract, *Aloe barbadensis* Miller extract *Cimicifugae rhizoma* extract, *Carthamus tinctorius* extract, green tea extract, red tea extract, *Uncaria gambir* extract, *Matricaria recutita* extract, *Persicaria tinctoria* extract, oil-soluble *Glycyrrhiza glabra* (licorice) root extract, *Cacumen Tamaricis* extract, and *Saxifraga stolonifera* extract; and others such as phenyl mercury hexachlorophene, mercuric oxide, mercurychloride, hydrogen peroxide, zinc peroxide, 2-aminophenol and derivatives thereof, ferulic acid and derivatives thereof, placenta extract, glutathion, orizanol, and butylresorcinol.

Examples of the anti-inflammatory agents, which can be incorporated into the serums of the present invention, include ingredients such as extracts derived from plants and mixtures thereof, for example, derivatives of propionic acid including betamethasone dipropionate, clobetasol propionate, fluticasone propionate, hydrocortisone-21-propionate, hydrocortisone cyclopentyl propionate, and beclomethasone dipropionate; allantoin or derivatives thereof such as allantoin, allantoin acetyl-dl-methionine, allantoin chlorohydroxy aluminum, dihydroxyaluminium allantoin, and allantoin polygalacturonic acid; glycyrrhetinic acid or derivatives thereof such as glycyrrhetinic acid, glycyrrhizinic acid, allantoin glycyrrhetinate, glyceryl glycyrrhetinate, stearyl glycyrrhetinate, glycyrrhetinyl stearate, disodium 3-succinyloxy glycyrrhetinate, dipotassium glycyrrhizinate, and monoammonium glycyrrhizinate; pantothenic acid derivatives such as pantothenic acid, pantothenyl alcohol, pantothenyl ethyl ether, benzoylpantothenyl ethyl ether, calcium pantothenate, sodium pantothenate, acetylpantothenyl ethyl ether, pantothenyl ethyl ether benzoate, and pantethine; tocopherol derivatives such as α-tocopherol, β-tocopherol, γ-tocopherol, tocopherol nicotinate, tocopherol acetate, tocopherol linoleate, tocopherol ferulate, and tocopherol phosphate; vitamin E and derivatives thereof such as tocotrienol, vitamin E acetate, and tocopherol succinate; 2-aminophenol and derivatives thereof; acetic acid derivatives such as sulindac, diclofenac, and fenbufen; pyridoxine hydrochloride, menthol, biotin, camphor, turpentine, zinc oxide, azulene, guaiazulene, and derivatives thereof; mefenamic acid and derivatives thereof; fenamic acid and derivatives thereof; phenylbutazone and derivatives thereof; indometacin and derivatives thereof; ibuprofen and derivatives thereof; biphenylcarboxylic acid derivatives; oxicam, salicylic acid, acetylsalicylic acid, naproxen, benoxaprofen, flurbiprofen, fenoprofen, indoprofen, pirprofen, carprofen, oxaprozin, pranoprofen, microprofen, tioxaprofen, suproprofen, alminoprofen, tiaprofenic acid, flufprofen, ketoprofen, and derivatives thereof; ε-aminocaproic acid, diclofenac sodium, diphenhydramine, tranexamic acid, and derivatives thereof; cortisone and esters thereof; hydrocortisone and esters thereof; adrenal cortical hormones such as prednisone and prednisolone; and others such as antihistamine, bucloxic acid, apazone, bromfenac, celecoxib, difenpiramide, diflunisal, etodolac, flufenamic acid, ketorolac, meclofenamate, mefenamic acid, meloxicam, nabumetone, piroxicam, butibufen, rofecoxib, tolmetin, ketorolac tromethamine, chlorpheniramine, diphenhydramine hydrochloride, chlorpheniramine maleate, corticosteroid, alclometasone, dexamethasone, flumetasone, hydrocortisone, hydrocortisone 21-monoester, hydrocortisone 21-acetate, hydrocortisone 21-butylate, hydrocortisone 21-valeate, hydrocortisone 17,21-diester, hydrocortisone 17,21-diacetate, hydrocortisone 17-acetate 21-butylate, hydrocortisone 17,21-dibutylate, methylprednisolone, betamethasone benzoate, diflorasone diacetate, fluocinonide, mometasone furoate, topical corticosteroid, hydroxytriamcinolone, α-methyldexamethasone, dexamethasone phosphate, clobetasol valerate, desonide, desoximetasone, desoxycorticosterone acetate, dichlorisone, diflorasone diacetate, diflucortolone valerate, fluadrenolon, fluclorolonacetonid, fludrocortison, flumetasone pivalate, fluosinolonacetonid, fluocortin butyl ester, fluocortolone, fluprednidene [fluprednylidene]acetate, flurandrenolone, halcinonide, hydrocortisone acetate, hydrocortisone butyrate, triamcinolone acetonide, cortodoxone, flucetonide, medrysone, amciafel, amcinafide, betamethasone, chloroprednisone, chloroprednisone acetate, clocortelone, clescinolone, difluprednate, flucloronide, flunisolide, fluperolone, fluprednisolone, hydrocortisone valerate, hydrocortamate, meprednisone, paramethasone, triamcinolone, isoxicam, tenoxicam, sudoxicam, CP-14, 304, *Aloe barbadensis* Miller, *Aloe vera* L., plant sterol, phytosterol, *Polygonum tinctorium, Uncaria gambir* Roxb, *Hydrangea macrophylla* var. *thunbergii, Althaea officinalis, Arnica montana* L, *Aloe barbadensis* Miller, *Polygonum bistorta* L., *Urtica thunbergiana, Rosa multiflora, Echinacea, Rabdosia japonica, Curcuma longa, Scutellaria baicalensis* Georgi, *Hordeum vulgare, Hypericum erectum, Citrus sinensis, Valeriana fauriei* Brig., *Betula, Matricaria chamomilla* L., *Daucus carota, Artemisia capillaris, Glycyrrhiza uralensis, Cucumis sativus* L., *Lonicera japonica, Commiphora* [guggal], *Gardenia jasminoides, Sasa veitchii, Nasturtium officinale, Gentiana lutea* Linn, *Geranium thunbergii, Cola, Arctium lappa* L., *Symphytum officinale, Acanthopanax senticosus* Harms, *Scrophularia buergeriana* Miq., *Salvia splendens, Zanthoxylum piperitum, Coriandrum sativum* L., *Lithospermum erythrorhizon, Perilla frutescens* var. *crispa, Paeonia lactiflora, Betula platyphylla* var. *japonica, Salvia officinalis, Hypericum perforatum, Hedera helix, Juniperus communis, Achillea millefolium, Mentha piperita* L., *Cnidium officinale* Makino, *Swertia japonica, Morus alba, Ziziphus jujuba, Thymus* L., *Coriandrum sativum, Centella asiatica* Urban, *Benincasa hispida, Amygdalus persica* L., *Houttuynia cordata, Potentilla tormentilla, Poligonum tinctorium* Lour, *Camellia sinensis, Angelica acutiloba, Calendula officinalis, Sambucus racemosa* subsp. *sieboldiana, Daucus carota* L. [carrot], *Petroselium crispum, Mentha, Santalum album, Eriobotrya japonica, Aesculus hippocastanum, Vitis labrusca, Brassica oleracea* var. *italica, Carthamus tinctorius, Typha angustifolia, Tilia miqueliana, Paeonia suffruticosa, Manjistha, Aesculus hippocastan, Sapindus mukorossi, Ellisella* sp. extract, *Tradescantia ohiensis, Oenothera biennis, Amygdalus persica* L., *Rodgersia podophylla, Eucalyptu, Artemisia indica* var. *maximowiczii, Myrica rubra, Lavandula vera, Anthemis nobilis*, and *Rosmarinus officinalis* L.

In particular, in the case of serums in which the external dermal composition of the present invention is incorporated, the following one or more ingredients of natural ingredients can be used alone or in combination as anti-inflammatory agents; glycyrrhetic acid and derivatives thereof such as stearyl glycyrrhetinate and dipotassium glycyrrhizate; and others of *Gentiana lutea* root extract, *Perilla frutescens* extract, *Salvia officinalis* extract, *Sambucus nigra* L. extract, *Centella asiatica* extract, *Houttuynia cordata* extract, *Angelica sinensis* extract, *Paeonia suffruticosa* extract, *Oenothera biennis* extract, *Sapindus mukorossi* extract, *Saxifraga stolonifera* extract, *Artemisia indica* var. *maximowiczii* extract, and *Malus pumila* extract. Usually, the above ingredients are respectively incorporated into the serums in an amount of at least 0.0001% by mass, preferably, 0.001 to 50% by mass, more preferably, 0.01 to 25% by mass, and more preferably, 0.1 to 10% by mass to the mass of each of the serums according to the present invention.

<Milky Lotion>

The external dermal composition of the present invention, which contains an aqueous medium as a base material, can be made into milky lotions by incorporating oily ingredients and surfactants. Such milky lotions are used for the purpose of washing the skin, removing make-ups, protecting the skin, humidifying and softening the skin, and accelerating the blood circulation in the skin. Milky lotions are also called "liquid creams" because, except in a special case, they have a lesser amount of oil phase than creams and are free-flowing emulsions. There are two types of O/W and W/O emulsions, of which the former is general and capable of imparting a moistened feeling to users because it has a relatively high ratio of water phase and spreads thinly, when applied to the skin. Examples of appropriately employable oily ingredients and surfactants include those which are disclosed in detail in the above section of cosmetic lotions.

One or more ingredients selected from humectants, emollients, blood circulation accelerators, and high molecular substances can be incorporated in the milky lotions according to the present invention, depending on their purposes and functions, in a respective amount of at least 0.0001% by mass, preferably, 0.001 to 50% by mass, more preferably, 0.01 to 25% by mass, and more preferably, 0.1 to 10% by mass to the mass of each of the milky lotions. Examples of such humectants and emollients include those which are disclosed in detail in the above section of cosmetic lotions. Examples of the blood circulation accelerators and high molecular substances include the following ones to be appropriately incorporated into the milky lotions.

(Blood Circulation Accelerators)

Examples of the blood circulation accelerators include plant substances such as *Swertia japonica*, Asian ginseng [*Panax ginseng*], *Ginkgo biloba, Urtica thunbergiana, Zingiber officinale, Allium sativum, Angelica keiskei, Arnica montana, Prunus armeniaca, Foeniculum vulgare, Trillium apetalon, Hypericum erectum, Ononis spinosa, Nasturtium officinale, Chaenomeles sinensis, Matricaria chamomilla* L., *Anthemis nobilis, Rubus palmatus, Cinchona Succirubra* L., *Papaver rhoeas* L., *Sophora flavescens, Gentiana lutea, Cinnamomum cassia* Blume, *Nuphar japonicum, Arctium lappa* L., *Oryzasativa, Salvia, Zanthoxylum piperitum, Crataegus cuneata, Lentinula edodes, Rehmannia glutinosa* [*R. glutinosa* var. *purpurea*], *Diospyros* spp., *Paeonia lactiflora, Zingiber officinale, Acorus calamus* var. *angustatus, Crataegus oxyacantha* var. *paulii, Aesculus hippocastanum* L., *Juniperus communis, Ligusticum chuanxiong, Citrus aurantium, Thymus* spp., *Syzygium aromaticum, Capsicum annuum, Angelica sinensis* (Oliv.) Diels, *Calendula officinalis* Linn, *Prunus persica* (L.) Batsch, *Picea, Houttuynia cordata, Juniperus oxycedrus* Linne, *Mentha* spp., *Glehnia littoralis, Hamamelis virginiana, Ruscus aculeatus* L., *Vitis* spp., *Tilia miqueliana* Maxim, *Humulus lupulus, Paeonia suffruticosa, Pinus luchuensis, Aesculus hippocastanum, Rosmarinus officinalis, Melissa officinalis, Melilotus offcinalis, Citrus junos, Eriobotrya japonica, Coix lachryma-jobi* L. *ma-yuen* Stapf, *Lavandula angustifolia, Gentiana scabra* var. *buergeri, Rosmarinus officinalis, Rosa canina*, peel of *Citrus unshiu* Markovich, *Prunus persica, Juglans mandshurica* subsp. *sieboldiana, Equisetum arvense* L., root of *Acorus calamus, Aloe barbadensis* Miller, *Myrica rubra, Eucalyptus regnans*, and *Artemisia princeps* Pampan; hesperidin; glycosyl hesperidin; rutin; glycosyl rutin; acetylcholine; capronium chloride; diphenhydramine hydrochloride; γ-oryzanol; l-menthol; cepharanthine; methyl nicotinate; vitamin E and derivatives thereof such as δ-tocopherol, α-tocopherol, tocopherol acetate, tocopheryl linoleate, tocopheryl nicotinate, tocopherol succinate, and vitamin E nicotinate; and others such as minoxidil, nicotinic-acid amide, nonanoic acid vanillylamide, and carbon dioxide.

<High Molecular Substances>

High molecular substances are in many cases generally previously added as protective colloids to water phases of milky lotions and are exemplified by carboxy vinyl polymer, xanthan gum, acrylic polymer, and sodium carboxymethyl cellulose (CMC).

<Creams>

The external dermal composition of the present invention, which contains an aqueous medium as a base material, can be formed into creams by incorporating oily ingredients and surfactants. Similarly as in milky lotions, creams have both types of O/W and W/O emulsions, however, they are emulsions with no free-flowing ability due to their enriched oil phases compared to milky lotions. Similar to such milky lotions, the use of creams aims to clean the skin, remove make-ups, protect/humidify/soften the skin, and accelerate the blood circulation in the skin. Concrete examples of such creams are cleansing creams, emollient creams, nourishing creams, night creams, base creams, vanishing creams, moisturizing creams, massaging creams, cold creams, and lip creams.

Any of the components of oily ingredients and surfactants disclosed in the above-mentioned cosmetic lotions can be appropriately used in the above creams. One or more ingredients selected from spermaceti, cetanol, lanolin, petrolatum, petrolatum, glycerin, and squalane can be further incorporated into the creams in a respective amount of at least 0.0001% by mass, preferably, 0.001 to 50% by mass, more preferably, 0.01 to 25% by mass, and further more preferably, 0.1 to 10% by mass to the mass of each of the creams according to the present invention.

<Other Ingredients>

In addition to the above-mentioned various ingredients, the following other ingredients generally used in cosmetic lotions, face-washes, beauty lotions, or creams, can be, if necessary, appropriately incorporated into the external dermal composition of the present invention or any of the cosmetic lotions, face-washes, beauty lotions, or creams according to the present invention; thickeners, vitamins, amino acids, anti-wrinkle agents, seaweed extracts, cell activators, percutaneous-absorption accelerators, foaming agents, solubilizing agents, keratolytic drugs, hormones, colorants, plasticizers, inorganic powders, and organic powders.

<Thickeners>

Examples of the thickeners include guar gum, locust bean gum, quince seed, carrageenan, galactan, gum arabic, tara gum, tamarind, furcelleran, gum karaya, *Abelmoschus manihot*, cara gum, tragacanth gum, pectin, pectinic acid, and salts thereof such as of sodium salts; alginic acid and salts thereof such as of sodium salts; starches such as mannan, rice, corn, potato, and wheat; dextrin, xanthan gum, dextran, succinoglucan, curdlan, hyaluronic acid, and salts thereof; xanthan gum, pullulan, gellan gum, chitin, chitosan, agar, brown algae extract, chondroitin sulfate, casein, collagen, gelatin, albumin, methyl cellulose, ethyl cellulose, hydroxypropyl cellulose, hydroxyethyl cellulose, carboxymethyl cellulose, and their salts such as of sodium salts; cellulose and derivatives thereof such as methyl hydroxypropyl cellulose, sodium cellulose sulfate, dialkyl dimethyl ammonium cellulose sulfate, crystalline cellulose, and cellulose powder; starch high molecules such as soluble starch, carboxymethyl starch, methyl hydroxypropyl starch, and methyl starch; starch derivatives such as starch hydroxypropyltimonium chloride, and aluminum corn starch octenylsuccinate; algin acid derivatives such as propylene glycol alginate; amphoteric methacrylate copolymers such as polyvinyl pyrrolidone (PVP), polyvinyl alcohol (PVA), vinyl pyrrolidone-vinyl alcohol copolymer, vinyl alcohol-vinyl acetate copolymer, polyvinyl methyl ether, polyethylene glycol, polypropylene glycol, polyoxyethylene-polyoxypropylene copolymer, (methacryloyloxyethyl carboxy betaine/alkyl methacrylate) copolymer, acrylates/stearyl acrylate/ethylamine oxide methacrylate copolymer; dimeticone/vinyl dimethicone crosspolymer, (alkyl acrylate/diacetone acrylamide)copolymer, (alkyl acrylate/diacetone acrylamide)copolymer AMP, partially saponified polyvinyl acetate, maleic acid copolymer, polyvinylpyrrolidone, vinylpyrrolidone-methacrylate dialkylaminoalkyl copolymer; alkanolamine acrylic resin; polyester; water-dispersible polyester; polyacrylamide; polyacrylic ester copolymers such as ethylpolycrylate; carboxy vinyl polymer; polyacrylic acid including salts thereof such as of sodium salts; acrylic acid/methacrylic acid copolymer; acrylic acid/methacrylic acid alkyl copolymer; cationized celluloses such as polyquaternium-10; diallyldimethylammonium chloride/acrylamide copolymers such as polyquaternium-7; acrylic acid/diallyldimethylammonium chloride copolymers such as polyquaternium-22; acrylic acid/diallyldimethylammonium chloride/acrylamide copolymers such as polyquaternium-39; acrylic acid/cationized methacrylate copolymer; acrylic acid/cationized methacrylamide copolymer; acrylic acid/methylacrylate/methacrylamidepropyltrimethyl-ammonium chloride copolymer such as polyquaternium-47; chlorinated methacrylic acid choline ester copolymer; cationated polysaccharides such as cationated oligosaccharides, cationated dextrans, and guar hydroxypropyltrimonium chloride; polyethylenimine; cationic polymer; 2-methacryloyloxyethyl phosphorylcholine copolymers such as polyquaternium-51; high molecular emulsions such as acrylic resin emulsion, polyacrylic acid ethyl emulsion, polyacrylalkylester emulsion, polyvinylacetate resin emulsion, natural rubber latex, and synthetic latex; cellulose nitrate, polyurethanes, and copolymers thereof; silicon copolymers such as silicons, acryl/silicon graft copolymers; fluorine high molecules; 12-hydroxystearic acid and salts thereof; dextrin fatty esters such as dextrin palmitate and dextrin myristate; hydroxystearic acid cholesteryl; silicic anhydride; fumed silica (ultrafine silicic anhydride); magnesium aluminum silicate; sodium magnesium silicate; metal soap; dialkyl phosphoric acid metal salt; bentonite; hectorite; organophilic clay minerals; sucrose fatty acid ester; fructooligosaccharide fatty acid ester; seed extract of *Cydonia oblonga*; and natural, semisynthetic, and synthetic high-molecular substances such as hydroxyethyl guar gum, carboxymethyl guar gum, starch, and carboxymethyl chitin.

<Vitamins>

Examples of vitamins include vitamin A and derivatives thereof such as retinol, retinol acetate, and retinol palmitate; thiamin hydrochloride; thiamin sulfate; riboflavin; riboflavin acetate; pyridoxine hydrochloride; pyridoxine dioctanoate; pyridoxine dipalmitate; flavin adenine dinucleotide; cyanocobalamin; folic acid and the like; nicotinic acid and the like such as nicotinic-acid amide/benzyl nicotinate; choline and the like; vitamin B and the like such as vitamin B6 hydrochloride, vitamin B6 tripalmitate, vitamin B6 dioctanoate, vitamin B12, vitamin B2, vitamin B6, vitamin B15, and derivatives thereof; tocopherol and derivatives thereof such as α-tocopherol, β-tocopherol, γ-tocopherol, tocopherol nicotinate, tocopherol acetate, tocopherol linoleate, tocopherol ferulate, and tocopherol phosphate; vitamin Es and the like such as tocotrienol, vitamin E acetate, and tocopherol succinate; vitamin Ds; vitamin H; pantothenic acid; pantethine; vitamin F; vitamin K; and flavonoids such as vitamin P and derivatives thereof; vitamin U; ferulic acid; γ-oryzanol; α-lipoic acid; orotic acid; Coenzyme Q10; and biotin.

<Amino Acids>

Examples of amino acids include valine, leucine, isoleucine, threonine, methionine, phenylalanine, tryptophan, lysine, glycine, alanine, asparagine, glutamine, serine, cysteine, cystine, tyrosine, proline, hydroxyproline, asparaginic acid, glutamic acid, hydroxylysine, arginine, ornithine, histidine, taurine, carnitine, and their sulfates, phosphates, nitrates, citrates, pyrrolidone carboxylates, and derivatives.

<Anti-Wrinkle Agents>

Examples of the anti-wrinkle agents include glycerine, vitamin A and derivatives thereof, glycolic acid, acylated glucosamine, kinetin, vitamin E and derivatives thereof, extract of *Aloe barbadensis* Miller, collagen, hyaluronic acid, peptides such as tri- and tetra-peptides, seaweed extract, horse chestnut extract, rosemary extract, and bluebottle extract.

<Seaweed Extracts>

Examples the seaweed extracts include those extracted from brown algae, red algae, green algae, and blue-green algae; extracts of Laminariaceae, *Laminariales laminariaceae, Undaria pinnatifida Suringar, Sargassum fusiforme, Gelidiaceae, Corallina, Palmata, Chondrus, Porphyra tenera, Ulvaceae, Ulva pertusa Kjellman, Ascophyllum, Fucus, Nemacystus decipiens, Cladosiphon okamuranus*, and *Himanthalia*. The above examples include extracts of hydrophytes such as *Zostera marina* L.

<Cell Activators>

Examples of the cell activators include whey, plant extracts of *Arnica montana* L., *Phellodendron amurense, Chlorella* sp., *Humulus lupulus*, and *Brassica rapa Brassica*; amino acids such as γ-aminobutyric acid and ε-aminopropionic acid; vitamins such as retinol, thiamine, riboflavin, pyridoxine hydrochloride, pantothenic acid and the like; α-hydroxylic acid and the like such as glycolic acid and lactic acid; and others such as flavonoids, saponins, allantoin, photosensitizing dyes 101, 301, 401, and NK-4 [LUMIN].

<Percutaneous-Absorption Accelerators>

Examples of the percutaneous-absorption accelerators include urea; α-hydroxylic acids such as lactic acid, fruit acid, and glycolic acid; β-hydroxylic acids such as salicylic acid; and others such as oleic acid, undecanoic acid, octanol, nonanol, menthol, thymol, limonene, dimethylsulfoxide, dodecyl methyl sulfoxide, dimethylacetamide, N,N-dimethylformamide, sodium lauryl sulfate, N,N-bis(2-hydroxyethyl)oleylamine, polyoxyethylene (20)sorbitan monooleate, dodecyldimethylammonium propanesulfonic acid, propylene glycol, polyethylene glycol, N,N-dimethyl-m-toluamide, N,N-diethyl-m-toluamide, laurocapram, 1-dodecyl azacyclohepthane-2-on, isopropyl myristate, Isopropyl palmitate, N-mono- or di-substituted p-menthane-3-carboxyamide, 2-(2-methoxy-1-methylethyl)-5-methylcyclohexanol, azacycloalkane derivatives, and cyclodextrins.

<Foaming Agents>

Examples of the foaming agents include azodicarbonamide, barium azodicarboxylate, azobisisobutyronitrile, azodicarbonic acid amide, N,N'-dinitrosopentamethylenetetramine, N,N'-dimethyl-N,N'-dinitrosoterephtalamide, trinitrotrimethyltriamine, 4,4'-oxybis(benzenesulfonyl hydrazide), p-toluene sulfonylhydrazide, diphenyl sulfone-3,3'-sulfonyl hydrazide, arylbis(sulfonyl hydrozide), p-toluylenesulfonyl semicarbazide, and 4,4'-oxybis(benzene sulfonyl semicarbazide); alkane fluorides such as trichlorofluoromethane and dichloromonofluoromethane; and others such as 5-morphoryl-1,2,3,4-thiatriazole, ammonium carbonate, ammonium hydrogen carbonate, sodium hydrogen carbonate, ammonium nitrite, sodium borohydride, and azides.

<Plasticizers>

Examples of the plasticizers include ethanol, phenoxyethanol, isopropanol, butyl alcohol, benzyl alcohol, lauryl alcohol, myristyl alcohol, cetyl alcohol, cetostearyl alcohol, stearyl alcohol, oleyl alcohol, behenyl alcohol; polyols such as ethylene glycol, diethylene glycol, triethylene glycol, polyethylene glycol, propylene glycol, dipropylene glycol, polypropylene glycol, glycerine, diglycerine, polyglycerine, glyceryl monostearate, isopropylene glycol, 1,2-buthane diol, 1,3-buthane diol, 1,4-buthane diol, 2,3-buthane diol, 1,2-penthane diol, 1,5-penthane diol, 2,3-penthane diol, 2,4-penthane diol, sorbitol, maltitol, raffinose, hexylene glycol, lauric acid diethanolamide, and fatty acid diethanolamide; cationic surfactants such as polyoxyethylenealkylphenylether, polyoxyethylenealkylether, polyoxyethylene oleyl alcohol ether, polyoxyethylene polyalcohol fatty acid ester, castor oil polyethoxylated hydrogenated, polyalcohol fatty acid ester, ethyleneglycol fatty acid ester, polyglyceryl fatty acid ester, sucrose fatty acid ester, and tetraalkylammonium salt; anionic surfactants such as alkyltrimethylammonium salt, alkylpyridinium chloride, stearyltrimethylammonium chloride, fatty acid salt, alkyl sulfate, alkylether sulfate ester, alkyl sulfate triethanolamine, sodium polyoxyethylene laurylsulfate, sodium lauryl sulfate, and sodium lauroyl glutamate; amphoteric surfactants such as those of betaine-, sulfobetaine-, or sulfoamino acid-type including lauryl dimethyl amino acetate betaine, and those of sulfobetaine type and sulfoamino acid type; silicon surfactants such as polyether-modified silicones and amino-modified silicons; and natural surfactants such as lecithin, lysophosphatidylcholine, ceramide, cerebroside, and surfactin sodium salt.

<Keratolytic Drugs>

Examples of the keratolytic drugs include glycolic acid, tartaric acid, salicylic acid, citric acid, lactic acid, pyruvic acid, gluconic acid, glucuronic acid, malic acid, oxalic acid, malonic acid, succinic acid, acetic acid, phenol, resorcin, retinoic acid, adapalene, trichloroacetic acid, 5-fluorouracil, andazelaic acid. In addition, examples of the hormones include estradiol, estrone, ethynyl estradiol, cortisone, hydrocortisone, prednisolone, cholecalciferol, estrogen, pregnenolone, and adrenocortical hormone.

<Colorants>

Examples of the colorants include body pigments such as talc, kaolin, mica, sericite, calcium carbonate, magnesium carbonate, magnesium silicate, and silicic anhydride; white pigments such as titanium oxide and zinc oxide; coloring pigments such as yellow oxide of iron, colcothar, black iron oxide, ultramarine, iron blue pigment, chromium oxide, chromium hydroxide, and carbon black; pearl pigments such as argentine, bismuth oxychloride, titanated mica, and colored titanated mica; powder pigments such as magnesium-, calcium- and aluminum-salts of stearic acid; zinc salts of lauric acid, palmitic acid, and myristic acid; and others such as starch powder, silk powder, nylon powder, polymethyl methacrylate, and polyethylene powder. Examples of the plasticizers include dibutyl phthalate, dioctyl phthalate, acetyl tributyl citrate, and camphor.

<Inorganic Powders>

Examples of the inorganic powders include calcium hydrogen phosphate, organophylic montmollironite, hydrated silica, anhydrous silicic acid, magnesium silicate, mica, bentonite, mica coated with titanium, bismuth oxychloride, zirconium oxide, magnesium oxide, zinc oxide, calcium carbonate, magnesium carbonate, iron oxide, ultramarine, iron blue, chromium oxide, calamine, zeolite, and carbon black. Additionally, examples of the organic powders include polyamide, polyester, polyethylene, polypropylene, polystyrene, polyurethane, vinyl resin, urea resin, phenol resin, fluorine resin, silicon resin, acrylic acid resin, melamine resin, epoxy resin, polycarbonate resin, divinylbenzene/styrene copolymer, and copolymers consisting of at least two different monomers thereof; and cellulose.

<Other Ingredients>

In the external dermal composition of the present invention or the cosmetic lotions, face-washes, serums, milky lotions, or creams can be incorporated the following those which can be generally used in external dermal compositions including cosmetics; antibiotics, glycosyl glycyrrhizin, glycyrrhizin, Rhododendron ferrugineum extract, Crocus/Crocus chrysanthus extract, Panicum miliaceum seed extract, Punica granatum flower extract, Alpinia katumadai seed extract, Craterellus cornucopioides fruit-body extract, Magnolia obovata Thunb. extract, Nannochloropsis extract, Terminalia bellirica extract, Vibrio alginolyticus extract, human oligopeptides, Aureobacidium pullulans culture, Aspergillus/Japanese chestnut astringent skin fermented extract, Alteromonas fermented extract, hydrolyzed yeast extract, yeast extract, yeast polysaccharide, rice fermented solution, Thermus thermophilus ferment, sake lees extract, Saccharomyces/Ca ferment, Saccharomyces/K ferment, Saccharomyces/Mg ferment, Saccharomyces/Zn ferment, Saccharomyces/marine salt ferment, Saccharomyces/xylinum/black tea ferment, Saccharomyces/Si ferment, Saccharomyces/Ge ferment, saccharomyces cerevisiae extract, Saccharomyces/Se ferment, Saccharomyces/Fe ferment, Saccharomyces/Cu ferment, Saccharomyces ferment lysate filtrate, Saccharomyces/Mn ferment, Saccharomyces ferment lysate extract, Pseudoalteromonas ferment extract, sclerotium gum, Sphingomonas extract, soybean ferment extract, soymilk ferment filtrate, Lactobacillus/Eriodictyon californicum ferment extract, Lactoacillus/olive leaf ferment extract, Lactobacillus/cocoa fruit ferment filtrate, Lactobacillus/quinoa ferment extract filtrate, Lactobacillus/rice ferment, Lactobacillus/pear juice ferment filtrate, Lactobacillus/soybean ferment extract, Lactobacillus/tomato fruit ferment extract, Lactobacillus/date fruit ferment extract, Lactobacillus/(milk/calcium/phosphorus/magnesium/zinc) ferment, Lactobacillus/Hibiscus sabdariffa flower ferment filtrate, Lactobacillus/(bean seed extract/sodium glutamate) ferment filtrate, Lactobacillus/grape juice ferment filtrate, Lactobacillus/Cucurbita pepo [pumpkin] fruit ferment extract, Lactobacillus/(Ganoderma lucidum [reishi mushroom]) extract/(Lentinus edodes [shitake mushroom] extract) ferment, Lactobacillus/lemon peel ferment extract, Lactobacillus/Wasabia japonica root ferment extract, Lactococcus ferment, Bacillus/(rice bran extract/soybean extract) ferment filtrate, Bacillus ferment, bifidobacteria ferment extract, Micrococcus lysate, yogurt filtrate, Rahnella/soy protein ferment, wine extract, β-D-glucuronic acid, α-L-iduronic acid, gelatinous material consisting of acidic polysaccharide (derived from Phallus impudicus) with three β-D-glucuronic acids linked together as a basic unit, sunflower shoot extract, Artocarpus heterophyllus (seed) extract, Euphoria longana Lam. extract, Spilanthes oleracea extract, Malus prunifolia extract, Bauhinia variegata extract, Pelargonidin extract, kinetin; ethers and ketons such as glycylproline, ethylhexylglycerin, ethoxydiglycol, oelylglycerol, gluconolactone, dicaprylyl ether, dihydroxyacetone, panthenyl ethyl ether, C16-18 hydroxyalkyl hydroxydimerdilinoleyl ether, C12-14 hydroxyalkyl hydroxydimerlinoleyl ether, and methoxyethanol; organic acids and salts thereof such as asiatic acid, aleuritic acid, sodium ursolate, oleanolic acid, guanidinium hydrochloride, aluminum citrate, sodium citrate, diammonium citrate, tri (tetramethylhydroxypiperidinol)citrate, sodium succinoyl glycyrrhetinate, dithiodiglycolate, ethanolamine dithiodiglycolate, diammonium dithiodiglycolate, sebacic acid, thioglycolic acid, ethanolamine thioglycolate, ammonium thioglycolate, thiolactic acid, ammonium thiolactate, calcium panteteine sulfonate, calcium propionate, sodium propionate, pentetic acid, pentasodium pentetate, and madecassic acid; amines such as aminomethyl propanol, aminomethyl propanediol, diisopropanolamine, cysteamine hydrochloric acid, and tetrahydroxypropylethylendiamine; proteins and nucleic acids such as deoxyribonucleic acid (DNA), potassium DNA, ribonucleic acid (RNA), sodium RNA, Prunus amygdalus var. dulcis (sweet almond) protein, aspartame, adenosine phosphate, disodium adenosine phosphate, alanyl glutamine, arginine/lysine polypeptide, undecylenoyl phenylalanine, ergothioneine, oligopeptide-6, ornithine monohydrochloride, hydrolyzed DNA, hydrolyzed RNA, hydrolyzed Prunus amygdalus var. dulcis (sweet almond) protein, hydrolyzed actin, hydrolyzed elastin, hydrolyzed casein, hydrolyzed oat protein, hydrolyzed keratin, hydrolyzed yeast protein, hydrolyzed rice protein, hydrolyzed conchiolin, hydrolyzed silk, hydrolyzed Lupinus albus protein, hydrolyzed Glycine max [soybean] protein, hydrolyzed Zea mays [corn] protein, hydrolyzed milk protein, hydrolyzed honey protein, hydrolyzed hazelnut protein, hydrolyzed jojoba protein, hydrolyzed vegetable protein, hydrolyzed royal jelly protein, Avena sativa [oat] kernel protein, glycoproteins, disodium guanylate, creatine, ceratin, Triticum vulgare [wheat] gluten, wheat protein, sarcosine, citrulline, dipalmitoyl hydroxyproline, dipeptide-2, sericin, Glycine max [soybean] protein, hexapeptide-2, hexapeptide-3, hexapeptide-9, hexapeptide-10, hexapeptide-11, pentapeptide-3, and whey protein; enzymes such as Coenzyme A, sutilains, papain, protease, bromelain, lipase, and α-glucosidase; terpenes such as menthone glycerin acetal; C30-38 olefin/(isopropyl maleate/maleic acid) copolymer; HDI/PPG/polycaprolactone crosspolymer; polyethylene glycols such as PEG-4, PEG-6, PEG-8, PEG-12, PEG-16, PEG-20, PEG-30, PEG-32, and PEG-40; propylene oxide polymers or derivatives thereof such as PPG-3 and PPG-7; VA/crotonates/vinyl neodecanoate copolymer, VP/DMAPA acrylates copolymer, VP/vinyl caprolactam/DMAPA acrylates copolymer, VP/methacrylamide/vinyl imidazole copolymer, acrylamide/ammonium acrylate copolymer, acrylamide/sodium acryloyldimethyltaurate/acrylic acid copolymer, sodium acrylate/sodium acryloyldimethyltaurate copolymer, sodium acrylate/acryloyldimethyltaurate copolymer, acrylic acrylic acid/acrylamidomethyl propane sulfonic acid copolymer, acrylic acid/alkyl acrylate C10-30 copolymer, acrylamidopropyltrimonium chloride/acrylamide copolymer, alkyl acrylate/octylacrylamide copolymer, alkyl acrylate copolymer, and derivatives thereof, alkyl acrylate/diacetone acrylamide/amodimethicone copolymer AMP, alkyl acrylate/diacetone acrylamide copolymer, alkyl acrylate/diacetone acrylamide copolymer AMP, alkyl acrylate/diacetone acrylamide copolymer AMPD, hydroxyethyl acrylate/butyl acrylate/methoxyethyl acrylate copolymer, hydroxyethyl acrylate/methoxyethyl acrylate copolymer, hydroxyethyl acrylate/sodium acryloyldimethyltaurate copolymer, acrylates/acrylamide copolymer, acrylates/C10-30 alkyl acrylate crosspolymer, acrylates/alkyl stearyl acrylate/ethylamine oxide methacrylate copolymer, acrylates/hydroxyalkyl acrylate copolymer, acrylate copolymer, carbomer, ethylene/propylene copolymer, ethylene/propylene/stylene copolymer, octylacrylamide/2-hydroxypropyl acrylate/butylaminoethyl methacrylate copolymer, synthetic wax, hydrogenated C16-14 olefin polymers, butylene/ethylene/stylene copolymer, polyacrylamide, sodium polyacrylate, and polyethylene isoterephthalate; polyoctaniums such as polyoctanium-5, polyoctanium-6, polyoctanium-7, polyoctanium-11, polyoctanium-16, polyoctanium-22, polyoctanium-28, and polyoctanium-32; synthetic high molecular compounds such as polyglucuronic acid, polydecene, polypropylsilsesquioxane, glyceryl polymethacrylate, polymethacryloyl ethyl betaine, polymethacryloyl ethyl betaine, and repagermanium; and others such as acetyl dipeptide-1 cetyl ester, acetyl tetrapeptide-2, acetyl tetrapeptide-5, acetyl hexapeptide-1, acetyl hexapeptide-3, and sodium C8-16 isoalkylsuccinyl lactoglobulin sulfonate. In addition to the above ingredients, any existing cosmetic materials can be further used; all the cosmetic materials disclosed in the following publications can be appropriately used in combination: "*Supplements to The Japanese Standards of Cosmetic Ingredients*", 2nd Edition, edited by Japan Cosmetic Industry Association, published by Yakuji Nippo Ltd., Tokyo, Japan, in 1984; "*The Japanese Cosmetic Ingredients Codex*", supervised by Evaluation and Registration Division, Pharmaceutical Affairs Bureau, Ministry of Health and Welfare, published by Yakuji Nippo Ltd., Tokyo, Japan, in 1993; "*Supplement to The Japanese Cosmetic Ingredients Codex*", supervised by Evaluation and Registration Division, Pharmaceutical Affairs Bureau, Ministry of Health and Welfare, published by Yakuji Nippo Ltd., Tokyo, Japan, in 1993; "*The Comprehensive Licensing Standards of Cosmetics by Category*", supervised by Evaluation and Registration Division, Pharmaceutical Affairs Bureau, Ministry of Health and Welfare, published by Yakuji Nippo Ltd., Tokyo, Japan, in 1993; "Japanese Pharmaceutical Codex (JPC)", supervised by Evaluation and Registration Division, Pharmaceutical Affairs Bureau, Ministry of Health and Welfare, published by Yakuji Nippo Ltd., Tokyo, Japan, in 1997; "*The Latest Cosmetic Science (revised and enlarged II)*", edited by The Society of Cosmetic Chemists of Japan, Yakuji Nippo Ltd., Tokyo, Japan, in 1992; "*Encyclopedia of Cosmetics*", edited by The Society of Cosmetic Chemists of Japan, Maruzen Co., Ltd., Tokyo, Japan in 2003; and "*Japan Cosmetic Raw Material Collection* 2007", edited by Japan Cosmetic Industry Association, published by Yakuji Nippo Ltd., Tokyo, Japan, in 2007.

C. Production Method

The external dermal composition of the present invention or cosmetic lotions, face-washes, serums, milky lotions, and creams, which contain the composition, can be produced through a step of mixing one or more ingredients selected from L-ascorbic acid, derivatives thereof, and their salts as an effective ingredient (s) with an aqueous medium as a base material. More concretely, the above products can be prepared by mixing one or more ingredients selected from L-ascorbic acid, derivatives thereof, and their salts as an effective ingredient(s) with an aqueous medium as a base material; dissolving the effective ingredient (s) in the aqueous medium; adjusting the resulting solution to give a pH of 3 to 11, desirably, a pH 5 to 9; and, before obtaining a desired final product, incorporating the solution into a product under processing at an appropriate production step according to an appropriate means depending on the type of the final product. Methods and their orders for incorporating each ingredient, as well as the timings of treatments, should not specifically be restricted as long as they do not spoil the effect and function of the present invention; and any appropriate methods and their orders conventionally used in this field can be employable.

Particularly, in the case of producing the external dermal composition of the present invention or the basic skin cares such as cosmetic lotions, face-washes, serums, milky lotions, and creams by using sodium salt of ascorbic acid 2-glucoside in a hydrous or anhydrous crystalline form, the crystalline sodium salt of ascorbic acid 2-glucoside and the anhydrous crystalline ascorbic acid 2-glucoside can be combined in an appropriate composition ratio into a composition to give a desired pH of 3 to 11, desirably, a pH of 5 to 9, when dissolved in an aqueous medium, without neutralizing these ascorbic acids with an optional alkali as in the case of using conventional anhydrous crystalline ascorbic acid 2-glucoside. It is preferable in that, according to the above-identified production method, not only a neutralization step with an optional alkali can be omitted but an increment of salt concentration due to the addition of such an alkali or buffer can be preferably reduced.

The content of one or more ingredients selected from L-ascorbic acid, derivatives thereof, and their salts in the external dermal composition of the present invention or the basic skin cares such as cosmetic lotions, face-washes, serums, milky lotions, and creams should not specifically be restricted and appropriately determined to meet their purposes; however, they are usually incorporated into a final processed product in an amount of 0.1 to 90% by mass, preferably, 0.5 to 50% by mass, more preferably, 1 to 10% by mass, and further more preferably, 5 to 10% by mass in terms of L-ascorbic acid, d.s.b., to the mass of a desired product.

Since the external dermal composition of the present invention or the basic skin cares such as cosmetic lotions, face-washes, serums, milky lotions, and creams contain one or more ingredients selected from L-ascorbic acid, derivatives thereof, and their salts, they exert an improved turnover in the skin, maintain and enhance the barrier function in the skin, and exert improved anti-ageing effects such as anti-wrinkles, anti-fine wrinkles, anti-blemishes, and anti-saggings in the skin.

The following experiments explain the present invention in more detail.

Experiment 1: Effect on Skin Turnover by Ascorbic Acid 2-Glucoside

The skin consists of "stratum corneum (or layer of corneocytes)", "stratum granulosum (or granular layer)", "stratum spinosum (or spinous layer)", and "stratum basale (or basal cell layer)" located in this order from the epidermis, and newborn epidermal cells, which are generated in the stratum basale, move sequentially toward the epidermis, mature into stratum corneum, and finally peel off. Such a series of cycle is generally called turnover, which may cause skin problems of inducing saggings, wrinkles, fine wrinkles in the skin or the like as it slows down with ageing. The following was experimented to examine the effect of ascorbic acid 2-glucoside on the above-mentioned turnover.

Experiment 1-1: Effect of Ascorbic Acid 2-Glucoside on the Proliferation of Cutaneous Cells Normal human epidermal keratinocytes from neonatal foreskin (commercialized by Kurabo Industries Ltd., Osaka, Japan, and abbreviated as "NHEK cells", hereinafter) were suspended in EpiLife medium (commercialized by Invitrogen Corporation, Calif., USA) supplemented with a cell-growth supplement (EDGS: EpiLife Defined Growth Supplement) (EpiLife medium supplemented with EDGS is abbreviated as "EpiLife medium", hereinafter), and subjected to passage cultures at a confluent density of 60 to 80% under a 5% v/v $CO_2$ condition and at 37° C. The proliferated cells were detached from culture vessels, suspended in HuMedia-KB2 medium (commercialized by Kurabo Industries Ltd., Osaka, Japan) to give a cell density of $7.5 \times 10^3$ cells/mL, inoculated to 24-well plates coated with collagen ("Cell matrix Type IV", a product name of Nitta Gelatin Inc., Osaka, Japan) in a volume of 0.4 mL/well, and cultured for one day under a 5% v/v $CO_2$ condition and at 37° C. After removing each supernatant, a solution, which had been prepared by dissolving "AA2G", a product name of a particulate composition containing anhydrous crystalline ascorbic acid 2-glucoside, commercialized by Hayashibara Co., Ltd., Okayama, Japan, in HuMedia-KB2 medium supplemented with hydrocortisone and insulin (commercialized by Kurabo Industries Ltd., Osaka, Japan, and abbreviated as "KB2-HI", hereinafter) to give a final ascorbic acid 2-glucoside concentration of 0 to 900 µM, was added to the plates in a volume of 0.6 mL/well, and cultured at 37° C. for four days in a 5% v/v $CO_2$ condition. Thereafter, the proliferated cells were fixed to the culture plates by the addition of a 25% v/v glutaraldehyde solution in a volume of 60 µL/well, followed by removing each supernatant, washing the cells with distilled water, adding to the cells a methylene blue solution in a volume of 0.24 mL/well to effect nuclear staining. Then, the resulting cells were washed with distilled water and admixed with 0.33 N hydrochloric acid in a volume of 0.5 mL/well to extract the dye (methylene blue), followed by transferring the resulting extract to 96-well plates in a volume of 0.1 mL/well for measuring the absorbance at wavelengths of 595 nm and 650 nm. The values, obtained by subtracting the absorbance at a wavelength of 650 nm from that of 595 nm, were regarded as indexes of cell growth rates, which were relatively evaluated by regarding the value, as a control, obtained with KB2-HI medium free of ascorbic acid 2-glucoside as 100%. The results are in Table 1.

TABLE 1

| Concentration of ascorbic acid 2-glucoside (µM) | Cell growth rate (%) |
|---|---|
| 0 | 100 |
| 100 | 148 |
| 300 | 157 |
| 900 | 169 |

As found in Table 1, ascorbic acid 2-glucoside exhibited relatively strong cell growth promoting effects on NHEK cells with increased cell growth rates of 148% at 100 µM, 157% at 300 µM, and 169% at 900 µM as the increase of ascorbic acid 2-glucoside concentration. The result indicates that ascorbic acid 2-glucoside promotes the growth of epidermal cells in the skin to improve the skin turnover, and this results in reducing the generation of wrinkles and fine wrinkles. For reference, the above action can be said to be of L-ascorbic acid because ascorbic acid 2-glucoside releases L-ascorbic acid via the action of an intracellular enzyme in the NHEK cells used in the experiment. The same applies to the following Experiment 1-2.

Experiment 1-2: Effect of Ascorbic Acid 2-Glucoside on the Expression of Proliferation Marker Proteins of Cutaneous Cells Involucrin and filaggrin are recently focused on as proliferation marker proteins of cutaneous cells. It was examined the effect of ascorbic acid 2-glucoside on the expression of these proliferation marker proteins.

Normal human epidermal keratinocytes from neonatal foreskin (NHEK cells) were prepared into $2.5 \times 10^5$ cells/mL with EpiLife medium, inoculated to 12-well plates in a volume of 1 mL/well, and cultured at 37° C. for one day under a 5% v/v $CO_2$ condition. Thereafter, each supernatant was removed, and a medium, to which ascorbic acid 2-glucoside had been added to give a final concentration of 300 or 600 µM, was added to the resulting cells in a volume of 1 mL/well, followed by culturing the cells at 37° C. for two days under a 5% v/v $CO_2$ condition. Another cell culture system, which had been similarly cultured in a medium free of ascorbic acid 2-glucoside, was provided as a control. The cells cultured with ascorbic acid 2-glucoside were further added with a medium supplemented with the same concentration of sodium salt of ascorbic acid 2-glucoside as that in the above medium in a volume of 1 mL/well, and cultured for another three days under the same conditions. After removing each supernatant, the resulting cells were washed with phosphate buffered saline (PBS), lysed with a buffer for cell extraction (20 mM Tris-HCl buffer (pH 8.0) containing a protease inhibitor, 2% w/v SDS, and 1 mM EDTA), allowed to react for 20 min under an ice-chilling condition, and extracted proteins ultrasonically with "SONIFIER™", an ultrasonic processor (commercialized by Branson Ultrasonics, Emerson Japan Ltd., Kanagawa, Japan). Each of the resulting extract was centrifuged to collect a supernatant, and a part of which was subjected to protein quantification. The remaining supernatant was admixed with a quadruple strength sample buffer [250 mM Tris-HCl buffer (pH 6.8) containing 50 mM dithiothreitol (DTT), 40% w/v glycerin, and 0.02% w/v bromphenol blue] in a 1/3 volume of the supernatant, and incubated at 99° C. for five minutes for use as a sample for Western analysis. The sample thus obtained was placed on a SDS-polyacrylamide gel in an amount of 20 µg protein/lane and subjected to SDS-polyacrylamide gel electrophoresis in usual manner, followed by transferring the proteins in the gel to a polyvinylidene difluoride (PVDF) membrane in usual manner and blocking the transferred proteins by soaking the membrane in "BLOC ACE", commercialized by DS Pharma Biomedical Co., Ltd., Osaka, Japan. The PVDF membrane was soaked in a solution with an anti-involucrin antibody or anti-filaggrin antibody, commercialized by Santa Cruz Biotechnology, Inc., Texas, USA, which had been diluted by 100-fold with a 50 mM TBS buffer [200 mM NaCl solution containing 50 mM Tris-HCl (pH 7.4)] with 10% v/v "BLOCK ACE" (called "TBS buffer", hereinafter) at ambient temperature for an hour, followed by washing the membrane with 50 mM TBS buffer containing 0.05% v/v Tween 20 to remove excessive amounts of the antibody. The PVDF membrane was soaked in an HRP-labeled anti-mouse IgG rabbit polyclonal antibody, commercialized by DAKO Japan Inc., Tokyo, Japan, at ambient temperature for two hours. The resulting membrane was washed with a 50 mM TBS buffer containing 0.05% v/v Tween 20 for 30 min and subjected to detect the proliferation marker proteins using "ECL Prime Western Blotting Detection System", a commercialized Western Blotting Detection Kit, produced by GE Healthcare Bioscience, Calif., USA; and subjected to an image analysis using "ImageJ", an open source software explored by NIH. The expression levels of the respective proteins were calibrated with "α-Tubulin", as an internal standard, into relative expression levels against the expression level of "α-Tubulin", where the expression level of control was regarded as 50%, and compared each other. The results are in Table 2.

TABLE 2

| Concentration of ascorbic acid | Relative expression level (%) | |
|---|---|---|
| 2-glucoside (μM) | Involucrin | Filaggrin |
| 0 | 50 | 50 |
| 300 | 74 | 65 |
| 600 | 84 | 71 |

As shown in Table 2, both the expression levels of involucrin and filaggrin as proliferation marker proteins were enhanced depending on the ascorbic acid 2-glucoside concentration. The above results indicate that ascorbic acid 2-glucoside functionally accelerates the differentiation of skin epidermal cells, showing that cosmetics containing ascorbic acid 2-glucoside have an advantageous improving action on skin turnover.

Experiment 2: Anti-Blemish Action by Ascorbic Acid 2-Glucoside

Sixteen female volunteers (37- to 55-year-old) were allowed to apply a cream containing ascorbic acid 2-glucoside with the following composition on their pigmented parts (blemish parts), as testing parts, generated in their faces twice a day (morning and night) at a dose of two grams per once for 90 days. On the day before applying the cream and on 45 and 90 days after the application, the color tone of a testing part in each volunteer was measured with the Pantone Color Formula Guide, No. 747XR, and the skin brightness (L* value) in each volunteer's testing part was measured by using "CR-200", a colorimeter commercialized by Minolta Co., Ltd., Tokyo, Japan. The measured values of 16 volunteers were averaged. The results are in Table 3.
<Composition of Test Cream>

| Ingredients | Parts by mass |
|---|---|
| <Phase A> | |
| Water | 53.29 |
| 2% w/v Carbomer solution | 15.0 |
| Disodium EDTA | 0.1 |
| Glycereth-26 | 3.0 |
| <Phase B> | |
| Tri(capryl/capric acid)glyceryl | 5.0 |
| Alkylbenzoic acid (C12-15) | 7.5 |
| Cyclopentasiloxane and cyclohexasiloxane | 3.0 |
| Dimethicone | 0.5 |
| Stearic acid | 2.5 |
| Glyceryl stearate | 2.0 |
| Cetearyl alcohol | 1.75 |
| <Phase C> | |
| Triethanolamine | q.s. |
| <Phase D> | |
| "AA2G", a product name of a particulate composition containing anhydrous crystalline 2-glucoside, commercialized by Hayashibara Co., Ltd., Okayama, Japan | 2.0 |

-continued

| Ingredients | Parts by mass |
|---|---|
| <Phase E> | |
| Propylene glycol 56% v/v, diazolidinyl urea 30% v/v, methylparaben 11% v/v, and propylparaben 3% v/v | 1.0 |

Phase A was kneaded while heating and Phase B was also kneaded while heating, and then the latter phase was added to the former. To the mixture was added Phase C and cooled, followed by adding Phases D and E to the resulting mixture before adjusting to pH 6.5 with triethanolamine.

TABLE 3

| Application period of cream (day) | L* Value of blemish part |
|---|---|
| 0 | 56 |
| 45 | 58 |
| 90 | 60 |

As shown in Table 3, the L* values (skin brightness) of the testing parts increased and the pigmented parts became pale depending on the days of application period. In general, unlike suntans, blemishes do not disappear with time, and therefore the above results indicate that ascorbic acid 2-glucoside has an effect of paling pigmented parts of the skin and improving blemishes.

Experiment 3: Effect of Ascorbic Acid 2-Glucoside on the Production of Glutathione (1)

Glutathione, which is a peptide that functions as an anti-oxidation component and a coenzyme in living bodies, exists generally in an oxidized form, and exerts its functions after being converted into its reduced form by an enzyme. Accordingly, it is desirable to increase the level of glutathione in living bodies, and the reduction of glutathione level is known to be a factor of ageing. An experiment to examine the effect of ascorbic acid 2-glucoside on the production of glutathione was conducted by using A431 cells (JCRB0004, Health Science Research Resources Bank, Osaka, Japan), a human cell line derived from an epidermoid carcinoma (abbreviated as "A431 cells", hereinafter). The method was carried out as follows:
<Test Solution>
To Dulbecco's MEM medium, containing 10% v/v calf fetal serum and an antibiotic (abbreviated as "D-MEM", hereinafter), were added ascorbic acid 2-glucoside, a reagent grade specimen commercialized by Hayashibara Co., Ltd., Okayama, Japan, or L-ascorbic acid, a special reagent grade specimen commercialized by Wako Pure Chemical Industries, Ltd., Tokyo, Japan, to give final concentrations of 1.0 mM or 2.0 mM for use as test solutions.
<Assay for Quantifying the Production Level of Glutathione in A431 Cells>
Continuously-cultivated A431 cells in D-MEM medium were collected, resuspended in D-MEM medium, inoculated to culture plates with 10 cm in diameter (φ) in an amount of $1 \times 10^6$ cells/10 mL/plate, and cultured for 24 hours. Thereafter, the culture supernatants were removed by sucking, and the remaining cells were added with any of the test solutions in an amount of 10 mL/plate and cultured for another 24 hours. As a control, cells were added with only D-MEM medium in an amount of 10 mL/plate and cultured for 24 hours. To each plate, which had been removed its culture supernatant, was added ice-chilled Dulbecco's PBS (−) commercialized by Nissui Pharmaceutical Co., Ltd., Tokyo, Japan, to wash cells, which were then collected with a scraper. Glutathione was quantified with "Glutathione Assay Kit", a commercially available glutathione assay kit commercialized by BioVision, Inc., San Francisco, USA. In this experiment, the control and test solutions were respectively assayed by using three plates respectively, and the data were averaged for obtaining a glutathione production level for each plate. A 5% v/v $CO_2$ incubator was used for culturing A431 cells in any case. Relative values of test samples were determined with the proviso that the production levels of reduced glutathione and total glutathione levels in A431 cells that had been cultured with only D-MEM medium were respectively regarded as 100%, and the results are in Table 4.

TABLE 4

| Sample | Concentration (mM) | Reduced glutathione (%) | Total glutathione (%) |
|---|---|---|---|
| With no addition (Control) | — | 100 | 10 |
| L-Ascorbic acid | 1 | —* | —* |
| Ascorbic acid 2-glucoside | 1 | 123 | 106 |
| | 2 | 157 | 131 |

*Not determined due to cytotoxicity

As shown in Table 4, cytotoxicity was induced in the cells cultured in D-MEM medium supplemented with 1.0 mM L-ascorbic acid, and the production levels of reduced glutathione and total glutathione in A431 cells could not be measured. Supplementarily, when 0.1 mM L-ascorbic acid was added as an upper limit concentration that does not induce cytotoxicity under the above conditions, the production levels of reduced glutathione and total glutathione in A431 cells were respectively 103% and 102% as being substantially the same as those with no addition, and no increment of glutathione production level by L-ascorbic acid was found.

On the contrary, in the case of A431 cells cultured in a D-MEM medium supplemented with 1.0 mM or 2.0 mM ascorbic acid 2-glucoside, total glutathione production levels increased to 115% and 508% respectively, revealing that a production enhancement of total glutathione production level was observed depending on the additional amount of ascorbic acid 2-glucoside. The reduced glutathione production levels were respectively 313% and 6816%, revealing that an enhancement of reduced glutathione production level was observed depending on the additional amount of ascorbic acid 2-glucoside. The fact that the reduced glutathione gave a higher increased rate than that of the total glutathione means that the production level of reduced glutathione was particularly increased. It can be speculated that, in A431 cells, L-ascorbic acid is released from ascorbic acid 2-glucoside to an extent that it does not induce cytotoxicity, while exerting a glutathione production enhancement effect.

Experiment 4: Effect of Ascorbic Acid 2-Glucoside on Glutathione Production (2)

An experiment for examining the effect of ascorbic acid 2-glucoside on glutathione production was conducted with normal human epidermal keratinocytes from neonatal foreskin, i.e., NHEK cells, commercialized by Kurabo Industries Ltd., Osaka, Japan (abbreviated as "NHEK cells", hereinafter). The method was as follows:

<Test Solutions>

Test solutions were prepared by dissolving ascorbic acid 2-glucoside (a reagent grade specimen commercialized by Hayashibara Co., Ltd., Okayama, Japan) or L-ascorbic acid (a special reagent grade specimen commercialzied by Wako Pure Chemical Industries, Ltd., Tokyo, Japan) in EpiLife medium as used in Experiment 1-1 to give a final concentration of 0.5, 1.0 or 2.0 mM.

<Assay for Quantifying the Production Level of Glutathione in NHEK Cells>

Continuously-cultivated NHEK cells in EpiLife medium were collected, resuspended in EpiLife medium, inoculated to culture plates with 10 cm in diameter in an amount of $1\times10^6$ cells/10 mL/plate, and cultured for 24 hours. Thereafter, each culture supernatant was removed by sucking, and any of the test solutions was added to the remaining cells in a volume of 10 mL/plate, followed by culturing the cells for another 24 hours. As a control, cells were added with only D-MEM medium in an amount of 10 mL/plate and cultured for 24 hours. Each culture supernatant was removed from each plate, then ice-chilled Dulbecco's PBS (−), commercialized by Nissui Pharmaceutical Co., Ltd., Tokyo, Japan, was added to rinse the remaining cells, which were then collected with a scraper. Glutathione was quantified on "Glutathione Assay Kit", a product name of glutathione assay kit commercialzied by BioVision, Inc., San Francisco, USA. In this experiment, the control and test solutions in respective three plates were assayed for glutathione production level for each plate and averaged for obtaining the glutathione production level of each solution. A 5% v/v $CO_2$ incubator was used for culturing NHEK cells in any case. Relative values of test samples were determined with the proviso that the production levels of reduced glutathione and total glutathione in NHEK cells that had been cultured with only EpiLife medium were respectively regarded as 100%, and the results are in Table 5.

TABLE 5

| Sample | Concentration (mM) | Reduced glutathione (%) | Total glutathione (%) |
|---|---|---|---|
| With no addition (Control) | — | 100 | 100 |
| L-Ascorbic acid | 0.5 | —* | —* |
| Ascorbic acid 2-glucoside | 0.5 | 106 | 106 |
| | 1.0 | 111 | 111 |
| | 2.0 | 117 | 117 |

*Not determined due to cytotoxicity

As shown in Table 5, the production levels of reduced glutathione and total glutathione in NHEK cells could not be assayed due to cytotoxicity induced in EpiLife medium with 0.5 mM L-ascorbic acid. Supplementarily, when the upper limit concentration that does not induce cytotoxicity in the above conditions, i.e., 0.1 mM L-ascorbic acid, was added to EpiLife medium, the total and the reduced glutathione production levels in NHEK cells were respectively 103% and 102% as being substantially the same as those with no addition of L-ascorbic acid or ascorbic acid 2-glucoside, and no increment of glutathione production level by L-ascorbic acid was found.

On the contrary, in the case of NHEK cells cultured in EpiLife medium with any of 0.5, 1.0, and 2.0 mM ascorbic acid 2-glucoside, the total glutathione production levels were respectively 106%, 111%, and 117%, revealing that a production enhancement of total glutathione was observed depending on the supplemented amount of ascorbic acid 2-glucoside. While, in the case of NHEK cells cultured in EpiLife medium with any of 0.5, 1.0, and 2.0 mM ascorbic acid 2-glucoside, the reduced glutathione production levels were respectively 106%, 111%, and 117%, revealing that a production enhancement of reduced glutathione was observed depending on the supplemented amount of ascorbic acid 2-glucoside. The degrees of the increased rates of reduced glutathione are substantially the same as those of the total glutathione, indicating that the production levels of total glutathione have increased without decreasing the production levels of reduced glutathione. It can be speculated that, similarly as in the case of A431 cells in Experiment 3, L-ascorbic acid is released from ascorbic acid 2-glucoside also in the case of NHEK cells to an extent that does not induce cytotoxicity, resulting in exerting a glutathione production enhancement effect.

The results in Experiments 3 and 4 indicate that ascorbic acid 2-glucoside has a remarkable action of enhancing the total glutathione production and the reduced glutathione production, and it can be used as a production enhancer for total glutathione or reduced glutathione to inhibit the ageing of living bodies through the action.

Experiment 5: Effect of Ascorbic Acid 2-Glucoside on Dickkopf-1 Production

An experiment, which examines the effect of ascorbic acid 2-glucoside on the production of Dickkopf-1 (abbreviated as "DKK1", hereinafter), which had been known to have an action of inhibiting the formation and the accumulation of melanin as a causative of blemish, was conducted as follows by using NHDF cells, normal human dermal fibroblasts, commercialized by Kurabo Industries Ltd., Osaka, Japan, capable of producing DKK1.

<Effect of Ascorbic Acid 2-Glucoside on the Production of DKK1 in NHDF Cells>

NHDF Cells, which had been diluted with a culture medium to give a cell density of $1 \times 10^4$ cells/well, were inoculated to 96-well plates. At 24 hours after the inoculation, the supernatant in each well of the plates was removed, followed by adding ascorbic acid 2-glucoside to each well of the plates to give a final concentration of 0.5, 1, 2, 4, or 8 mM. As a control, a cell culture system with no addition of ascorbic acid 2-glucoside was provided. At the first and third days of culturing after the addition of ascorbic acid 2-glucoside, the supernatant in each well of the plates was collected and quantified (n=3) for DKK1 with "RayBio", a product name of an ELISA for DKK1 assay, commercialized by RayBiotech Inc., Georgia, USA. Statistical analysis of the data was performed by t-test (see "*Kiso-Tokeigaku* (Basic Statistics) III Statistics of Natural Science", page 187, 2008, edited by University of Tokyo Press). The results are in Table 6.

TABLE 6

| Concentration of ascorbic acid 2-glucoside (mmol/L) | DKK1 Production level (ng/mL) | |
|---|---|---|
| | First day | Third day |
| 0 | 0.115 ± 0.012 | 0.217 ± 0.021 |
| 0.5 | 0.117 ± 0.018 | 0.317 ± 0.035** |
| 1 | 0.129 ± 0.017 | 0.315 ± 0.042* |
| 2 | 0.149 ± 0.037 | 0.339 ± 0.030** |
| 4 | 0.146 ± 0.016* | 0.392 ± 0.014** |
| 8 | 0.179 ± 0.032* | 0.413 ± 0.033** |

*$p < 0.05$
**$p < 0.01$

As shown in Table 6, ascorbic acid 2-glucoside significantly accelerated the DKK1 production from NHDF cells in a concentration-dependent manner and in a cultivation-time-dependent manner based on the relationship between the DKK1 production level at the first culture day and that at the third culture day.

The results in this experiment lead to an assumption that ascorbic acid 2-glucoside promotes the DKK1 production when administered to living bodies, resulting in inhibiting the melanin production by melanocytes and the transportation of melanosomes into keratinocytes, as well as in exerting the anti-blemish action and the skin-whitening action. Since ascorbic acid 2-glucoside is hydrolyzed into L-ascorbic acid and D-glucose by the action of an in vivo enzyme to exert the functions inherent to L-ascorbic acid per se, derivatives of L-ascorbic acid other than ascorbic acid 2-glucoside, salts of L-ascorbic acid, and salts of L-ascorbic acid derivatives can be speculated to promote the DKK1 production when administered to living bodies, inhibit the melanin production in melanocytes and the transportation of melanosomes into keratinocytes, and exert an anti-blemish action and a skin-whitening action. Particularly, crystals of ascorbic acid 2-glucoside and sodium salt thereof can be most suitably used as an ingredient for enhancing the DKK1 production because they are more stable than L-ascorbic acid and hydrolyzed in vivo to release L-ascorbic acid and exert the functions inherent to L-ascorbic acid per se.

Experiment 6: Effect of Ascorbic Acid 2-Glucoside on the Activation of Microphthalmia-Associated Transcription Factor Microphthalmia-associated transcription factor (abbreviated as "MITF", hereinafter) is a protein that is specifically expressed in mast cells, osteoclastic cells, pigment cells, and myocardial cells, as well as being activated by phosphorization and involved in the expression of proteins relating to melanoytes and allergic diseases. By inhibiting allergic diseases and abnormal proliferation of melanocytes through the inhibition of MITF activation, an inhibition of skin problem and a skin-whitening effect can be expected. Using B16 cells, a mouse melanoma cell line (abbreviated as "B16 cells", hereinafter), the effect of ascorbic acid 2-glucoside on the activation of MITF was experimented as follows.

<Test Solutions>

Test solutions were prepared by dissolving ascorbic acid 2-glucoside (a reagent grade specimen commercialized by Hayashibara Co., Ltd., Okayama, Japan) or L-ascorbic acid (a special reagent grade specimen commercialized by Wako Pure Chemical Industries, Ltd., Tokyo, Japan) in Dulbecco's MEM medium supplemented with 10% v/v fetal calf serum and an antibiotic (abbreviated as "D-MEM medium", hereinafter) to give a final concentration of 2.0 or 8.0 mM.

<Assay for Quantifying MITF Production Level in B16 Cells>

Continuously-cultivated B16 cells in D-MEM medium were collected, resuspended in D-MEM medium, inoculated to 6-well plates in an amount of $1 \times 10^5$ cells/2 mL/well, and cultured for 24 hours. Thereafter, the culture supernatants were removed by sucking, and any of the test solutions was added to each plate in a volume of 2 mL/well, followed by culturing the cells for two hours. As a control, cells in other plates were added with only D-MEM medium in a volume of 2 mL/plate and cultured for two hours. To each plate, which had been removed its culture supernatant, an ice-chilled Dulbecco's PBS (−), commercialized by Nissui Pharmaceutical Co., Ltd., Tokyo, Japan, was added to wash cells, and the resulting cells were added with a SDS-sample buffer containing 62.5 mM Tris-HCl (pH 6.8), 2% w/v SDS, 10% w/v glycerol, 50 mM dithiothreitol (DTT), and 0.01% w/v bromophenol blue in a volume of 0.1 mL/well, and collected with a scraper. The resulting cell suspension was treated with an ultrasonicator, commercialized by Osminics Inc., Minnesota, USA, and subjected to SDS-polyacrylamide gel electrophoresis. The proteins in the gel were electrically transferred to a nitrocellulose membrane and allowed to sequentially react with a first antibody (Anti-phospho-MITF (Ser473) or Anti MITF), a secondary antibody, and LumiGLO™ in this order, followed by allowing to expose an X-ray film for detecting MITF positive bands. The bands thus detected were subjected to band strength analysis using Scion Image to determine the quantity of MITF and phosphorylated MITF. For every B16 cell culture, a 5% v/v $CO_2$ incubator was used. Relative amounts of MITF and phosphorylated MITF and the ratio of phosphorylated MITF against MITF were determined when the level of β-actin in B16 cells upon culturing with each of the test solutions was regarded as 100%. The results are in Table 7.

TABLE 7

| Sample | Concentration (mM) | Phosphorylated MITF (%) | MITF (%) | (Phosphorylated MITF)/(MITF) |
|---|---|---|---|---|
| With no addition (Control) | — | 73 | 81 | 0.90 |
| L-Ascorbic acid | 2.0 | —* | —* | —* |
| Ascorbic acid 2-glucoside | 2.0 | 59 | 99 | 0.60 |
| | 8.0 | 36 | 101 | 0.36 |

*Not determined due to cytotoxicity

As shown in Table 7, D-MEM medium supplemented with 2.0 mM L-ascorbic acid induced cytotoxicity and this enabled the quantification of MITF in B16 cells. The ratio of phosphorylated MITF against MITF in B16 cells, which had been cultured in D-MEM medium with no addition of ascorbic acid 2-glucoside, as a control, was 0.90.

On the contrary, B16 cells, which had been cultured with D-MEM medium supplemented with 2.0 or 8.0 mM ascorbic acid 2-glucoside, gave the respective ratios of phosphorylated MITF against MITF of 0.60 and 0.36, where the inhibition of phosphorylization of MITF was observed depending on the additional amount of ascorbic acid 2-glucoside. These experimental results suggest that ascorbic acid 2-glucoside has a remarkable action of inhibiting the phosphorylization of MITF and functions as an ingredient that inhibits skin problem and whitens the skin through the inhibition of activating MITF by phosphorization.

Experiment 7: Effect of Ascorbic Acid 2-Glucoside on the Production of Cornified Envelope (CE) in Keratinous Layer and the Production of Tight Junction (TJ) Related Proteins as Cell-Cell Adhesion Structures In this experiment, the effect of ascorbic acid 2-glucoside on the production of CE, which is known to protect the interior of corneocytes present in the outermost layer thereof, and proteins relating to TJ (called "TJ-related proteins", hereinafter), which are present in a granular layer of epidermis and known as cell-cell adhesion structures, at cellular level was researched in view of the fact that CE and TJ-related proteins have a key to forming a barrier function in the skin (see Bikle D D et al., *Molecular and Cellular Endocrinology*, Vol. 177, pp. 161 to 171, 2001, and Takuo Yuki et al., *Experimental Dermatology*, Vol. 16, pp. 324 to 330, 2007). The above literatures disclose that calcium (Ca) enhances the production of CE and TJ-related proteins and improves the barrier function in the skin.

Experiment 7-1: Effect of Ascorbic Acid 2-Glucoside on the Production of CE in Keratinous Layer The following experiment was conducted to examine the effect of ascorbic acid 2-glucoside on the production of CE in a keratinous layer. As a model for typical normal human epidermal cells, normal human epidermal keratinocytes from neonatal foreskin, commercialized by Kurabo Industries Ltd., Osaka, Japan, and abbreviated as "NHEK cells", hereinafter, were suspended in EpiLife medium (pH 7.4), commercialized by Invitrogen Corporation, Calif., USA, and called "EpiLife medium", hereinafter, inoculated to 12-well microplates at a cell density of $1 \times 10^5$ cells/well, and cultured under the conditions of 37° C. and 5% v/v $CO_2$ overnight. Thereafter, "AA2G", a product name of a particulate composition containing anhydrous crystalline ascorbic acid 2-glucoside, commercialized by Hayashibara Co., Ltd., Okayama, Japan, was added to each well to give a final concentration of 0.5 or 1 mM, or, as a positive control, $CaCl_2$ was added to each well to give a final concentration of 1 mM; and the cells in each well were cultured at 37° C. for five days while replacing the medium in each well with a fresh preparation of EpiLife medium having the above-identified concentration of ascorbic acid 2-glucoside or $CaCl_2$. Assay for intracellular CE content was carried out in accordance with Tatsuya Hasegawa et al., "*Lipids*", Vol. 46, pp. 529 to 535, 2011. After completion of the culture, the culture supernatant in each well was immediately removed, followed by detaching and extracting the cells adhered to the wall of each well by means of pipetting with phosphate buffered saline (PBS, pH 7.4) containing 2% w/v sodium dodecyl sulfate (SDS), and collecting insoluble fractions by centrifugation at 15,000 rpm for 10 min. The insoluble fractions thus obtained were admixed with SDS and 1,4-dithiothreitol (DTT) to give respective concentrations of 2% w/v and 20 mM, solubilized by boiling for two hours, and sampled for measuring their optical densities (OD) at a wavelength of 310 nm on a spectrophotometer after adjusting the sample to give a protein concentration of 1 mg/mL. The measured values were regarded as CE production levels. Also, a culture system, where cells are cultured similarly as above, was provided, except for not adding ascorbic acid 2-glucoside. The results are in Table 8.

TABLE 8

| | $OD_{310nm}$ Value (CE Production level) |
|---|---|
| With no addition (Control) | 0.63 ± 0.07 |
| Ascorbic acid 2-glucoside (0.5 mM) | 0.78 ± 0.05 |
| Ascorbic acid 2-glucoside (1 mM) | 1.04 ± 0.11 |
| $CaCl_2$ (1 mM) | 1.07 ± 0.07 |

As shown in Table 8, ascorbic acid 2-glucoside was revealed to have a CE production inducibility in epidermal keratinocytes, similarly as the positive control $CaCl_2$; and it was also revealed to increase the CE production level in a dose-dependent manner.

The experiment results lead to an estimation that ascorbic acid 2-glucoside effectively induces the production of CE in keratinous layer that plays an important role in the skin barrier function, resulting in maintaining or enhancing the skin barrier function which possibly decreases with ageing.

Experiment 7-2: Effect of Ascorbic Acid 2-Glucoside on the Production of TJ-Related Proteins that Constitute Cell-Cell Adhesion Structures The following experiment was conducted to examine the effect of ascorbic acid 2-glucoside on the production of TJ-related proteins that constitute cell-cell adhesion structures by focusing on occludin and ZO-1 that are focused on as TJ-related proteins known to exist in a granular layer of epidermis: As a model for typical normal human epidermal cells, NHEK cells were suspended in EpiLife medium (pH 7.4); inoculated to 12-well microplates at a cell density of $1 \times 10^5$ cells/well; cultured overnight under the conditions of 37° C. and 5% v/v $CO_2$; and further cultured for three days under the conditions of 37° C. and 5% v/v $CO_2$ after adding either $CaCl_2$ as a positive control to each well to give a final concentration of 0.5 mM, or "AA2G", a product name of a particulate composition containing anhydrous crystalline ascorbic acid 2-glucoside, commercialized by Hayashibara Co., Ltd., Okayama, Japan, to give a final concentration of 0.5 or 1 mM. After completion of the culture, the resulting cells were detached from the wall of each well by means of pipetting with PBS containing 1% w/v SDS. A sample of 20 μg protein for each lane per each cell extract in respective wells was applied to sodium dodecyl sulfate polyacrylamide gel electrophoresis (SDS-PAGE) with 10% w/v SDS containing DTT, followed by assaying the concentration of occludin or ZO-1 in each cell extract with "Luminate Western HRP Substrates", a product name of a premixed, ready-to-use chemiluminescent detection reagent using an internal standard "α-Tubulin", commercialized by Merck KGaA, Darmstadt, Germany, wherein there were used "F-11", a product name of an anti-occludin mouse monoclonal antibody, commercialized by Santa Cruz Biotechnology, Inc., Texas, USA, or "ZO1-1A12", a product name of a ZO-1 mouse monoclonal antibody, commercialized by Invitrogen Corporation, Calif., USA, was used as a first antibody; and "PO447", a product name of a horseradish peroxidase (HRPO) labeled anti-mouse IgG, commercialized by DAKO Japan Inc., Tokyo, Japan, or "PO448", a product name of an HRPO-labeled anti-rabbit IgG, commercialized by DAKO Japan Inc., Tokyo, Japan, as a secondary antibody. The results are in Table 9, wherein the numerals affixed with "%" mean relative values when the concentrations of occludin and ZO-1 in the cell extract with $CaCl_2$ as the positive control are respectively regarded as 100%.

TABLE 9

| | Ascorbic acid 2-glucoside concentration for treatment (mM) | | | $CaCl_2$ Concentration for treatment (mM) |
|---|---|---|---|---|
| | 0 | 0.5 | 1 | 1 |
| Occludin concentration in cell extract | 63% | 78% | 85% | 100% |
| ZO-1 Concentration in cell extract | 38% | 72% | 92% | 100% |

As shown in Table 9, ascorbic acid 2-glucoside was revealed to have a production inducibility of occludin and ZO-1 in epidermal keratinocytes, similarly as in the positive control $CaCl_2$, and also revealed to increase the production level of occludin and ZO-1 in a concentration-dependent manner.

The experiment results lead to an estimation that ascorbic acid 2-glucoside effectively induces the production of occludin and ZO-1, as TJ-related proteins in granular layer of epidermis, which play an important role in the barrier function in the skin; and maintains and enhances the barrier function in the skin that declines with ageing.

Experiment 8: Effect of Ascorbic Acid 2-Glucoside on Hyaluronic Acid Production

In this experiment, the effect of ascorbic acid 2-glucoside on the production of hyaluronic acid in the skin was researched with due consideration to the fact that the reduction of hyaluronic acid in epidermis with ageing may induce wrinkles or lower the elasticity of the skin to induce saggings or rough skins.

In accordance with "Evaluation Method for Enhancing Hyaluronic acid Synthesis" disclosed in "Evaluation and Experimental Manual for Humectancy, Skin whitening, Anti-wrinkle, and Anti-oxidation", edited by Hitoshi Masaki, published by Fragrance Journal, pp. 94 to 97, 2012, NHEK cells as a model for typical normal human epidermal cells were suspended in EpiLife medium (pH 7.4), commercialized by Invitrogen Corporation, Calif., USA, inoculated to 12-well microplates at a cell density of $5 \times 10^4$ cells/well, and incubated overnight under conditions of 37° C. and 5% v/v $CO_2$. Thereafter, the cell culture medium was replaced with a fresh HuMedia-KG2 medium commercialized by Kurabo Industries Ltd., Osaka, Japan; and "AA2G", a particulate composition containing anhydrous crystalline ascorbic acid 2-glucoside, commercialized by Hayashibara Co., Ltd., Okayama, Japan, was added to each well to give a final concentration of 0.25, 0.5, or 1 mM, followed by culturing the cells for three days under the conditions of 37° C. and 5% v/v $CO_2$. After completion of the culture, the supernatant in each well was immediately collected and quantified for hyaluronic acid by "Hyaluronan, DuoSet Kit", product code: DY3614, a product name of a commercialized enzyme-linked immunosorbent assay (ELISA) purchased from R & D Systems, Minneapolis, USA. As a control, there was provided a culture system, where cells are cultured similarly as above except for not adding ascorbic acid 2-glucoside. The results are in Table 10.

TABLE 10

|  | Hyaluronic acid concentration in culture supernatant (ng/mL) |
|---|---|
| With no addition (Control) | 1003 ± 111.6 |
| Ascorbic acid 2-glucoside (0.25 mM) | 1222 ± 93.6* |
| Ascorbic acid 2-glucoside (0.5 mM) | 1268 ± 125.2* |
| Ascorbic acid 2-glucoside (1 mM) | 1436 ± 216* |

*$p < 0.05$

As shown in Table 10, ascorbic acid 2-glucoside was revealed to induce the production of hyaluronic acid in epidermal keratinocytes in a concentration-dependent manner.

The experiment results lead to an estimation that ascorbic acid 2-glucoside effectively induces the production of hyaluronic acid relating to skin humectancy, whereby it maintains or enhances the production of hyaluronic acid in the skin that may decline with ageing, and prevents or improves skin dryness, as well as inhibiting the generation, improving the condition, or diminishing the appearance of fine wrinkles.

Experiment 9: Anti-Wrinkle Test (1) with Ascorbic Acid 2-Glucoside

Ascorbic acid 2-glucoside was subjected to an experiment with volunteers for examining the action of improving skin wrinkles by using a cream incorporated therewith. Sixteen female, 37- to 55-year-old, suffering from face wrinkles, were chosen as volunteers and allowed to apply a test cream with the following composition formulation containing 2% by mass of "AA2G", a product name of a particulate composition containing anhydrous crystalline ascorbic acid 2-glucoside, commercialized by Hayashibara Co., Ltd., Okayama, Japan, at around the right and left eyes at a dose of one gram per each application, twice a day after face-washing in the morning and after taking bath in the evening for 90 days. During the test period of time, the volunteers were so instructed as to maintain their skin conditions being applied with creams as much as possible. During the test period of time, the volunteers were so instructed as to spend according to their usual daily life, except for not using any cosmetic or the like that proclaims an effect of improving wrinkles. On days at initiating the test (day 0), the middle of the test period (day 45), and after the termination of the test (day 90), the depths of wrinkles were determined based on the shapes of the volunteers' skin surfaces by the following method and the averaged data are in Table 11.

<Three-Dimensional Measurement for Skin Surface Wrinkles>

On the days at initiating the test (day 0), the middle of the test period (day 45), and after the termination of the test (day 90), both tails of the eyes of each volunteer, as test parts, were subjected to a reflective replica collection kit of ABS-01-W, commercialized by Asahi Biomed, Yokohama, Japan, to prepare skin replicas. The surface shapes of the replicas were analyzed on a reflective replica analyzing system of ASA-03R, commercialized by Asahi Biomed, Yokohama, Japan, to identify wrinkles and determine an average depth from the standard surface for each test part.

<Test Cream>
(Formulation)

| Ingredients | (Weight %) |
|---|---|
| (1) Dimethicone | 0.3 |
| (2) Squalane | 2.0 |
| (3) Cetearyl isononanoate | 1.0 |
| (4) Triethylhexanoin | 2.0 |
| (5) Octyldodecanol | 2.0 |
| (6) C10-30 Cholesterol/lanosterol esters | 3.0 |
| (7) Polyglyceryl-10 myristate | 3.5 |
| (8) Cetyl alcohol | 3.5 |
| (9) Batyl alcohol | 1.0 |
| (10) Cetyl palmitate | 2.05 |
| (11) Glyceryl stearate SE | 2.5 |
| (12) Batyl stearate | 2.5 |
| (13) 1,3-Butylene glycol | 3.0 |
| (14) Methylparaben | 0.2 |
| (15) Glycerin | 4.5 |
| (16) "TORNARE", a product name of a syrup containing saccharide derivatives of trehalose, commercialized by Hayashibara Co., Ltd., Okayama, Japan | 2.0 |
| (17) "AA2G", a product name of a particulate composition containing anhydrous crystalline ascorbic acid 2-glucoside, commercialized by Hayashibara Co., Ltd., Okayama, Japan | 2.0 |
| (18) Citric acid | q.s. |
| (19) Sodium citrate | q.s. |
| (20) Potassium hydroxide | q.s. |
| (21) Refined water | q.s. |

TABLE 11

| Application period of cream (day) | Wrinkle width (μm) | Reduction percentage (%) |
|---|---|---|
| 0 | 204 | 0 |
| 45 | 160 | 20.7 |
| 90 | 126 | 34.8 |

As shown in Table 11, the application of the cream incorporated with ascorbic acid 2-glucoside shallowed the wrinkle width depending on the application period directly. The results indicate that ascorbic acid 2-glucoside has an effect of improving wrinkles in the skin.

Experiment 10: Anti-Wrinkle Test (2) with Ascorbic Acid 2-Glucoside

Since the average depths of wrinkles in both tails of the eyes of the volunteers around forties tended to be shallower compared to those with other ages in Experiment 9, though not specified therein, the action of a cream incorporated with ascorbic acid 2-glucoside was examined in detail by using 10 female volunteers, 40±2 years old, as subjects. Similarly as in Experiment 9 except for setting a test period of time to 42 days, the improvement effect on both tails of the eyes of the volunteers was tested (simply called "additional experiment", hereinafter), revealing that six out of ten subjects gave distinct improved effects on fine wrinkles of both tails of the eyes and the gloss and the moisture conditions were satisfactory. In this additional experiment, the skin turnovers of both tails of the volunteers' eyes were examined just before and after initiating the test in such a manner of pressing adhesive tapes against both tails of the eyes of the 10 volunteers, respectively, to collect the keratinous layer cells of the skin surface, dying the collected cells, determining the cells' area, and comparing the area with the one for each subject determined before conducting the test, in accordance with the assay for turnover of keratinous layer based on the area of keratinous layer cells (the glass slide method) (see "*Fragrance Journal*", Vol. 36, No. 5, pp. 28-30, 2008). The above-identified assay is a relatively easy method for estimating the turnover rate of the skin by measuring the area of keratinous layer cells, i.e., the size of the cells. Regarding the relationship between the area of keratinous layer cells and the turnover of keratinous layer, the assay follows the theory of: The faster the turnover of keratinous layer the lesser the area of keratinous layer, where the turnover corresponds to the proliferation rate of basal cells capable of forming keratinocytes and the turnover rates of both keratinous layer and the skin are in direct proportion to each other.

The results of the above assay for the turnover of keratinous layer revealed that the areas of keratinous layer cells in both tails of the eyes of the six subjects decreased by about five percent in average and the turnover rate in both tails of the eyes (the proliferation rate of basal cells) increased by about 1.2 folds in average, compared to those just before the test. Considering the facts that the test period of 42 days specified in the additional experiment corresponds to just under the period of one skin turnover cycle and the delaying of the skin turnover is said to cause fine wrinkles, the experimental results indicate that the cream rapidly improves the delaying of the skin turnover and effectively improves fine wrinkles. The ages of 40±2 years old are of those who require about two times longer days for their skin turnovers than those at 20 s and become to have apparent fine wrinkles, and therefore the cream is distinctly useful as an agent for improving fine wrinkles directed to so-called pre-aging generation including the above-identified ages, particularly, women in midlife.

Experiment 11: Crystalline Sodium Salt of Ascorbic Acid 2-Glucoside

Experiment 11-1: Preparation of Crystalline Sodium Salt of Ascorbic Acid 2-Glucoside One hundred grams of "AA2G", a product name of a particulate composition containing anhydrous crystalline ascorbic acid 2-glucoside, commercialized by Hayashibara Co., Ltd., Okayama, Japan, was dissolved in 100 mL of 6N sodium hydroxide solution, admixed with an additional 100 mL of methanol, and allowed to stand for about three weeks at 4° C., resulting in a formation of white turbidity and crystals upon microscopic observation. The formed suspension with crystals was filtered with a glass filter to collect the precipitated crystals, which were then washed with a 70% v/v aqueous methanol containing 0.1N hydrochloric acid and dried at 40° C. to obtain an about 35 g crystalline powder.

Experiment 11-2: Study on the Formation Condition of Sodium Salt of Ascorbic Acid 2-Glucoside Ten grams of "AA2G", a product name of a particulate composition containing anhydrous crystalline ascorbic acid 2-glucoside, commercialized by Hayashibara Co., Ltd., Okayama, Japan, was dissolved by the addition of 10 mL of any of the 1 to 10 N aqueous sodium hydroxide solutions shown in the following Table 12, added with 10 mL of methanol, mixed, added with 30 mg of the crystalline sodium salt of ascorbic acid 2-glucoside obtained in Experiment 11-1 as a seed crystal, and allowed to stand at 4° C. for 24 hours, followed by macroscopically observing the degree of crystal precipitation. The degree of crystal precipitation was judged based on the following four grades:

"−": No crystal precipitation;
"+": Slight crystal-precipitation;
"++": Crystal precipitation in an amount roughly equal to half of the total volume; and
"+++": Crystal precipitation and solidification throughout the whole content.

The results are in Table 12.

TABLE 12

| Particulate composition containing anhydrous crystalline ascorbic acid 2-glucoside (g, d.s.b.) | Concentration of NaOH* | | (NaOH)/ (Ascorbic acid 2-glucoside) (molar ratio) | Crystal formation |
|---|---|---|---|---|
| | Concentration (N) | Liquid volume (mL) | | |
| 10 | 10 | 10 | 3.3 | +++ |
| 10 | 8 | 10 | 2.7 | +++ |
| 10 | 6 | 10 | 2.0 | ++ |
| 10 | 5 | 10 | 1.7 | + |
| 10 | 4 | 10 | 1.3 | − |
| 10 | 2 | 10 | 0.7 | − |
| 10 | 1 | 10 | 0.3 | − |
| 10 | 0 | 10 | 0.0 | − |

*Sodium hydroxide

As shown in Table 12, crystal precipitations were observed from respective samples, which had been prepared by dissolving a particulate composition containing anhydrous crystalline ascorbic acid 2-glucoside in any of 5N, 6N, 8N, and 10N aqueous sodium hydroxide solutions and admixing each of the resulting solutions with methanol, wherein the amounts of precipitated crystals more increased as the increase of the sodium hydroxide concentrations. While, no crystal precipitation was observed when the sodium hydroxide concentrations were below 4N. When the sodium hydroxide concentration was 5N, the molar ratio of sodium hydroxide against ascorbic acid 2-glucoside was 1.7, revealing that the formation of crystalline sodium salt of ascorbic acid 2-glucoside requires sodium hydroxide in an amount of at least 1.7 by the molar ratio.

Experiment 11-3: Crystalline Sodium Salt of Ascorbic Acid 2-Glucoside

An about 10 g of the crystalline powder, obtained in Experiment 11-1, was dried in vacuo at 50° C. for 24 hours to obtain an about 8.4 g of crystalline powder with a different appearance from the one obtained in Experiment 11-1. The crystal thus obtained was considered as a novel crystal different from the one obtained in Experiment 11-1.

Experiment 12: Analyses on Crystalline Sodium
Salt of Ascorbic Acid 2-Glucoside

The crystals obtained in Experiments 11-1 and 11-3 were respectively observed their crystalline forms, subjected to HLPC analysis, and measured for sodium content, Fourier-Transform Infrared Spectroscopy (FT-IR), and powder X-ray diffraction figure.

Experiment 12-1: Crystalline Form

Figure 2:
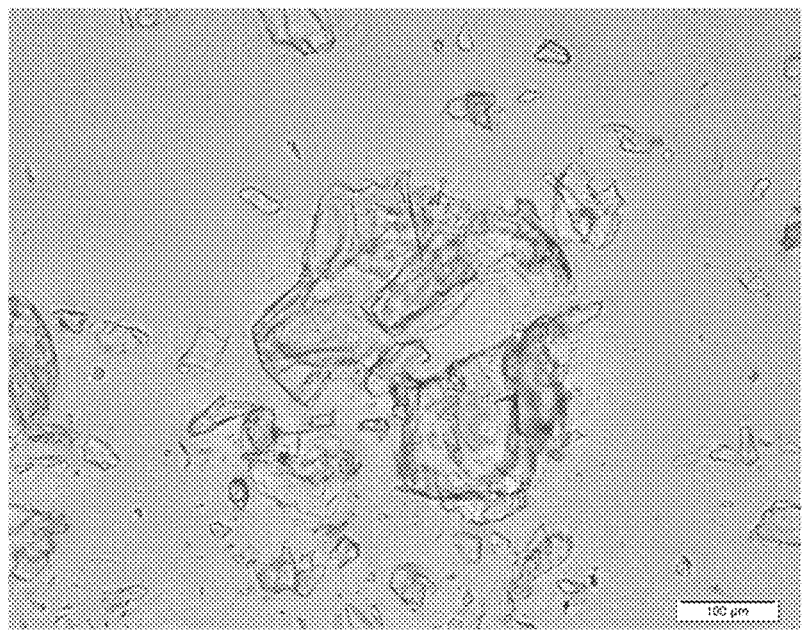
FIG. 2 A microscopic photograph of a crystalline sodium salt of ascorbic acid 2-glucoside (anhydrous crystal).

The crystals obtained in Experiments 11-1 and 11-3 were respectively placed on glass slides, observed for crystalline form by using a phase-contrast microscope, and photographed. Photographs of the crystals are respectively in FIGS. 1 and 2. As found in FIG. 1, the crystal obtained in Experiment 11-1 had a thin plate- or columnar-crystal form. On the contrary, as found in FIG. 2, the crystalline form of that obtained in Experiment 11-3 was a plate crystal, although numerous deformed crystals were observed.

Experiment 12-2: HPLC Analysis

The crystals obtained in Experiments 11-1 and 11-3 were respectively dissolved in an appropriate amount of refined water and subjected to the following HPLC analysis. As a control, "Ascorbic Acid 2-Glucoside 999", with a purity of at least 99.9%, a product name of a particulate composition containing anhydrous crystalline ascorbic acid 2-glucoside", a reagent grade particulate composition containing anhydrous crystalline ascorbic acid 2-glucoside, commercialized by Hayashibara Co., Ltd., Okayama, Japan, was analyzed under the same conditions as above.
<Conditions for HPLC Analysis>
Column: "Wakopak Wakobeads T-330 H$^+$-form", 10 mm in inner diameter×300 mm in length, commercialized by Wako Pure Chemical Industries, Ltd., Tokyo, Japan
Eluent: 0.0001N nitric acid aqueous solution
Flow rate: 0.5 mL/min
Temperature: Ambient temperature
Detection: Refractive index detector The crystals obtained in Experiments 11-1 and 11-3 were dissolved in refined water and subjected to HPLC analysis, revealing that, similarly as in the case of anhydrous crystalline ascorbic acid 2-glucoside as a control, only a peak for ascorbic acid 2-glucoside was detected in every chromatogram, revealing that the crystals obtained in Experiments 11-1 and 11-3 were those which contain ascorbic acid 2-glucoside as a constituent ingredient based on the fact that all the crystals had an ascorbic acid 2-glucoside purity of about 100%.

Experiment 12-3: Measurement of Moisture Content

The moisture content of the crystalline powder obtained in Experiments 11-1 and 11-3 were measured on a conventional vacuum drying method (at 50° C. for 24 hours), revealing that they had 14.9% and 0.2% by mass of moisture, respectively. These results indicated that the crystal obtained in Experiment 11-1 was a hydrous crystal containing ascorbic acid 2-glucoside, while the one obtained in Experiment 11-3 was an anhydrous crystal containing ascorbic acid 2-glucoside.

Experiment 12-4: Measurement of Sodium Content

Twenty-five milligrams of the anhydrous crystal obtained in Experiment 11-3 was weighed, dissolved in 50 mL of refined water, and further diluted five-folds with refined water for use as a sample for measurement. Sodium content in the sample was measured under the following conditions with an inductively coupled plasma-atomic emission spectrometry (ICP-AES) CIROS-120, commercialized by Rigaku Corporation, Tokyo, Japan.
<ICP-AES Conditions of Measurement>
Plasma power: 1400 W
Plasma gas: 13.0 L/min
Auxiliary gas and nebulizer gas: 1.0 L/min
Blank: A 1,000-fold diluted solution of 60% by volume of nitric acid
Solution of standard curve for sodium: A solution prepared by diluting ICP multi-element standard IV, commercialized by Merck KGaA, Darmstadt, Germany, to give a concentration of 0.1 to 10 ppm The anhydrous crystal obtained in Experiment 11-3 had a sodium content of 8.7% by mass, d.s.b. Since the sodium content approximated to the theoretical sodium content of 8.8% by mass, the obtained crystalline sodium salt of ascorbic acid 2-glucoside was estimated to contain three moles of sodium per two moles of ascorbic acid 2-glucoside, based on the assumption that the anhydrous crystal contains one mole of ascorbic acid 2-glucoside, one mole of sodium, and ½ mole of sodium hydroxide, i.e., it has a molar ratio of 1:1.5 [=(ascorbic acid 2-glucoside):(sodium)].

As described above, the hydrous crystalline sodium salt of ascorbic acid 2-glucoside has a moisture content of about 15% by mass, contains four moles of crystal water per one mole of ascorbic acid 2-glucoside, and has a molar ratio of 1:4 [=(ascorbic acid 2-glucoside):(water)], based on the assumption that it contains ascorbic acid 2-glucoside and sodium hydroxide in the above-mentioned molar ratio.

The results in Experiments 12-1 to 12-4 confirmed that the crystal obtained in Experiment 11-1 is a hydrous crystalline sodium salt of ascorbic acid 2-glucoside, and the crystal obtained in Experiment 11-3 is an anhydrous crystalline sodium salt of ascorbic acid 2-glucoside.

Experiment 12-5: FT-IR Spectrum

Figure 3:
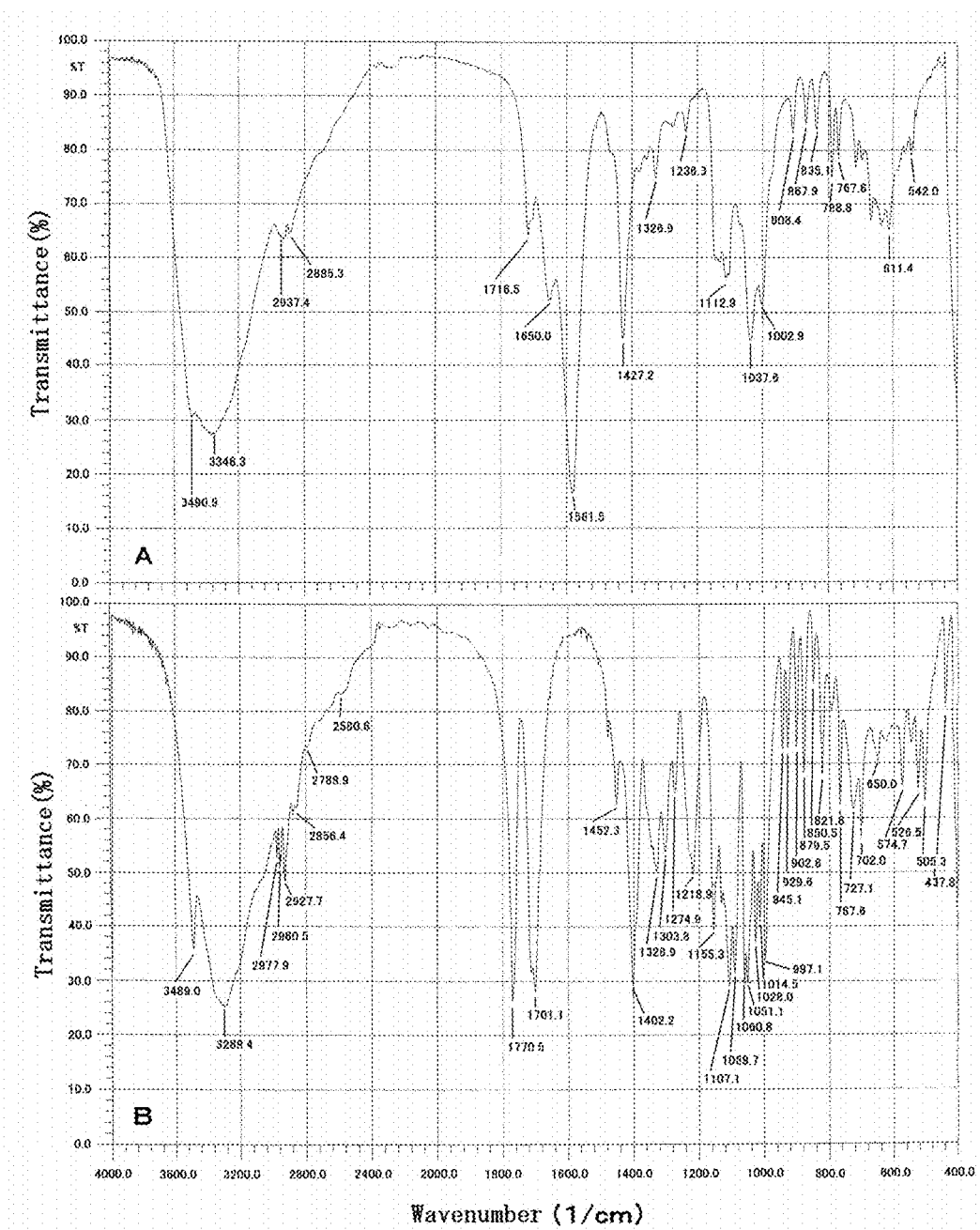
FIG. 3 A figure that compares an FT-IR spectrum for an anhydrous crystalline sodium salt of ascorbic acid 2-glucoside (A) with the one for an anhydrous crystalline ascorbic acid 2-glucoside as a control (B).

Two milligrams of an anhydrous crystalline particulate composition obtained in Experiment 11-3 was added with 200 mg of potassium bromide for use in infrared absorption spectrum analysis, and the mixture was pulverized and mixed with an agate mortar and formed into tablets for use in analysis, where Fourier Transform Infrared Spectrophotometer FTIR-8300, commercialized by Shimadzu Corp., Kyoto, Japan, was used as an apparatus. As a control, "Ascorbic Acid 2-Glucoside 999" with a purity of at least 99.9%, a product name of a reagent grade particulate composition containing anhydrous crystalline ascorbic acid 2-glucoside, commercialized by Hayashibara Co., Ltd., Okayama, Japan, was used and measured similarly as above. The results are in FIG. 3.

As found in FIG. 3A, a relatively large absorption was observed at around 1,580 cm$^{-1}$ in the FT-IR spectrum of the anhydrous crystalline particulate composition containing sodium salt of ascorbic acid 2-glucoside. While, as found in FIG. 3B, the anhydrous crystalline particulate composition containing ascorbic acid 2-glucoside as a control did not show any absorption at the above spectrum region but relatively large absorptions at around 1,700 cm$^{-1}$ and 1,770 cm$^{-1}$ were observed. The large absorption at around 1,580 cm$^{-1}$ for the anhydrous crystalline sodium salt was estimated to be the one derived from stretching vibration of carbonyl group effected by sodium contained in the crystal.

It was estimated that the difference between the above two FT-IR spectra was due to the fact that ascorbic acid 2-glucoside exists in a salt form in the anhydrous crystalline particulate composition containing ascorbic acid 2-glucoside, while ascorbic acid 2-glucoside exists in a free acid form in the anhydrous crystalline particulate composition containing ascorbic acid 2-glucoside as a control.

Experiment 12-6: Powder X-Ray Diffraction Figure

Figure 4:
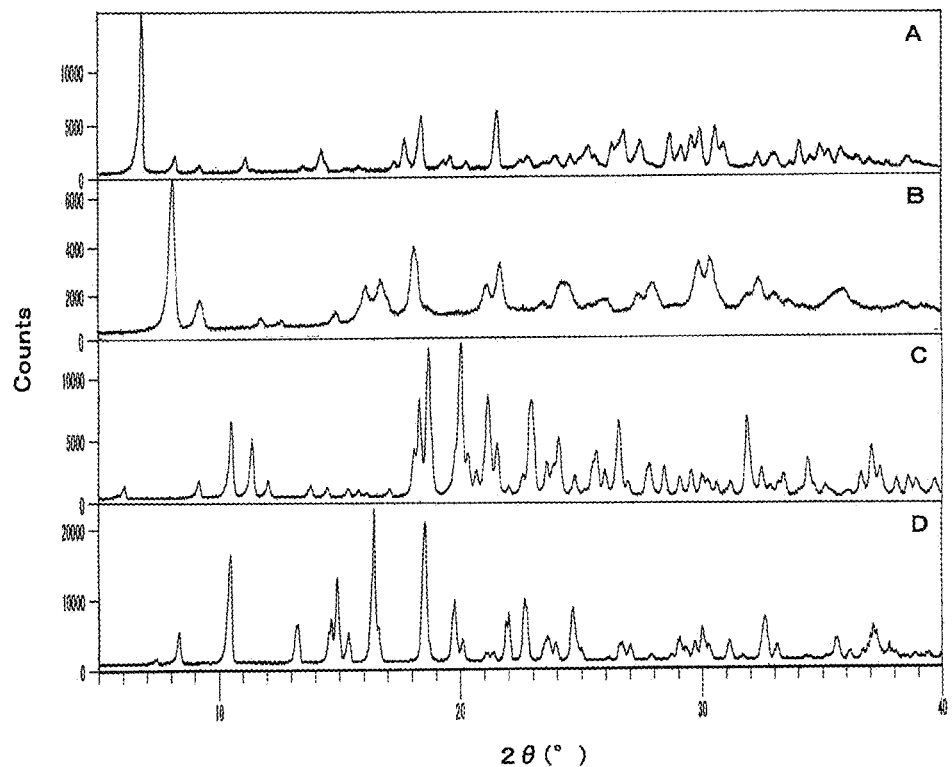
FIG. 4 A figure that compares, with each other, powder X-ray diffraction figures for a hydrous crystalline sodium salt of ascorbic acid 2-glucoside (A), anhydrous crystalline sodium salt of ascorbic acid 2-glucoside (B), hydrous crystalline ascorbic acid 2-glucoside as Control 1 (C), and anhydrous crystalline ascorbic acid 2-glucoside as Control 2 (D).

Using "X' Pert Pro MPD", a product name of a powder X-ray diffractometer commercialized by Spectris Co., Ltd., Tokyo, Japan, about 50 mg of any of the hydrous crystalline sodium salt of ascorbic acid 2-glucoside obtained in Experiment 11-1 and the anhydrous crystalline ascorbic acid 2-glucoside obtained in Experiment 11-3 as samples was placed on a silicon reflection free plate, irradiated with a Cu-Kα ray under the following conditions while rotating, and determined for powder X-ray diffraction figure by a reflection method. The obtained powder X-ray diffraction figures are shown in FIGS. 4A and 4B. As a control, powder X-ray diffraction figures are shown in FIGS. 4C and 4D obtained by similarly measuring both a particulate composition containing hydrous crystalline ascorbic acid 2-glucoside with a purity of 99.5%, commercialized by Hayashibara Co., Ltd., Okayama, Japan, disclosed in International Patent Publication No. WO2012/033218; and "Ascorbic Acid 2-Glucoside 999", with a purity of at least 99.9%, a product name of a reagent grade particulate composition containing anhydrous crystalline ascorbic acid 2-glucoside, commercialized by Hayashibara Co., Ltd., Okayama, Japan.

<Conditions for Irradiating Cu-Kα Ray>
X-Ray tube current: 40 mA
X-Ray tube voltage: 45 kV
Wavelength: 1.5405 Å

As found in FIG. 4A, the hydrous crystalline sodium salt of ascorbic acid 2-glucoside exhibited characteristic diffraction peaks at diffraction angles (2θ) of 6.8°, 8.2°, 14.3°, 17.8°, and 18.4°; while, as found in FIG. 4B, the anhydrous crystalline sodium salt of ascorbic acid 2-glucoside exhibited characteristic diffraction peaks at diffraction angles (2θ) of 8.0°, 9.0°, 16.4°, 17.9°, and 20.8°. These hydrous and anhydrous crystalline sodium salts of ascorbic acid 2-glucoside showed powder diffraction figures different from each other and also completely different from those of conventionally known particulate compositions containing hydrous or anhydrous crystalline ascorbic acid 2-glucoside.

These data revealed that both of the hydrous and anhydrous crystalline sodium salts of ascorbic acid 2-glucoside of the present invention are novel crystals.

For reference, the anhydrous crystalline sodium salt of ascorbic acid 2-glucoside absorbed moisture to give a constant moisture level of about 15% by mass, when allowed to stand at 25° C. under a relative humidity of 75.2% or higher, and exhibited the same powder X-ray diffraction figure as that of hydrous crystalline sodium salt of ascorbic acid 2-glucoside, concluding that the hydrous crystal mutually converts into an anhydrous crystal by being dried and also the anhydrous crystal converts into a hydrous crystal by absorbing moisture in a phase transition manner.

Experiment 12-7: Single Crystal X-Ray Crystallography

Two grams of "Ascorbic Acid 2-Glucoside 999", with a purity of at least 99.9%, a product name of a particulate composition containing anhydrous crystalline ascorbic acid 2-glucoside, commercialized by Hayashibara Co., Ltd., Okayama, Japan, was dissolved in 10 mL of 3N sodium hydroxide solution, added with 30 mL of methanol, mixed, and allowed to stand at 4° C. for three weeks to precipitate single crystals of hydrous crystalline sodium salt of ascorbic acid 2-glucoside. From among the obtained single crystals, an appropriate sized crystal was selected, coated with PARATONE oil, set up in an X-ray diffractometer, and measured for X-ray diffraction patterns by oscillation photography under the following conditions. "R-AXIS RAPID-R", commercialized by Rigaku Corporation, Tokyo, Japan, was used as a measuring apparatus, and "Crystal Structure Ver. 3.8.2", commercialized by Rigaku Corporation, Tokyo, Japan, was used as an analysis software.

<Conditions for Measurement>
X-Ray source: Cu
Power: 50 kV-100 mA
Incident X-ray: Cu-Kα ray
Incident X-ray size: About 0.5 mm φ
Crystal dimensions: 0.3×0.2×0.2 mm
Detector: Imaging plate
Measurement temperature: About −170° C. (nitrogen gas blowing method)

Figure 5:
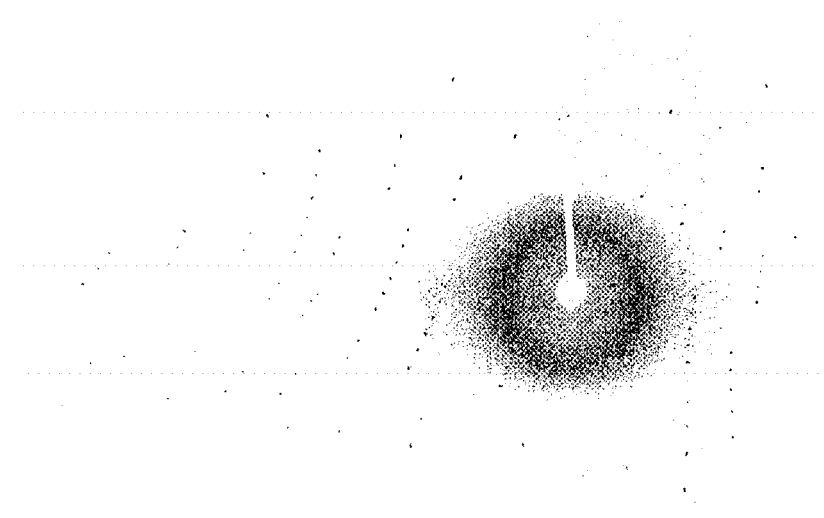
FIG. 5 A single-crystal X-ray diffraction pattern for a hydrous crystalline sodium salt of ascorbic acid 2-glucoside.

An X-ray diffraction pattern of the single crystal was shown in FIG. 5. In the X-ray diffraction pattern, a plenty of diffraction mottles (spots) were observed, revealing that the crystal was a single crystal. Table 13 is a summary of crystallographical parameters of hydrous crystalline sodium salt of ascorbic acid 2-glucoside, obtained by the single crystal X-ray crystallography.

TABLE 13

| Crystalline system | Lattice constant | Space group |
|---|---|---|
| Orthorhombic system | a = 6.9733(4) Å<br>b = 14.4839(8) Å<br>c = 19.3221(11) Å<br>V = 1951.54(19) Å$^3$ | Pbca(#61) |

From the obtained data on X-ray diffraction strength, as shown in Table 13, it was determined that the hydrous crystalline sodium salt of ascorbic acid 2-glucoside belongs to orthorhombic system, and the space group is Pbca (#61); the lattice constant, a=6.9733 Å, b=14.4839 Å, c=19.3221 Å, and V=1951.54 Å$^3$.

Experiment 13: pH of a Composition of Crystalline Sodium Salt of Ascorbic Acid 2-Glucoside and Anhydrous Crystalline Ascorbic Acid 2-Glucoside An anhydrous crystalline sodium salt of ascorbic acid 2-glucoside, obtained by the method in the above Experiment 11-3, and "Ascorbic Acid 2-Glucoside 999", with a purity of at least 99.9%, a product name of a particulate composition containing anhydrous crystalline ascorbic acid 2-glucoside, commercialized by Hayashibara Co., Ltd., Okayama, Japan, were made into compositions with the ratios by mass ranging from 100:0 to 0:100 as shown in Table 14, and dissolved in 10-fold volume of refined water against the mass of each composition, followed by measuring the pHs of the resulting solutions. The results are in Table 14.

TABLE 14

| | | | | | | | | | | | |
|---|---|---|---|---|---|---|---|---|---|---|---|
| Anhydrous crystalline sodium salt of ascorbic acid 2-glucoside (g, d.s.b.) | 2 | 1.6 | 1.2 | 1.1 | 1.05 | 1.04 | 1.02 | 1 | 0.8 | 0.4 | 0 |
| Particulate composition containing anhydrous crystalline ascorbic acid 2-glucoside (g, d.s.b.) | 0 | 0.4 | 0.8 | 0.9 | 0.95 | 0.96 | 0.98 | 1 | 1.2 | 1.6 | 2 |
| Refined water (mL) | 20 | 20 | 20 | 20 | 20 | 20 | 20 | 20 | 20 | 20 | 20 |
| Composition ratio (ratio by mass) [(anhydrous crystalline sodium salt):(anhydrous crystal)] | 100:0 | 80:20 | 60:40 | 55:45 | 53:47 | 52:48 | 51:49 | 50:50 | 40:60 | 20:80 | 0:100 |
| pH | 13.1 | 12.9 | 12.3 | 11.6 | 10.5 | 5.4 | 4.6 | 4.5 | 3.4 | 2.6 | 1.7 |

As found in Table 14, the aqueous solution prepared by dissolving the anhydrous crystalline sodium salt of ascorbic acid 2-glucoside alone in water had a pH of 13.1, while the aqueous solution prepared by dissolving the powder containing anhydrous crystalline ascorbic acid 2-glucoside alone in water had a pH of 1.7. The aqueous solutions of the compositions of the anhydrous crystalline sodium salt of ascorbic acid 2-glucoside and the particulate composition containing anhydrous crystalline ascorbic acid 2-glucoside exhibited pHs in the range of 12.9 to 2.6 depending on their composition ratios. It was revealed that the aqueous solutions of ascorbic acid 2-glucoside can be made to give desired pHs ranging widely from acidic pHs and alkaline pHs by combining sodium salt of ascorbic acid 2-glucoside and ascorbic acid 2-glucoside in appropriate ratios, particularly, when combined in ratios ranging from 55:45 to 40:60, they exhibit pHs ranging from weak alkaline to weak acidic pHs preferable in preparing cosmetics.

Experiment 14: Effect of Sodium Salt of Ascorbic Acid 2-Glucoside on Gelatinizing Agents To examine the effect of sodium salt of ascorbic acid 2-glucoside in preparing gelatinous cosmetics, a model experiment for preparing gels containing ascorbic acid 2-glucoside was conducted by using the nine types of carbomers, as gelling agents generally used in the field of cosmetics, as listed in Table 15 (five types of "CARBOPOL", commercialized by Nikko Chemicals Co., Ltd., Tokyo, Japan; three types of "HIBIS WAKO", commercialized by Wako Pure Chemical Industries, Ltd., Tokyo, Japan; one type of "AQUPEC", commercialized by Sumitomo Seika Chemicals Company Ltd., Osaka, Japan), an antiseptic, and ascorbic acid 2-glucoside. The properties of gels, which had been prepared by adjusting pHs with citric acid buffers and sodium hydroxide at the step of adding ascorbic acid 2-glucoside, and another gels with pHs of around 6.5 but with no citric acid buffer, which had been prepared with sodium salt of ascorbic acid 2-glucoside without employing any neutralization treatment.

Five grams of any of the above gelling agents and 7.5 g of pentylene glycol as an antiseptic were dissolved in 237.5 g of water into a gel base (with a concentration of 2% by mass). The anhydrous crystalline sodium salt of ascorbic acid 2-glucoside, obtained by the method in Experiment 12-1, was dissolved in water to prepare an aqueous solution containing 20 g of ascorbic acid 2-glucoside per 250 g of the aqueous solution (called "aqueous solution of sodium salt of ascorbic acid 2-glucoside", hereinafter). To 25 g of each of the gel bases was added 25 g of the aqueous solution of sodium salt of ascorbic acid 2-glucoside, and the resulting solutions were respectively admixed with water to give a total amount of 100 g each and to obtain gels with pHs of around 6.5. Twenty grams of "AA2G", a product name of a particulate composition containing anhydrous crystalline ascorbic acid 2-glucoside, commercialized by Hayashibara Co., Ltd., Okayama, Japan, was dissolved in 100 g of water and prepared into a solution with a total mass of 164.7 g, called "neutralized aqueous solution of ascorbic acid 2-glucoside", hereinafter, by neutralizing the ascorbic acid 2-glucoside with the addition of 20 g of citric acid buffer, containing 1% by mass of citric acid and 15% by mass of sodium citrate, and 24.7 g of 10% sodium hydroxide solution. To 25 g of any of the gel bases was added 16.47 g of the neutralized aqueous solution of ascorbic acid 2-glucoside, added with two grams of 10% by mass of sodium hydroxide solution, and supplemented with water to give a total amount of 100 g and to obtain gels with pHs of around 6.5. Table 15 shows the pHs and the observations on the properties of the gels (carbomer concentration: 0.5%, ascorbic acid 2-glucoside concentration: 2%).

TABLE 15

| | Sodium salt of ascorbic acid 2-glucoside | | Neutralized ascorbic acid 2-glucoside | |
|---|---|---|---|---|
| Carbomer | Gel property | pH | Gel property | pH |
| CARBOPOL 940 | ○ | 6.45 | X | 6.55 |
| CARBOPOL 980 | Δ | 6.45 | X | 6.50 |
| CARBOPOL 981 | ○ | 6.37 | Δ | 6.51 |
| CARBOPOL ULTREZ 10 | Δ | 6.54 | X | 6.61 |
| CARBOPOL ETD 2050 | Δ | 6.26 | X | 6.43 |
| HIBIS WAKO 103 | Δ | 6.26 | X | 6.31 |
| HIBIS WAKO 104 | ○ | 6.40 | Δ | 6.18 |
| HIBIS WAKO 105 | ○ | 6.36 | Δ | 6.38 |
| AQUPEC HV-505 | Δ | 6.31 | X | 6.46 |

Note
X: With no viscosity,
Δ: With viscosity,
○: With shape retainability

As evident from Table 15, no gel with shape as a gel was obtained even though some of the gel bases, which had been prepared by using ascorbic acid 2-glucoside and being neutralized with citric acid buffer and sodium hydroxide, exhibited viscosity but all the gel bases had a relatively high free-flowing ability. Every gel base, which had been prepared by using sodium salt of ascorbic acid 2-glucoside, retained viscosity and kept shape as a gel. These results indicate that the use of sodium salt of ascorbic acid 2-glucoside relatively easily facilitates the production of gelatinous cosmetics, which could not have been easily prepared with ascorbic acid 2-glucoside.

Experiment 15: Anti-Wrinkle Action of Cosmetic Lotion

A volunteer test on anti-wrinkle action was carried out using three types of cosmetic lotions, i.e., cosmetic lotion 1 with no ascorbic acid 2-glucoside (control); cosmetic lotion 2 prepared by incorporating "AA2G", a product name of a particulate composition containing anhydrous crystalline ascorbic acid 2-glucoside, commercialized by Hayashibara Co., Ltd., Okayama, Japan, in an amount of two percent by mass, along with sodium hydroxide as a neutralizer and citric acid plus sodium citrate as pH-regulators; and cosmetic lotion 3 prepared by incorporating a particulate composition containing anhydrous crystalline sodium salt of ascorbic acid 2-glucoside obtained by the later described method in Example 2 in an amount of two percent by mass without employing any neutralization treatment.

Cosmetic lotion 1: It was prepared by dissolving the ingredients (1) and (4) to (7) in Table 16 in refined water (14) to obtain a water phase, mixing the water phase with a solution prepared by dissolving polyoxyethylene oleyl alcohol (8) and flavor (10) in ethanol (9), and adjusting the resulting mixture to pH 6.5 with an adequate amount of sodium hydroxide.

Cosmetic lotion 2: It was prepared similarly as in cosmetic lotion 1 except for dissolving the ingredients (1) and (4) to (7) in Table 16 in a part of refined water (14); dissolving in the aqueous solution "AA2G", a product name of a particulate composition containing anhydrous crystalline ascorbic acid 2-glucoside, commercialized by Hayashibara Co., Ltd., Okayama, Japan; neutralizing the resulting mixture with sodium hydroxide; adjusting the mixture to pH 6.5 by the addition of citric acid (11) and sodium citrate (12) as pH-regulators; and adding the remaining refined water to the mixture to obtain a water phase.

Cosmetic lotion 3: It was prepared similarly as in cosmetic lotion 1 except for using a particulate composition containing anhydrous crystalline sodium salt of ascorbic acid 2-glucoside as sodium salt of ascorbic acid 2-glucoside (3), which had been prepared by the later described method in Example 2, and adjusting the lotion to pH 6.5.

TABLE 16

| Ingredient | Cosmetic lotion 1 (Control) | Cosmetic lotion 2 | Cosmetic lotion 3 |
| --- | --- | --- | --- |
| (1) Sorbitol | 4 | 4 | 4 |
| (2) Ascorbic acid 2-glucoside | 0 | 2 | 0 |
| (3) Sodium salt of ascorbic acid 2-glucoside | 0 | 0 | 2 |
| (4) Dipropylene glycol | 6 | 6 | 6 |
| (5) Polyethylene glycol 1500 | 5 | 5 | 5 |
| (6) Methyl cellulose | 0.2 | 0.2 | 0.2 |
| (7) Quince seed | 0.1 | 0.1 | 0.1 |
| (8) Polyoxyethylene oleyl alcohol | 0.5 | 0.5 | 0.5 |
| (9) Ethanol | 5 | 5 | 5 |
| (10) Flavor | q.s. | q.s. | q.s. |
| (11) Citric acid | 0 | 0.01 | 0 |
| (12) Sodium citrate | 0 | 0.15 | 0 |
| (13) Sodium hydroxide | q.s. | q.s. | 0 |
| (14) Refined water | Remaining | Remaining | Remaining |

Cosmetic lotion 1 (Control), cosmetic lotion 2, and cosmetic lotion 3 obtained in the above were respectively examined for anti-wrinkle action and anti-fine-wrinkle action. Thirty female subjects, 37- to 55-year-old, suffering from wrinkles and fine wrinkles, were randomly divided into three groups with ten subjects each, which were respectively allowed to use any one of cosmetic lotions 1 to 3 twice a day (both in the morning and evening) for successive four weeks. During the test period of time, the subjects were so instructed as to spend their usual daily life, except for avoiding the use of cosmetics proclaiming any improvement of wrinkles. After completion of the test period of time, all the subjects were received a questionnaire about the improvement of wrinkles and fine wrinkles, the improvement of skin firmness and elasticity, and the feeling of use. The numbers of subjects, who answered "it exerted an improved effect" on wrinkles and fine wrinkles, as well as skin firmness and elasticity; and "the feeling of use was satisfactory", were tabulated in Table 17.

TABLE 17

| Evaluation item | Cosmetic lotion 1 (Control) | Cosmetic lotion 2 | Cosmetic lotion 3 |
| --- | --- | --- | --- |
| Improvement of wrinkles | 1 | 7 | 7 |
| Improvement of fine wrinkles | 2 | 6 | 6 |
| Improvement of skin firmness and elasticity | 2 | 7 | 8 |
| Satisfactory feeling of use | 3 | 5 | 7 |

As evident from Table 17, the number of subjects with cosmetic lotion 1, who answered "it exerted an improved effect" on wrinkles and fine wrinkles, was two out of ten; at least six out of ten with cosmetic lotion 2 or 3 answered "it exerted an improved effect". As for the feeling of use, three out of ten with cosmetic lotion 1 answered "Satisfactory", while five with cosmetic lotion 2 and seven with cosmetic lotion 3 answered "Satisfactory". During the test period of time, there was no subject with any induced skin problem, revealing that all the cosmetic lotions were harmless. The above results indicate that cosmetic lotions with ascorbic acid 2-glucoside or sodium salt thereof have more advantageous effects of improving wrinkles and fine wrinkles and imparting firmness and elasticity to the skin, compared to cosmetic lotions with no ascorbic acid 2-glucoside.

Experiment 16: Anti-Blemish and Anti-Freckle Action of Milky Lotion

Based on the formulation in Table 18 (numerals are expressed based on % by mass), three types of milky lotions (emollient lotions), i.e., milky lotion 1 with no ascorbic acid 2-glucoside (Control); milky lotion 2 prepared by incorporating "AA2G", a product name of a particulate composition containing anhydrous crystalline ascorbic acid 2-glucoside, commercialized by Hayashibara Co., Ltd., Okayama, Japan, in an amount of three percent by mass, and neutralizing and adjusting the resultant to a prescribed pH with sodium hydroxide; and milky lotion 3 prepared by incorporating a particulate composition containing anhydrous crystalline sodium salt of ascorbic acid 2-glucoside in an amount of three percent by mass without employing any neutralization treatment, which were then subjected to a volunteer test on the action of anti-blemishes and anti-freckles.

Milky lotion 1: The ingredients (7) to (9) and (14) in Table 18 were added to refined water (15), mixed while heating, and adjusted with sodium hydroxide to give a pH of 7.0 to make it into a water phase. The ingredients (1) to (5) in Table 18 were heated to 70° C. to make it into an oil phase separately. The oil phase was added to the water phase, emulsified preliminary, emulsified to homogeneity with a homomixer, cooled, and added with triethanolamine (6), carboxyvinylpolymer (10), and flavor (11) to obtain a milky lotion.

Milky lotion 2: It was similarly prepared as in milky lotion 1 except for finally adding the following solution prepared by using "AA2G", a product name of a particulate composition containing anhydrous crystalline ascorbic acid 2-glucoside, commercialized by Hayashibara Co., Ltd., Okayama, Japan, as ascorbic acid 2-glucoside (12), dissolving the particulate composition in a part of refined water (14), adding sodium hydroxide (14), and neutralizing and adjusting the resulting mixture to pH 7.0.

Milky lotion 3: It was similarly prepared as in milky lotion 1 except for finally adding the following solution prepared by using a particulate composition containing anhydrous crystalline sodium salt of ascorbic acid 2-glucoside prepared by the method in Example 2 as sodium salt of ascorbic acid 2-glucoside (13), dissolving the particulate composition in a part of refined water (14), and adjusting the resulting solution to pH 7.0.

TABLE 18

| Ingredient | Milky lotion 1 (Control) | Milky lotion 2 | Milky lotion 3 |
| --- | --- | --- | --- |
| (1) Stearic acid | 3.5 | 3.5 | 3.5 |
| (2) Cetanol | 0.5 | 0.5 | 0.5 |
| (3) Lanolin | 0.5 | 0.5 | 0.5 |
| (4) Petrolatum | 3 | 3 | 3 |
| (5) Squalane | 2 | 2 | 2 |
| (6) Triethanolamine | q.s. | q.s. | q.s. |
| (7) Propylene glycol | 3 | 3 | 3 |
| (8) Sorbitol (70%) | 2 | 2 | 2 |
| (9) 1,2-Pentane diol | 2 | 2 | 2 |
| (10) 1% Carboxyvinyl polymer (liquid neutralized with alkali) | 8 | 8 | 8 |
| (11) Flavor | q.s. | q.s. | q.s. |
| (12) Ascorbic acid 2-glucoside | 0 | 3 | 0 |
| (13) Sodium salt of ascorbic acid 2-glucoside | 0 | 0 | 3 |
| (14) Sodium hydroxide | q.s. | q.s. | 0 |
| (15) Reined water | Remaining | Remaining | Remaining |

The milky lotions 1 (Control), 2, and 3 obtained in the above were examined for anti-blemishes and anti-freckles. Thirty female subjects, 22- to 51-year-old, suffering from blemishes and freckles, were randomly divided into three groups consisting of 10 subjects each, who were allowed to use any one of milky lotions 1 to 3 for successive four weeks. During the test period of time, the subjects were so instructed as to spend their usual daily life except for avoiding the use of any cosmetic proclaiming an effect of improving blemishes and freckles. After terminating the test period of time, improved effects on skin blemishes and freckles were judged on questionnaires. The test results are in Table 19.

TABLE 19

| | Judgement on the action of improving blemishes and freckles | | |
| --- | --- | --- | --- |
| | Improved | Slightly improved | Not improved |
| Milky lotion 1 (Control) | 1 | 2 | 7 |
| Milky lotion 2 | 3 | 4 | 3 |
| Milky lotion 3 | 4 | 4 | 2 |

As shown in Table 19, one out of ten subjects with milky lotion 1 (Control) answered that blemishes and freckles were "Improved", and two out of ten subjects answered "Slightly improved", while at least seven out of ten subjects with milky lotion 2 or 3 answered "Improved" or "Slightly improved". During the test period of time, there was no subject with any induced skin problem, revealing that these milky lotions are harmless. The above results indicate that milky lotions with ascorbic acid 2-glucoside or sodium salt thereof have a more advantageous effect of improving blemishes and freckles compared to the milky lotions with no ascorbic acid 2-glucoside.

Experiment 17: Anti-Sagging Skin Effect of Face Wash

Based on the formulation (numerals are expressed based on % by mass) shown in Table 20, three types of face washes (cleansing creams), i.e., face wash 1 (Control) with no ascorbic acid 2-glucoside, face wash 2 prepared by incorporating "AA2G", a product name of a particulate composition containing anhydrous crystalline ascorbic acid 2-glucoside, "AA2G", a particulate composition containing anhydrous crystalline ascorbic acid 2-glucoside, commercialized by Hayashibara Co., Ltd., Okayama, Japan, in an amount of two percent by mass and using potassium hydroxide as a neutralizer and pH-regulator, and face wash 3 prepared by incorporating an anhydrous crystalline particulate composition of sodium salt of ascorbic acid 2-glucoside obtained by the later described method in Example 3 in an amount of two percent by mass without using any pH-regulator, all of which were subjected to a volunteer test on anti-sagging skin action.

Face wash 1: A water phase was prepared by dissolving the ingredients (11) to (13) in Table 20 in refined water (14). The water phase was gradually added, while stirring, to an oil phase which had been prepared by mixing the ingredients (1) to (8) in Table 20, melted, and adjusted to 70° C., and the mixture was kept at 70° C. to terminate saponification reaction. The resulting mixture was cooled to 50° C. while stirring, mixed to homogeneity, and cooled to 25° C. to obtain a face wash (cleansing cream) with pH 9.0.

Face wash 2: It was similarly prepared as in face wash 1 except for using, as ascorbic acid 2-glucoside (9), "AA2G", a product name of a particulate composition containing anhydrous crystalline ascorbic acid 2-glucoside, commercialized by Hayashibara Co., Ltd., Okayama, Japan, dissolving it in a part of refined water (14), neutralizing the solution with potassium hydroxide, and mixing the resulting solution with the other ingredients for face wash cooled previously.

Face wash 3: It was similarly prepared as in face wash 1 except for using, as sodium salt of ascorbic acid 2-glucoside (10), a particulate composition containing anhydrous crystalline sodium salt of ascorbic acid 2-glucoside obtained by the later described method in Example 2, dissolving it in apart of refined water (14), and incorporating the resulting solution after cooling to the other ingredients for face wash without neutralizing the solution.

TABLE 20

| Ingredient | Face wash 1 (Control) | Face wash 2 | Face wash 3 |
| --- | --- | --- | --- |
| (1) Stearic acid | 8 | 8 | 8 |
| (2) Palmitic acid | 5 | 5 | 5 |
| (3) Myristic acid | 10 | 10 | 10 |

TABLE 20-continued

| Ingredient | Face wash 1 (Control) | Face wash 2 | Face wash 3 |
|---|---|---|---|
| (4) Sodium lauryl sulfate | 8 | 8 | 8 |
| (5) Lauric acid diethanolamide | 4 | 4 | 4 |
| (6) Lanolin | 2 | 2 | 2 |
| (7) Cetanol | 3 | 3 | 3 |
| (8) Glycerin | 15 | 15 | 15 |
| (9) Ascorbic acid 2-glucoside | 0 | 2 | 0 |
| (10) Sodium salt of ascorbic acid 2-glucoside | 0 | 0 | 2 |
| (11) Potassium hydroxide | q.s. | q.s. | q.s. |
| (12) 1,2-Hexane diol | 1.5 | 1.5 | 1.5 |
| (13) Flavor | q.s. | q.s. | q.s. |
| (14) Refined water | Remaining | Remaining | Remaining |

The above-obtained face washes 1 (Control), 2, and 3 were examined for anti-sagging skin action. Thirty males and females, 36- to 58-year-old, suffering from saggings in the skin were divided into three groups consisting of 10 each to have substantially the same male-to-female ratio. To each subject in every group was allowed to use any one of face washes 1 to 3 for successive four weeks. During the test period of time, the subjects were so instructed as to spend their usual daily life, except for avoiding the use of any cosmetic or the like proclaiming an effect of improving saggings in the skin. After terminating the test period of time, the subjects were asked for improved effect on sagging in the skin. The results are in Table 21.

TABLE 21

| | Judgement on the action of improving saggings in the skin | | |
|---|---|---|---|
| | Improved | Slightly improved | Not improved |
| Face wash 1 (Control) | 2 | 2 | 6 |
| Face wash 2 | 4 | 4 | 2 |
| Face wash 3 | 3 | 5 | 2 |

As shown in Table 21, two out of ten subjects with face wash 1 (Control) answered "Improved" in saggings of their skins and two out of ten subjects answered "Slightly improved", while eight out of ten subjects with face wash 2 or 3 answered "improved" or "Slightly improved". During the test period of time, there was no subject with any skin problem, revealing that the face washes were harmless. The above results indicate that face washes with ascorbic acid 2-glucoside or sodium salt thereof have an advantageous effect of improving saggings in the skin compared to face washes with no ascorbic acid 2-glucoside.

Experiment 18: Skin-Whitening and Anti-Wrinkle Actions of Serums

Based on the formulation (numerals are expressed based on % by mass) in Table 22, three types of serums, i.e., serum 1 (Control) with no ascorbic acid 2-glucoside; serum 2 prepared by incorporating "AA2G", a product name of a particulate composition containing anhydrous crystalline ascorbic acid 2-glucoside, commercialized by Hayashibara Co., Ltd., Okayama, Japan, in an amount of three percent by mass, and adjusting the resultant with sodium hydroxide to pH 6.5; and serum 3 prepared by using a particulate composition containing anhydrous crystalline sodium salt of ascorbic acid 2-glucoside obtained by the later described Example 3 in an amount of three percent by mass without using any pH-regulator; all of which were subjected to a volunteer test on skin-whitening and anti-wrinkle actions.

Serum 1: According to the formulation of Table 22, the ingredients (1) to (5) and (12) to (18) were mixed, further admixed with a mixture which had been prepared by mixing the ingredients (9) to (11), homogenized, and adjusted to give a pH of 6.5 for obtaining a serum.

Serum 2: It was similarly prepared as in serum 1 except for incorporating, as ascorbic acid 2-glucoside (6), "AA2G", a product name of a particulate composition containing anhydrous crystalline ascorbic acid 2-glucoside, commercialized by Hayashibara Co., Ltd., Okayama, Japan, in an amount of three percent by mass; and adjusting the resultant with potassium hydroxide to give a pH of 6.5.

Serum 3: It was similarly prepared as in serum 1 except for incorporating, as sodium salt of ascorbic acid 2-glucoside (7), a particulate composition containing anhydrous crystalline sodium salt of ascorbic acid 2-glucoside, obtained in the later described Example 2; and adjusting the resultant to give a pH of 6.5 without employing a neutralization treatment with potassium hydroxide.

TABLE 22

| Ingredient | Serum 1 (Control) | Serum 2 | Serum 3 |
|---|---|---|---|
| (1) Glycerin | 5 | 5 | 5 |
| (2) Dipropylene glycol | 10 | 10 | 10 |
| (3) Ethanol | 5 | 5 | 5 |
| (4) Carboxyvinylpolymer | 0.2 | 0.2 | 0.2 |
| (5) Sodium hyaluronate | 0.5 | 0.5 | 0.5 |
| (6) Ascorbic acid 2-glucoside | 0 | 3 | 0 |
| (7) Sodium salt of ascorbic acid 2-glucoside | 0 | 0 | 3 |
| (8) Potassium hydroxide | q.s. | q.s. | q.s. |
| (9) Polyoxyethylene (20 moles) sorbitan monooleate | 0.5 | 0.5 | 0.5 |
| (10) Polyoxyethylene (20 moles) octyldodecanol | 1 | 1 | 1 |
| (11) *Olea europaea* [olive] oil | 0.15 | 0.15 | 0.15 |
| (12) Placenta extract | 0.1 | 0.1 | 0.1 |
| (13) Vitamin E acetate | 0.1 | 0.1 | 0.1 |
| (14) Sodium hydrogen sulfite | q.s. | q.s | q.s |
| (15) DETA•3Na | q.s. | q.s | q.s |
| (16) Flavor | q.s. | q.s | q.s |
| (17) 1,3-Butylene glycol | q.s. | q.s | q.s |
| (18) Refined water | Remaining | Remaining | Remaining |

The above-obtained serum 1 (Control), serum 2, and serum 3 were examined for skin-whitening and anti-wrinkle actions. Thirty female subjects, 26- to 48-year-old, suffering from dullness and wrinkles, were randomly divided into three groups consisting of 10 each, which were respectively allowed to use any one of serums 1 to 3 for successive four weeks. During the test period of time, the subjects were so instructed as to spend their usual daily life, except for avoiding the use of any cosmetic or the like proclaiming a skin-whitening effect and an effect of improving wrinkles. After terminating the test period of time, the skin-whitening effect and the wrinkle-improving effect in the subjects were evaluated on questionnaires. The test results are in Table 23.

TABLE 23

| | Judgement on skin-whitening and wrinkle-improving actions | | |
|---|---|---|---|
| | Improved | Slightly improved | Not improved |
| Serum 1 (Control) | 1 | 1 | 8 |

TABLE 23-continued

Judgement on skin-whitening and wrinkle-improving actions

|  | Improved | Slightly improved | Not improved |
|---|---|---|---|
| Serum 2 | 4 | 3 | 3 |
| Serum 3 | 5 | 2 | 3 |

As shown in Table 23, one out of ten subjects with serum 1 (Control) answered "Improved" in skin-whitening and wrinkles, and one out of ten subjects answered "Slightly improved", while at least seven out of ten subjects with serum 2 or 3 answered "Improved" or "Slightly improved". During the test period of time, there was found no subject with any induced skin problem, revealing that the serums have no safety problems. The above results indicate that serums with ascorbic acid 2-glucoside or sodium salt thereof have an advantageous skin-whitening action and wrinkle-improving effect.

The following examples explain the present invention in more detail, however, they should never restrict the present invention.

Example 1

<Cosmetic Material>

Five hundred grams of "AA2G", a product name of a particulate composition containing anhydrous crystalline ascorbic acid 2-glucoside, commercialized by Hayashibara Co., Ltd., Okayama, Japan, was dissolved in 500 mL of 8N aqueous sodium hydroxide solution. The solution was admixed with 750 mL of ethanol and allowed to stand at 4° C. for five days to precipitate crystals. The resulting mixture was filtered with a glass filter to collect the crystals, which were then washed with a small amount of 70% aqueous ethanol solution, dried at 40° C., and pulverized to obtain 326 g of a particulate composition containing hydrous crystalline sodium salt of ascorbic acid 2-glucoside.

The product is a novel particulate composition containing the above hydrous crystal and, similarly as in conventional particulate compositions containing anhydrous crystalline ascorbic acid 2-glucoside, it can be advantageously used as a cosmetic material, as well as a base material for quasi-drugs, pharmaceuticals, foods, etc. Since the product exhibits alkalinity when in an aqueous solution form, it can be advantageously used in preparing products, where unfavorable inconveniences are inevitably induced depending on a method of neutralizing ascorbic acid 2-glucoside with an alkali.

Example 2

<Cosmetic Material>

One hundred parts by mass of a particulate composition containing anhydrous crystalline sodium salt of ascorbic acid 2-glucoside obtained by the method in Example 1 was dried in vacuo at 50° C. for 24 hours, and pulverized to obtain 81 parts by mass of a particulate composition containing anhydrous crystalline ascorbic acid 2-glucoside.

The product is a novel particulate composition containing anhydrous crystalline ascorbic acid 2-glucoside and, similarly as in conventional particulate compositions containing anhydrous crystalline ascorbic acid 2-glucoside, it can be advantageously used as a cosmetic material, as well as a base material for quasi-drugs, pharmaceuticals, foods, etc. Since the product exhibits alkalinity when in an aqueous solution form, it can be advantageously used in preparing products, where unfavorable inconveniences are inevitably induced depending on a method of neutralizing ascorbic acid 2-glucoside with an alkali.

Example 3

<Cosmetic Material>

Fifty five parts by mass of a particulate composition containing anhydrous crystalline sodium salt of ascorbic acid 2-glucoside obtained by the method in Example 2 was admixed to homogeneity with 45 parts by mass of "AA2G", a product name of a particulate composition containing anhydrous crystalline ascorbic acid 2-glucoside commercialized by Hayashibara Co., Ltd., Okayama, Japan, to obtain a powdered cosmetic material.

The product is a composition of a novel particulate composition containing anhydrous crystalline sodium salt of ascorbic acid 2-glucoside and a conventionally frequently used particulate composition containing anhydrous crystalline ascorbic acid 2-glucoside, and, similarly as in conventional particulate compositions containing anhydrous crystalline ascorbic acid 2-glucoside, it can be advantageously used as a cosmetic material, as well as abase material for quasi-drugs, pharmaceuticals, foods, etc. Since the product exhibits a weak alkalinity when in an aqueous solution form, it facilitates the pH adjustment of final products to a desired pH compared to the use of conventional particulate compositions containing anhydrous crystalline ascorbic acid 2-glucoside.

Example 4

<Cosmetic Material>

Fifty parts by mass of a particulate composition containing hydrous crystalline sodium salt of ascorbic acid 2-glucoside obtained by the method in Example 1 was admixed to homogeneity with 50 parts by mass of "AA2G", a particulate composition containing anhydrous crystalline ascorbic acid 2-glucoside commercialized by Hayashibara Co., Ltd., Okayama, Japan, to obtain a powdered cosmetic material.

The product is a composition of a novel particulate composition containing hydrous crystalline sodium salt of ascorbic acid 2-glucoside and a conventionally frequently used particulate composition containing anhydrous crystalline ascorbic acid 2-glucoside, and, similarly as in conventional particulate composition containing anhydrous crystalline ascorbic acid 2-glucoside, it can be advantageously used as a cosmetic material, as well as a base material for quasi-drugs, pharmaceuticals, foods, etc. Since the product exhibits a weak acidity when in an aqueous solution form, it facilitates the pH adjustment of final products to a desired pH compared to the cases with conventional particulate compositions containing anhydrous crystalline ascorbic acid 2-glucoside.

Example 5

<Cosmetic Lotion>

(Formulation)

| Ingredient | (% by mass) |
|---|---|
| (1) Glycerin | 4.0 |
| (2) Propylene glycol | 3.0 |
| (3) 1,2-Pentane diol | 0.1 |

-continued

| Ingredient | (% by mass) |
|---|---|
| (4) Cosmetic material obtained by the method in Example 3 | 2.0 |
| (5) Polyoxyethylene (20 moles) olein alcohol | 0.5 |
| (6) *Saxifraga stolonifera* (beefsteak geranium) extract | 2.0 |
| (7) Ethanol | 5.0 |
| (8) Flavor | q.s. |
| (9) Refined water | Remaining |

The ingredients (1) to (4) in the above formulation were dissolved in refined water (9) and then gradually admixed with a mixture of the ingredients (5) to (8) to obtain a cosmetic lotion. The product is an improved cosmetic lotion that exerts a stable anti-wrinkle action and is useful as an anti-ageing cosmetic lotion that has an improved anti-wrinkle or anti-fine-wrinkle action, as well as having a skin-whitening, anti-blemish, or anti-sagging skin action, and maintaining or promoting the barrier function and the hyaluronic acid production in the skin. Since the product contains 1,2-pentane diol, it has a satisfactory antiseptic effect and a moisture-retaining ability, as well as having a lesser skin stimulation and being inhibited from precipitating effective ingredients such as ascorbic acid 2-glucoside.

Example 6

<Cosmetic Lotion>
(Formulation)

| Ingredient | (% by mass) |
|---|---|
| (1) Glycery monostearate | 0.5 |
| (2) *Olea europaea* [olive] oil | 0.5 |
| (3) Glycerin | 6.0 |
| (4) 1,3-Butylene glycol | 10.0 |
| (5) Ethanol | 5.0 |
| (6) Cosmetic material obtained by the method in Example 1 | 1.0 |
| (7) Arbutin | 1.0 |
| (8) Flavor | q.s. |
| (9) Refined water | Remaining |

(Production Method)

The ingredients (1) and (2) in the above formulation were mixed to homogeneity while heating at 70° C. and admixed with a mixture, which had been prepared by mixing the ingredients (3) and (4) with a part of refined water (9) and heating the resultant, to obtain a mixture (Phase A). Arbutin (7) was dissolved in the remaining refined water (9) into another mixture (Phase B). Phase A was gradually added to Phase B, mixed together, admixed with the ingredients (5) and (8), and added with the ingredient (6) to obtain a cosmetic lotion in the form of a microemulsion.

Since microemulsions are being formed in the product, it is transparent and high in stability and is an improved cosmetic lotion that exerts a stable anti-wrinkle action. The product is useful as an anti-ageing cosmetic lotion having improved anti-wrinkle, anti-fine-wrinkle, skin-whitening, anti-blemish, and anti-sagging-skin actions, as well as an action of maintaining or promoting the barrier function and the hyaluronic acid production in the skin. Since the product contains 1,3-butylene glycol, it has a satisfactory antiseptic effect and moisture-retaining ability, as well as having an improved antiseptic effect, moisture-retaining ability, and lesser skin stimulation.

Example 7

<Milky Lotion>
(Formulation)

| Ingredient | (% by mass) |
|---|---|
| (1) 1,2-Hexane diol | 5.0 |
| (2) Octyldodecanol | 4.0 |
| (3) Kojic acid | 1.0 |
| (4) Cosmetic material obtained by the method in Example 3 | 1.0 |
| (5) Polyoxyethyleneoleylether (20E.O.) | 1.0 |
| (6) Stearic acid | 0.5 |
| (7) Shea butter | 2.0 |
| (8) Beeswax | 4.0 |
| (9) Para-hydroxybenzonate | 0.2 |
| (10) *Cydonia oblonga* seed extract | 5.0 |
| (11) Xanthan gum | 0.1 |
| (12) Phytic acid | 0.02 |
| (13) Vitamin E | 0.01 |
| (14) Refined water | Remaining |

The above ingredients (1), (3), (10), and (11) and refined water (14) were mixed to obtain a water phase. The ingredients (2), (5) to (9), (12), and (13) were heated and mixed to obtain an oil phase. The water phase was added to the oil phase, mixed to homogeneity, cooled, and admixed to homogeneity with the ingredient (4) to obtain a milky lotion. The product is an improved milky lotion that exerts a stable anti-wrinkle action and is advantageously used as an anti-ageing milky lotion having an improved anti-wrinkle, anti-fine-wrinkle, skin-whitening, anti-blemish, and anti-sagging-skin actions, as well as having an improved action of maintaining or promoting the barrier function and the hyaluronic acid production in the skin.

Example 8

<Gel Milky Lotion>
(Formulation)

| Ingredient | (% by mass) |
|---|---|
| (1) Squalane | 5.0 |
| (2) Trioctanoin | 6.0 |
| (3) *Olea europaea* [olive] oil | 5.0 |
| (4) *Macadamia* nut oil | 5.0 |
| (5) Isopropyl palmitate | 5.0 |
| (6) Polyglyceryl (10) monomyristate | 5.5 |
| (7) POE-60 Glyceryl-10 isostearate | 3.0 |
| (8) Propylene glycol stearate SE | 2.0 |
| (9) Carboxyvinyl polymer | 0.5 |
| (10) Potassium hydroxide | q.s. |
| (11) "TORNARE", a product name of a syrup containing saccharide derivatives of trehalose, commercialized by Hayashibara Co., Ltd., Okayama, Japan | 15.5 |
| (12) Cosmetic material obtained by the method in Example 2 | 1.0 |
| (13) *Glycyrrhiza glabra* extract | 0.1 |
| (14) Hyaluronic acid | 0.25 |
| (15) 5'-Glucosyl adenosine | 0.2 |
| (16) 1,2-Pentane diol | 3.5 |
| (17) Flavor | q.s. |
| (18) Refined water | Remaining |

The ingredients (11) to (16) were dissolved in a part of refined water (18), added with the ingredients (11), (10), and (17), and emulsified in usual manner into a gel milky lotion. The product is a cosmetic gel that exerts a stable anti-wrinkle action, has an improved skin-whitening action, and has a satisfactory feeling of use without stickiness. Since the product contains no citric acid buffer and has a relatively low salt concentration, it is a satisfactory cosmetic gel, which has a relatively high stability and exerts a stable anti-wrinkle or anti-fine-wrinkle action, and is useful as an anti-ageing-gel-milky-lotion having an improved skin-whitening, anti-blemish, or anti-sagging skin action, as well as having an improved action of maintaining or promoting the barrier function and the hyaluronic acid production in the skin.

Example 9

<Cosmetic Milky Lotion>
(Formulation)

| Ingredient | (% by mass) |
| --- | --- |
| (1) Stearic acid | 2.5 |
| (2) Cetanol | 1.5 |
| (3) Petrolatum | 5.0 |
| (4) Liquid paraffin | 10.0 |
| (5) Polyoxyethylene oleate | 2.0 |
| (6) Tocopherol acetate | 0.5 |
| (7) Dipotassium glycyrrhizinate | 0.2 |
| (8) Polyethylene glycol 1500 | 3.0 |
| (9) Cosmetic material obtained by the method in Example 4 | 3.0 |
| (10) Aqueous extract of *Polygonum tinctorium* Lour. | 3.0 |
| (11) 1,2-Hexanediol | 0.1 |
| (12) Refined water | Remaining |

According to the above formulation, the ingredients were mixed in usual manner and further added with an adequate amount of flavor to obtain a milky lotion. The product is useful as an anti-ageing milky lotion that exerts a stable anti-wrinkle or anti-fine-wrinkle action, has an improved action of maintaining or promoting the barrier function and the hyaluronic acid production in the skin, and has a satisfactory feeling of use without stickiness when applied to the skin.

Example 10

<Cosmetic Cream>
(Formulation)

| Ingredient | (% by mass) |
| --- | --- |
| (1) Stearic acid | 5.0 |
| (2) Cetyl alcohol | 5.0 |
| (3) Squalane | 8.0 |
| (4) Petrolatum | 3.0 |
| (5) Glycerol tri(2-ethylhexanoate) | 7.0 |
| (6) Dipropylene glycol | 6.0 |
| (7) Glycerin | 4.0 |
| (8) Cosmetic material obtained by the method in Example 1 | 2.0 |
| (9) Propylene glycol monostearate | 3.0 |
| (10) Polyoxyethylene (20) cetyl alcohol ether | 3.0 |
| (11) 1,2-Hexanediol | 0.2 |
| (12) Flavor | q.s. |
| (13) Refined water | Remaining |

The ingredients (6) and (7) were added to refined water (13) and heated to 60° C. to prepare a water phase. The ingredients (1) to (5) and (9) to (12) were mixed and heated to 70° C. to obtain an oil phase, which was then added to the water phase prepared previously. The resulting mixture was added with the ingredient (8) and emulsified in usual manner to prepare a cream. The product is an anti-ageing cosmetic cream that has a stable anti-wrinkle action, improved skin-whitening effect, and improved action of maintaining or promoting the barrier function and the hyaluronic acid production in the skin; and has a satisfactory feeling of use without stickiness when applied to the skin.

Example 11

<Cosmetic Cream>
(Formulation)

| Ingredient | (% by mass) |
| --- | --- |
| (1) Decaglyceryl monostearate | 1.2 |
| (2) Decaglyceryl monomyristate | 1.8 |
| (3) Stearyl alcohol | 0.5 |
| (4) Behenyl alcohol | 3.0 |
| (5) Batyl alcohol | 1.0 |
| (6) Cetyl palmitate | 1.0 |
| (7) Glyceryl stearate | 1.8 |
| (8) C10-30 Cholesterol/lanosterol esters | 2.0 |
| (9) Isopropyl palmitate | 4.0 |
| (10) Squalane | 5.0 |
| (11) Octyldodecyl myristate | 5.0 |
| (12) *Macadamia* nut oil | 0.5 |
| (13) Trioctanoin | 1.8 |
| (14) Dimethicone | 0.3 |
| (15) Butylene glycol | 6.0 |
| (16) Pentylene glycol | 2.5 |
| (17) Concentrated glycerin | 12.0 |
| (18) Polyoctanium-51 | 0.25 |
| (19) Cosmetic material obtained by the method in Example 1 | 2.0 |
| (20) Anhydrous crystalline maltitol | 3.0 |
| (21) Flavor | q.s. |
| (22) Refined water | Remaining |

The ingredients (1) to (14) and (21) in the above formulation were mixed while heating into an oil phase. The ingredients (15) to (18), (20), and (22) were mixed to obtain a water phase. The water phase was mixed with the oil phase, cooled, and admixed with the ingredient (19) into a cream. The product is useful as an anti-ageing cosmetic cream that exerts a stable anti-wrinkle action and an improved skin-whitening action, has an improved action of maintaining or promoting the barrier function and the hyaluronic acid production in the skin, and has a satisfactory feeling of use without stickiness when applied to the skin.

Example 12

<Serum>
(Formulation)

| Ingredient | (% by mass) |
| --- | --- |
| (1) Maltitol | 7.5 |
| (2) Cosmetic material obtained by the method in Example 3 | 3.0 |
| (3) 1,2-Alkanediol | 5.0 |
| (4) Polyethylene glycol 1500 | 1.0 |
| (5) Ethanol | 5.0 |
| (6) Carboxy vinyl polymer | 0.4 |
| (7) Sodium polyacrylate | 0.1 |
| (8) Polyoxyethyleneoleylether (20E.O.) | 1.5 |
| (9) Olea europaea [olive] oil | 0.2 |
| (10) Dipotassium glycyrrhizate | 0.1 |
| (11) Potassium hydroxide | q.s. |
| (12) Flavor | q.s. |
| (13) Refined water | Remaining |

According to the above formulation, the ingredients were mixed in usual manner to obtain a serum. The product is useful as an anti-ageing serum that exerts a stable anti-wrinkle or anti-fine-wrinkle action, has an improved skin-whitening action, has an improved action of maintaining or promoting the barrier function and the hyaluronic acid production in the skin, and has a satisfactory feeling of use without stickiness when applied to the skin.

Example 13

<Pack>
(Formulation)

| Ingredient | (% by mass) |
|---|---|
| (1) Poly vinyl alcohol | 5.0 |
| (2) Pullulan | 12.0 |
| (3) Carboxymethyl cellulose | 6.0 |
| (4) 1,3-Bugtylene glycol | 6.0 |
| (5) Ethanol | 8.0 |
| (6) 1,2-Pentanediol | 0.1 |
| (7) Cosmetic material obtained by the method in Example 4 | 3.0 |
| (8) Polyoxyethyleneoleylether | 0.5 |
| (9) Flavor | q.s. |
| (10) Refined water | Remaining |

According to the above formulation, the ingredients were mixed in usual manner to obtain a pack. The product is useful as an anti-ageing pack that exerts a stable anti-wrinkle or anti-fine-wrinkle action and has an improved skin-whitening action and an action of maintaining or promoting the barrier function and the hyaluronic acid production in the skin. The product can be easily washed off from the skin after having been applied thereto for use.

Example 14

<Cleansing Foam>
(Formulation)

| Ingredient | (% by mass) |
|---|---|
| (1) Potassium laurate | 2.0 |
| (2) Potassium myristate | 17.0 |
| (3) Palmitic acid | 4.0 |
| (4) Stearic acid | 4.0 |
| (5) Palm kernel oil fatty acid diethanolamide | 3.0 |
| (6) Glycerin | 10.0 |
| (7) 1,3-Butylene glycol | 10.0 |
| (8) "TORNARE", a product name of a syrup containing saccharide derivatives of trehalose, commercialized by Hayashibara Co., Ltd., Okayama, Japan | 5.0 |
| (9) Cosmetic material obtained by the method in Example 2 | 3.0 |
| (10) Sodium ethylenediaminetetraacetic acid | 0.2 |
| (11) Sodium methyl cocoyl taurate | 10.0 |
| (12) Refined water | Remaining |

According to the above formulation, a cleansing foam was prepared in usual manner. The product is useful as a cleansing foam for anti-ageing because it exerts a stable anti-wrinkle or anti-fine-wrinkle action, has an improved action of maintaining or promoting the barrier function and the hyaluronic acid production in the skin, and has an improved skin-whitening and anti-blemish actions; and because you can enjoy its rich texture feeling after washing your face therewith.

Example 15

<Liquid Soap>
(Formulation)

| Ingredient | (% by mass) |
|---|---|
| (1) Lauric acid | 4.0 |
| (2) Propylene glycol stearate | 0.2 |
| (3) Octyldodeceth-10 | 1.5 |
| (4) Octyldodeceth-20 | 1.5 |
| (5) Ceteareth-60 myristyl glycol | 2.0 |
| (6) N-coconut oil fatty acid acyl glycin potassium solution | 10.0 |
| (7) Sodium cocoamphoacetate | 40.0 |
| (8) "TORNARE", a product name of a syrup containing saccharide derivatives of trehalose, commercialized by Hayashibara Co., Ltd., Okayama, Japan | 4.0 |
| (9) Cosmetic material obtained by the method in Example 1 | 2.0 |
| (10) Glycerin | 2.0 |
| (11) Disodium ethylenediaminetetraacetic acid | 0.2 |
| (12) Methylparaben | 0.1 |
| (13) Refined water | Remaining |

According to the above formulation, a liquid soap was prepared in usual manner. The product is useful as a liquid soap for anti-ageing because it exerts a stable anti-wrinkle or anti-fine-wrinkle action, has an improved action of maintaining or promoting the barrier function and the hyaluronic acid production in the skin, and has an improved skin-whitening and anti-blemish actions; and because you can enjoy its rich texture feeling after washing your face therewith.

Example 16

<Body Soap>
(Formulation)

| Ingredient | (% by mass) |
|---|---|
| (1) Lauric acid | 5.0 |
| (2) Oleic acid | 5.0 |
| (3) Sodium methyl cocoyl taurate | 18.0 |
| (4) Sodium cocoamphoacetate | 20.0 |
| (5) Hyaluronic acid | 2.0 |
| (6) "TORNARE", a product name of a syrup containing saccharide derivatives of trehalose, commercialized by Hayashibara Co., Ltd., Okayama, Japan | 1.0 |
| (7) Cosmetic material obtained by the method in Example 2 | 2.0 |
| (8) Sodium chloride | 0.2 |
| (9) Etidronic acid | 0.1 |
| (10) Disodium ethylenediaminetetraacetic acid | 0.1 |
| (11) Potassium hydroxide | q.s. |
| (12) Refined water | Remaining |

According to the above formulation, a body soap was prepared in usual manner. The product is useful as a body soap for anti-ageing because it exerts a stable anti-wrinkle or anti-fine-wrinkle action, has an improved action of maintaining or promoting the barrier function and the hyaluronic acid production in the skin, and has a skin-whitening and anti-blemish actions; and because you can enjoy its rich texture feeling after washing your face therewith.

Example 17

<Cleansing Cream>
(Formulation)

| Ingredient | (% by mass) |
|---|---|
| (1) Liquid paraffin | 35.0 |
| (2) Petrolatum | 17.0 |
| (3) Cetyl alcohol | 3.0 |
| (4) Stearic acid | 2.0 |
| (5) Glycerin | 3.0 |
| (6) Propylene glycol | 2.0 |
| (7) Polyoxyethylene isocetyl ether (10E.O.) | 2.5 |
| (8) Glycery monostearate | 2.5 |
| (9) 1,2-Pentanediol | 0.2 |
| (10) Cosmetic material obtained by the method in Example 3 | 1.0 |
| (11) Flavor | q.s. |
| (12) Refined water | Remaining |

According to the above formulation, a cleansing cream was prepared in usual manner. The product is directed for use in washing the skin and removing make-ups, and you can enjoy its rich texture feeling after washing your skin and face therewith. The product is useful as a cleansing cream for anti-ageing that exerts a stable anti-wrinkle or anti-fine-wrinkle action, has an improved action of maintaining or promoting the barrier function and the hyaluronic acid production in the skin, and has an improved skin-whitening and anti-blemish actions.

Example 18

<Sunscreen for Skin-Whitening (O/W Emulsion Type)>
(Formulation)

| Ingredient | (% by mass) |
|---|---|
| (1) Decaglyceryl pentaoleate | 1.5 |
| (2) Polyoxyethylene (10 moles) cholesteryl ether | 1.0 |
| (3) Hydrogenated soybean phospholipid | 1.5 |
| (4) Glycerin | 5.0 |
| (5) 2-Ethylhexyl p-methoxycinnamate | 5.0 |
| (6) Dipropylene glycol | 10.0 |
| (7) Arbutin | 3.0 |
| (8) Pentasodium diethylenetriaminepentaacetate | 0.1 |
| (9) Cosmetic material obtained by the method in Example 3 | 1.0 |
| (10) Malic acid | 0.2 |
| (11) Ethanol | 2.0 |
| (12) Flavor | q.s. |
| (13) Methyl 4-hydroxybenzoate | q.s. |
| (14) Sodium hydroxide | q.s. |
| (15) Refined water | Remaining |

(Production Method)
A. The ingredients (1) to (3) and (5) were heated to 75° C. and dissolved by mixing to homogeneity.
B. The ingredients (4), (6) to (10), (14), and (15) were heated to 75° C. and dissolved by mixing to homogeneity.
C. The above B was added to A and the resulting mixture was emulsified.
D. The above C was cooled and added with the ingredients (11) to (13) to obtain a sunscreen (skin-whitening type).

The product is useful as an anti-ageing sunscreen (O/W emulsion type) that exerts a stable skin-whitening action; has an improved anti-wrinkle action, anti-fine-wrinkle action, and improved action of maintaining or promoting the barrier function and the hyaluronic acid production in the skin; and has a uniform spreadability over the skin, lesser stickiness, improved moisture-retaining ability of smoothing the skin texture, etc., and improved temporal stability.

Example 19

<Skin-Whitening Milky Lotion (O/W Emulsion Type)>
(Formulation)

| Ingredient | (% by mass) |
|---|---|
| (1) Decaglyceryl pentastearate | 0.5 |
| (2) Polyoxyethylene (10 moles) cholesteryl ether | 0.2 |
| (3) Jojoba oil | 3.0 |
| (4) "LECINOL S-10", a hydrogenated soybean phospholipid commercialized by Nikko Chemicals Co., Ltd., Tokyo, Japan | 2.5 |
| (5) Glycerin | 5.0 |
| (6) Dipropylene glycol | 10.0 |
| (7) Arbutin | 7.0 |
| (8) Cosmetic material obtained by the method in Example 3 | 1.0 |
| (9) Disodium ethylenediaminetetraacetate | 0.1 |
| (10) Succinic acid | 0.1 |
| (11) Ethanol | 5.0 |
| (12) Sodium hydroxide | q.s. |
| (13) Refined water | Remaining |

(Production Method)
A. The ingredients (1) to (4) were heated to 75° C. and dissolved by mixing to homogeneity.
B. The ingredients (5) to (10), (12), and (13) were heated to 75° C. and dissolved by mixing to homogeneity.
C. The above B was added to A and the mixture was emulsified.
D. The above C was cooled and added with the ingredient (11) to obtain a skin-whitening milky lotion (O/W emulsion type).

The product is useful as a skin-whitening milky lotion for anti-ageing (O/W emulsion type) that exerts a stable anti-wrinkle or anti-fine-wrinkle action and has an improved action of maintaining or promoting the barrier function and the hyaluronic acid production in the skin, improved skin-whitening or anti-blemish action, uniform spreadability over the skin, lesser stickiness, improved moisture-retaining ability of smoothing the skin texture, etc., and improved temporal stability.

Example 20

<Cosmetic Base Material for Improving Skin Turnover>
(Formulation)

| Ingredient | (% by mass) |
|---|---|
| (1) "AA2G", a product name of a particulate composition containing anhydrous crystalline ascorbic acid 2-glucoside, commercialized by Hayashibara Co., Ltd., Okayama, Japan | 25.0 |

-continued

| Ingredient | (% by mass) |
| --- | --- |
| (2) "αG Rutin", a product name of α-glucosyl rutin commercialized by Toyo Sugar Refining Co., Ltd., Tokyo, Japan | 0.1 |
| (3) Polyoxyethylene alkyl ether | 0.9 |
| (4) Olea europaea [olive] leaf extract with skin-turnover-improving action | 0.01 |
| (5) Potassium hydroxide | q.s. |
| (6) Sodium citrate | q.s. |
| (7) Refined water | Remaining |

The above ingredients (1) to (7) were stirred at ambient temperature and mixed for dissolving, and the resulting mixture was filtered to obtain a base material for skin-turnover-improving cosmetic (pH 6.0), followed by being injected into a light-shielded container. By being incorporated into cosmetics, the product imparts a skin-turnover-improving action and stable anti-wrinkle or anti-fine-wrinkle action, as well as actions of maintaining or promoting the barrier function and the hyaluronic acid production in the skin, and of imparting skin-whitening, anti-blemish, and anti-sagging to the skin. Since, along with the action of the above ingredient (1), the product contains both the olive leaf extract and the α-glucosyl rutin capable of improving the skin turnover, it is distinctly useful in that it also effectively imparts an instant skin-turnover-improving action, skin-protecting action from ultraviolet ray, and antioxidant action. The product can be preferably incorporated into cosmetics as a rapidly effective fine-wrinkle-improving agent for women in midlife, let alone so-called pre-aging generation. Further, women, who are being pressed by daily works and liable to be negligent of their skin care, can be rapidly improved in their skin turnover by applying an appropriate amount of a cosmetic incorporated with the product to their skin at bedtime to effectively penetrate the effective ingredients into their skin during sleeping.

Example 21

<Cosmetic Base Material for Improving Skin Turnover>
(Formulation)

| Ingredient | (% by mass) |
| --- | --- |
| (1) "AA2G", a product name of a particulate composition containing anhydrous crystalline ascorbic acid 2-glucoside, commercialized by Hayashibara Co., Ltd., Okayama, Japan | 25.0 |
| (2) Ganoderma lucidum extract or Phallus impudicus extract | 0.01 |
| (3) Eucommia ulmoides leaf extract with skin-turnover-improving action and glycation-inhibitory action | 0.02 |
| (4) Glycerin-fatty acid ester | 0.8 |
| (5) Sodium hyaluronate | 1.0 |
| (6) Potassium hydroxide | q.s. |
| (7) Refined water | Remaining |

The above ingredients (1) to (7) were stirred at ambient temperature, dissolved by mixing, adjusted to pH 6.0, and filtered to obtain two types of base materials for skin-turnover-improving cosmetics. By being incorporated into cosmetics, the products impart a skin-turnover-improving action and a stable anti-wrinkle or anti-fine-wrinkle action, and impart an action of maintaining or promoting the barrier function and the hyaluronic acid production in the skin, as well as imparting a skin-whitening, anti-blemish, and anti-sagging skin actions. Since the products contain both the Eucommia ulmoides leaf extract with a skin-turnover-improving action and a glycation-inhibitory action and the Ganoderma lucidum extract or Phallus impudicus extract, it imparts an instant skin-turnover-improving effect and effectively exerts a skin ageing inhibitory effect, along with the action by the ingredient (1). Since the Eucommia ulmoides leaf extract with a skin-turnover-improving action, which is used in combination with ascorbic acid 2-glucoside, effectively inhibits the formation of advanced glycation end products (AGEs), unfavorable deposition of AGEs in skin tissues is lowered or inhibited, resulting in forming disordered cross-linkages in collagen intra- and inter-molecularly during the generation of AGEs to lower or inhibit the induction of physical and physiological changes (denaturations) in collagen, whereby the external signs of skin ageing such as wrinkles, rough skin, dullness, and reduction of firmness are effectively prevented or improved. The products can be preferably incorporated into cosmetics as rapidly effective fine-wrinkle-improving agents for women in midlife, let alone so-called pre-aging generation. Further, women, who are being pressed by daily works and liable to be negligent of their skin care, can be rapidly improved in their skin-turnover by applying an appropriate amount of a cosmetic incorporated with any one of the products to their skin at bedtime to effectively penetrate the effective ingredients into their skin during sleeping.

Example 22

<Cosmetic Base Material for Improving Skin Turnover>
(Formulation)

| Ingredient | (% by mass) |
| --- | --- |
| (1) "AA2G", a product name of a particulate composition containing anhydrous crystalline ascorbic acid 2-glucoside, commercialized by Hayashibara Co., Ltd., Okayama, Japan | 25.0 |
| (2) Polyoxyethylene alkyl ether | 0.9 |
| (3) Any one of the following extracts having a skin-turnover-improving action selected from Olea europaea extract, Glycyrrhiza uralensis extract, Triticum vulgare germ extract, Salvia officinalis extract, Mentha extract, Camellia japonica extract, Polygonum tinctorium Lour. leaf extract, Aloe barbadensis extract, Olea europaea extract, Matricaria recutita extract, Saxifraga stolonifera extract, Citrus junos extract, Citrus limon extract, Rosmarinus officinalis L. extract, Chlorellaceae extract, royal jelly extract, and Gardenia jasminoides extract. | 0.01 |
| (4) Potassium hydroxide | q.s. |
| (5) Sodium citrate | q.s. |
| (6) Refined water | Remaining |

Any one of the above ingredients (1), (2), and (3) and the above ingredients (4) to (6) were stirred at ambient temperature, mixed for dissolving, and filtered to obtain 17 types base materials (pH 6.0) for improving skin turnover, followed by being injected into light-shielded containers. By being incorporated into cosmetics, the products impart a skin-turnover-improving and stable anti-wrinkle actions or an anti-fine-wrinkle action, as well as actions of maintaining or promoting the barrier function and the hyaluronic acid production in the skin, and of skin-whitening, anti-blemish, and anti-sagging to the skin. Since, along with the action of the above ingredient (1), the products contain both the plant extract having a skin-turnover-improving action, it is distinctly useful in that they also effectively impart an instant skin-turnover-improving action, skin-protecting action from ultraviolet ray, and antioxidant action. The products can be preferably incorporated into cosmetics as a rapidly effective fine-wrinkle-improving agents for women in midlife, let alone so-called pre-aging generation. Further, women, who are being pressed by daily works and liable to be negligent of their skin care, can be rapidly improved in their skin turnovers by applying an appropriate amount of a cosmetic incorporated with any one of the products to their skin at bedtime to effectively penetrate the effective ingredients into their skin during sleeping.

Example 23

<Base Material for Antiseptic Cosmetics>
(Formulation)

| Ingredient | (% by mass) |
| --- | --- |
| (1) "AA2G", a product name of a particulate composition containing anhydrous crystalline ascorbic acid 2-glucoside, commercialized by Hayashibara Co., Ltd., Okayama, Japan | 25.0 |
| (2) "Kankohso 201" (PIONIN), commercialized by Hayashibara Co., Ltd., Okayama, Japan | 0.01 |
| (3) Any one of 1,2-Pentanediol, 1,2-hexanediol, 1,2-heptanediol, and 1,2-octanediol | 2.0 |
| (4) Hyaluronic acid | 1.0 |
| (5) *Paeonia lactiflora* extract having a glycation-inhibitory action | 1.0 |
| (6) Glycerin fatty acid ester | 0.8 |
| (7) "COSMETIC PULLULAN", a product name of pullulan, commercialized by Hayashibara Co., Ltd., Okayama, Japan | 0.4 |
| (8) Potassium hydroxide | q.s. |
| (9) Refined water | Remaining |

Either of the above ingredients (1) and (4) to (9), or the ingredient (2) and any one of the ingredient (3) were respectively stirred at ambient temperature and mixed for dissolving. The resulting solutions were mixed, adjusted to pH 6.0, filtered into four types of base materials for antiseptic cosmetics, and injected into light shielded containers. In particular, these products, which contain the *Paeonia lactiflora* extract having a glycation-inhibitory action, impart a distinct skin-turnover-improving effect, and effectively exert a skin anti-ageing inhibitory effect, along with the action of the ingredient (1). By being incorporated into cosmetics in a desired amount, the products can be made into liquid cosmetic base materials capable of imparting to such cosmetics a stable anti-wrinkle action, anti-fine-wrinkle action, action of maintaining or promoting the barrier function and the hyaluronic acid production in the skin, skin-whitening action, anti-blemish action, and anti-sagging action. Particularly, the products can be suitably incorporated into cosmetics as rapidly effective fine-wrinkle-improving agents for so called pre-aging generation including women in midlife. Since the products contain any one of the 1,2-pentanediol, 1,2-hexanediol, 1,2-heptanediol, and 1,2-octanediol having an antiseptic action and the Kankohso 201, having an improved compatibility with the above diols, at a relatively high concentration, they exert a superior antiseptic effect by being incorporated into cosmetics in an adequate amount. Since the products contain pullulan along with the ingredient (1), they are useful as cosmetic base materials capable of effectively imparting a moisturizing effect to the skin. In addition, cosmetics with anyone of the products rapidly improve the skin turnovers of women who are being pressed by daily works and liable to be negligent of their skin care, when applied to their skin in an appropriate amount at bedtime to effectively penetrate the effective ingredients into their skin during sleeping and to rapidly improve their skin turnovers.

Example 24

<Cosmetic Base Material for Improving Skin Turnover>
(Formulation)

| Ingredient | (% by mass) |
| --- | --- |
| (1) "AA2G", a product name of a particulate composition containing anhydrous crystalline ascorbic acid 2-glucoside, commercialized by Hayashibara Co., Ltd., Okayama, Japan | 25.0 |
| (2) Hyaluronic acid | 1.0 |
| (3) *Fragaria vesca* extract having a skin-turnover-improving action | 0.01 |
| (4) Equol having a skin-turnover-improving action and glycation-inhibitory action | 0.01 |
| (5) Polyoxyethylene hydrogenated castor oil | 1.0 |
| (6) Potassium hydroxide | q.s. |
| (7) Sodium citrate | q.s. |
| (8) Refined water | Remaining |

The above ingredients (1) to (8) were stirred while heating, mixed for dissolving, and filtered to obtain a base material (pH 6.0) for skin-turnover-improving cosmetics, followed by being injected into a light-shielded container. In particular, the product, which contains, along with the ingredient (1), the *Fragaria vesca* extract having a skin-turnover-improving action and the equol having a skin-turnover-improving action and a glycation-inhibitory action, effectively improves the skin turnover rapidly, exerts a stable anti-wrinkle action, anti-fine-wrinkle action, action of maintaining or promoting the barrier function and the hyaluronic acid production in the skin, skin-whitening action, anti-blemish action, and anti-sagging action. The product can be suitably incorporated into cosmetics as a rapidly effective fine-wrinkle-improving agent for women in midlife including so called pre-ageing generation. In addition, cosmetics with the product rapidly improve the skin turnovers of women who are being pressed by daily works and liable to be negligent of their skin care, when applied to their skin in an appropriate amount at bedtime to effectively penetrate the effective ingredients into their skin during sleeping and to rapidly improve their skin turnovers.

Example 25

<Cosmetic Base Material for Improving Skin Turnover>
(Formulation)

| Ingredient | (% by mass) |
|---|---|
| (1) "AA2G", a product name of a particulate composition containing anhydrous crystalline ascorbic acid 2-glucoside, commercialized by Hayashibara Co., Ltd., Okayama, Japan | 25.0 |
| (2) Hyaluronic acid | 1.0 |
| (3) One percent by mass of any one of extracts of *Withania somnifera*, *Thujopsis dolabrata*, *Acacia catechu*, *Ginkgo biloba*, *Gaultheria procumbens*, *Phellodendron amurense*, *Citrus sinensis*, seed of *Cucurbita*, bark of *Erythroxylum catuaba*, *Mallotus philippinensis*, *Fagopyrum esculentum*, *Davilla rugosa*, *Houttuynia cordata*, *Elatostema japonicum* var. *japonicum*, *Crassocephalum crepidioides*, *Actinidia polygama*, *Pleioblastus linearis*, *Rubus croceacanthus*, unripe fruit of *Malus pumila*, leaves of *Diospyros kaki* Thunberg, leaves of *Glycyrrhiza uralensis*, leaves of *Alpinia zerumbet*, protein hydrolyzates of pearls, equol, isoflavone, ifenprodil, catechol, caffeine acid, and prunin, which have a skin-turnover-improving action and/or a glycation-inhibitory action | |
| (4) Glycerin fatty acid ester | 0.8 |
| (5) Potassium hydroxide | q.s. |
| (6) Refined water | Remaining |

The above ingredients (4) to (6) and any one of the above ingredients (1) to (3) were mixed by stirring at ambient temperature, adjusted to pH 6.0, and filtered to obtain 32 types of base materials for skin-turnover-improving cosmetics, followed by being injected into light-shielded containers. In particular, these products, which contain, along with the action of the above ingredient (1), any of the above plant extracts having a skin-turnover-improving action and/or a glycation-inhibitory action and other ingredients, effectively impart a distinct skin-turnover-improving effect and exert a skin-ageing-inhibitory effect. When incorporated into various cosmetics in desired amounts, these products in the form of a cosmetic base material, impart a stable anti-wrinkle action, anti-fine-wrinkle action, action of maintaining or promoting the barrier function and the hyaluronic acid production in the skin, skin-whitening action, anti-blemish action, and anti-sagging action. Particularly, they can be suitably incorporated into various types of cosmetics as rapid, effective fine-wrinkle-improving agents for women in midlife including so called pre-ageing generation. In addition, cosmetics with any of these products rapidly improve the skin turnovers of women who are being pressed by daily works and liable to be negligent of their skin cares, when applied to their skin in an appropriate amount at bedtime to effectively penetrate the effective ingredients into their skin during sleeping and to rapidly improve their skin turnovers.

Example 26

<Skin-Turnover-Improving Agent>

According to the following formulation, four types of the present skin-turnover-improving agents were prepared by using, as the following ingredient (17), any one of the cosmetic base materials for improving skin turnover obtained in Examples 20, 21, where the cosmetic base material with *Ganoderma lucidum* extract was selected from the two types of cosmetic base materials, the cosmetic base material for improving skin turnover obtained in Example 24, and the particulate composition containing anhydrous crystalline ascorbic acid 2-glucoside.

<Test Cream>
(Formulation)

| Ingredient | (% by mass) |
|---|---|
| (1) Dimethicone | 0.3 |
| (2) Squalane | 2.0 |
| (3) Cetearyl isononanoate | 1.0 |
| (4) Triethylhexanoin | 2.0 |
| (5) Octyldodecanol | 2.0 |
| (6) C10-30 Cholesterol/lanosterol esters | 3.0 |
| (7) Polyglyceryl-10 myristate | 3.5 |
| (8) Cetyl alcohol | 3.5 |
| (9) Batyl alcohol | 1.0 |
| (10) Cetyl palmitate | 2.0 |
| (11) Glyceryl stearate SE | 2.5 |
| (12) Batyl stearate | 2.5 |
| (13) 1,3-Butylene glycol | 3.0 |
| (14) Methylparaben | 0.2 |
| (15) Glycerin | 4.5 |
| (16) "TORNARE", a product name of a syrup containing saccharide derivatives of trehalose, commercialized by Hayashibara Co., Ltd., Okayama, Japan | 2.0 |
| (17) 20.0% by mass of any one of cosmetic base materials for improving skin turnover obtained in Examples 20, 21 and 24; or 5.0% by mass of "AA2G", a product name of a particulate composition containing anhydrous crystalline 2-glucoside commercialized by Hayashibara Co., Ltd., Okayama, Japan | |
| (18) Malic acid | 0.02 |
| (19) Sodium malate | 0.3 |
| (20) Potassium hydroxide | 0.3 |
| (21) Lanolin | 0.1 |
| (22) Refined water | q.s. |

Since all the above four types of skin-turnover-improving agents exert outstanding fine-wrinkle-improving effects and have improving actions on fine-wrinkles accompanied by ageing, they are distinctly useful as rapidly effective anti-wrinkle-improving agents for women in midlife including so called pre-aging generation. The skin-turnover-improving agents, prepared with the cosmetic base material for improving skin turnover obtained in Example 21 or 24, contain ascorbic acid 2-glucoside and other ingredient with a skin-turnover-improving action and a glycation-inhibitory action; the agents exert a more improved skin-turnover-rate-improving action than those prepared with the cosmetic base material for improving skin turnover in Example 20, which had been incorporated with only the ingredient having a skin-turnover-improving action along with ascorbic acid 2-glucoside. The skin-turnover-improving agent, prepared with the cosmetic base material for improving skin turnover in Example 20, exerts a more improved skin-turnover-rate-improving action than that prepared with a particulate composition containing anhydrous crystalline ascorbic acid 2-glucoside as the above ingredient (17); and also exerts an action of maintaining or promoting the skin barrier function and the hyaluronic acid production in the skin, as well as a skin-whitening action, anti-blemish action, and anti-sagging action.

INDUSTRIAL APPLICABILITY

The external dermal composition and the basic skin cares such as cosmetic lotions, face washes, serums, milky lotions, and creams, all of which contain the composition, according to the present invention, have an improved anti-wrinkle, anti-fine-wrinkle, anti-blemish, and anti-sagging skin effects, and thus they are outstandingly useful as a means for realizing a common and universal desire of humans who wish to be young to the end of time.

Also, the external dermal composition and the basic skin cares such as cosmetic lotions, face washes, serums, milky lotions, and creams, all of which contain the composition, according to the present invention, are easily produced by a production method containing a step of mixing the desired effective ingredient(s) with an aqueous medium; the use of a crystalline form of ascorbic acid 2-glucoside or of a sodium salt thereof as a particularly suitable effective ingredient will provide a distinctly advantageous benefit of expecting constantly fixed or unchangeable known and stable properties, let alone an advantage of affording the use of high-purity raw materials with lesser impurities.

Further, in the case of using crystalline sodium salt of ascorbic acid 2-glucoside and anhydrous crystalline ascorbic acid 2-glucoside in combination, an appropriate control of the ratio of the above ingredients enables the pH adjustment of final products to a pH within a prescribed pH range, without neutralizing ascorbic acid 2-glucoside with an alkali; whereby the external dermal composition for anti-ageing and the basic skin cares such as cosmetic lotions, face washes, serums, milky lotions, and creams, all of which contain the composition, according to the present invention, can be readily produced with a lesser production step(s). The present invention with such outstanding various advantages has a distinctly significant industrial usefulness.

The invention claimed is:

1. A composition which comprises 2-O-α-D-glucosyl-L-ascorbic acid and sodium salt thereof that are in a crystalline form.

2. The composition of claim 1, wherein the ratio of said 2-O-α-D-glucosyl-L-ascorbic acid and said sodium salt thereof is in the range of 60:40 to 45:55 by mass, on a dry solid basis.

3. The composition of claim 1, wherein said sodium salt of 2-O-α-D-glucosyl-L-ascorbic acid in a crystalline form is a hydrous crystalline sodium salt of 2-O-α-D-glucosyl-L-ascorbic acid having diffraction angles (2θ) of 6.8°, 8.2°, 14.3°, 17.8°, and 18.4°; or an anhydrous crystalline sodium salt of 2-O-α-D-glucosyl-L-ascorbic acid having diffraction angles (2θ) of 8.0°, 9.0°, 16.4°, 17.9°, and 20.8°, when determined on powder X-ray diffraction analysis.

4. A crystal of sodium salt of 2-O-α-D-glucosyl-L-ascorbic acid.

5. The crystal of claim 4, which is in a hydrous crystalline form having diffraction peaks at diffraction angles (2θ) of 6.8°, 8.2°, 14.3°, 17.8°, and 18.4°, or in an anhydrous crystalline form having diffraction peaks at diffraction angles (2θ) of 8.0°, 9.0°, 16.4°, 17.9°, and 20.8°.

6. The crystal of claim 5, wherein said hydrous crystal belongs to an orthorhombic system and exhibits a space group of Pbca (#61) and a lattice constant of a=6.9733 Å, b=14.4839 Å, c=19.3221 Å, and V=1951.54 Å$^3$.

7. A method for producing said crystal of sodium salt of 2-O-α-D-glucosyl-L-ascorbic acid of claim 4, which comprises the steps of:
  (a) dissolving 2-O-α-D-glucosyl-L-ascorbic acid in an aqueous sodium hydroxide solution;
  (b) adding an organic solvent to the resulting solution;
  (c) allowing the resulting mixture to stand to precipitate a crystal of sodium salt of 2-O-α-D-glucosyl-L-ascorbic acid; and
  (d) collecting the precipitated crystal.

8. A composition comprising the crystal of sodium salt of 2-O-α-D-glucosyl-L-ascorbic acid of claim 4.

9. The composition of claim 8, which further comprises L-ascorbic acid or its derivative including a glycosyl-, acyl-, or phosphoryl-derivative of L-ascorbic acid.

10. The composition of claim 9, wherein said glycosyl-derivative of L-ascorbic acid is 2-O-α-D-glucosyl-L-ascorbic acid.

* * * * *